US009453251B2

(12) United States Patent
Retallack et al.

(10) Patent No.: US 9,453,251 B2
(45) Date of Patent: *Sep. 27, 2016

(54) **EXPRESSION OF MAMMALIAN PROTEINS IN *PSEUDOMONAS FLUORESCENS***

(75) Inventors: Diane M. Retallack, Poway, CA (US); Charles H. Squires, Poway, CA (US); David C. Watkins, East Greenwich, RI (US); Stacey L. Lee, San Diego, CA (US); Frank H. Gaertner, San Diego, CA (US); Robert Shutter, Poway, CA (US)

(73) Assignee: PFENEX INC., San Diego, CA (US)

( * ) Notice: Subject to any disclaimer, the term of this patent is extended or adjusted under 35 U.S.C. 154(b) by 507 days.

This patent is subject to a terminal disclaimer.

(21) Appl. No.: 11/038,901

(22) Filed: Jan. 18, 2005

(65) Prior Publication Data

US 2006/0040352 A1    Feb. 23, 2006

Related U.S. Application Data

(63) Continuation-in-part of application No. 10/681,540, filed on Oct. 7, 2003, now Pat. No. 7,338,794.

(60) Provisional application No. 60/564,798, filed on Apr. 22, 2004, provisional application No. 60/537,148, filed on Jan. 16, 2004, provisional application No. 60/417,124, filed on Oct. 8, 2002.

(51) Int. Cl.
| | |
|---|---|
| *C12P 21/06* | (2006.01) |
| *C12P 21/02* | (2006.01) |
| *C07K 16/40* | (2006.01) |
| *C12N 15/78* | (2006.01) |

(52) U.S. Cl.
CPC ............... *C12P 21/02* (2013.01); *C07K 16/40* (2013.01); *C12N 15/78* (2013.01); *C07K 2317/622* (2013.01)

(58) Field of Classification Search
None
See application file for complete search history.

(56) References Cited

U.S. PATENT DOCUMENTS

| | | | |
|---|---|---|---|
| 3,844,893 A | 10/1974 | Hitzman | |
| 3,878,093 A | 4/1975 | Kanani et al. | |
| 4,169,010 A | 9/1979 | Marwil | |
| 4,432,895 A | 2/1984 | Tarnowski | |
| 4,511,503 A | 4/1985 | Olson et al. | |
| 4,551,433 A | 11/1985 | DeBoer | |
| 4,595,658 A | 6/1986 | Zinder et al. | |
| 4,637,980 A | 1/1987 | Auerbach et al. | |
| 4,680,264 A | 7/1987 | Puhler et al. | |
| 4,695,455 A | 9/1987 | Barnes et al. | |
| 4,695,462 A | 9/1987 | Barnes et al. | |
| 4,755,465 A | 7/1988 | Gray et al. | |
| 4,861,595 A | 8/1989 | Barnes et al. | |
| 5,023,171 A | 6/1991 | Ho et al. | |
| 5,043,430 A * | 8/1991 | Yoshikawa | 530/399 |
| 5,055,294 A | 10/1991 | Gilroy | |
| 5,084,559 A | 1/1992 | Profy | |
| 5,085,862 A | 2/1992 | Klein et al. | |
| 5,128,130 A | 7/1992 | Gilroy et al. | |
| 5,169,760 A | 12/1992 | Wilcox | |
| 5,173,616 A | 12/1992 | Hinooka | |
| 5,232,840 A * | 8/1993 | Olins | 435/69.1 |
| 5,281,532 A | 1/1994 | Rammler et al. | |
| 5,292,507 A | 3/1994 | Charley | |
| 5,418,155 A | 5/1995 | Cormier et al. | |
| 5,441,934 A | 8/1995 | Krapcho et al. | |
| 5,527,883 A | 6/1996 | Thompson et al. | |
| 5,552,302 A * | 9/1996 | Lewis et al. | 435/69.2 |
| 5,558,862 A | 9/1996 | Corbin et al. | |
| 5,559,015 A | 9/1996 | Capage et al. | |
| 5,595,898 A | 1/1997 | Robinson et al. | |
| 5,610,044 A | 3/1997 | Lam et al. | |
| 5,622,846 A | 4/1997 | Kiener et al. | |
| 5,641,671 A | 6/1997 | Bos et al. | |
| 5,643,774 A | 7/1997 | Ligon et al. | |
| 5,662,898 A | 9/1997 | Ligon et al. | |
| 5,677,127 A | 10/1997 | Hogan et al. | |
| 5,683,888 A | 11/1997 | Campbell | |
| 5,686,282 A | 11/1997 | Lam et al. | |
| 5,686,283 A | 11/1997 | Gaffney et al. | |
| 5,698,425 A | 12/1997 | Ligon et al. | |
| 5,698,435 A | 12/1997 | Robinson et al. | |
| 5,710,031 A | 1/1998 | Gaffney et al. | |
| 5,728,574 A | 3/1998 | Legg | |

(Continued)

FOREIGN PATENT DOCUMENTS

| | | |
|---|---|---|
| EP | 0121352 | 10/1984 |
| EP | 0177343 A1 | 4/1986 |

(Continued)

OTHER PUBLICATIONS

Landry et al., Regulatory Toxicology and Pharmacology, Feb. 2003, vol. 37, pp. 149-168.*
Smits et al (Plasmid, 2001, vol. 46, p. 16-24.*
Gray et al (Bio/Technology, Feb. 1984, pp. 161-165).*
Mezghani-Abdelmoula et al (African Journal of Clinical and Experimental Microbiology, Jan. 2005, pp. 1-13).*
Georgiou et al in "Preparative expression of secreted proteins in bacteria: status report and future prospects" (Current Opinion in Biotechnology:2005 vol. 16, pp. 538-545).*
Ahn et al., "Homologous Expression of the Lipease and ABC Transporter Gene Cluster, tliDEFA, Enhances Lipase Secretion in *Pseudomanas* spp." Applied and Environmental Microbiology. Dec. 2001, vol. 67, No. 12, pp. 5506-5511.

(Continued)

*Primary Examiner* — Catherine S Hibbert
(74) *Attorney, Agent, or Firm* — Wilson Sonsini Goodrich & Rosati

(57) ABSTRACT

The invention is a process for improved production of a recombinant mammalian protein by expression in a Pseudomonad, particularly in a *Pseudomonas fluorescens* organism. The process improves production of mammalian proteins, particularly human or human-derived proteins, over known expression systems such as *E. coli* in comparable circumstances Processes for improved production of isolated mammalian, particularly human, proteins are provided.

24 Claims, 11 Drawing Sheets

(56) References Cited

U.S. PATENT DOCUMENTS

| | | |
|---|---|---|
| 5,731,280 A | 3/1998 | Nielsen et al. |
| 5,736,379 A | 4/1998 | Davie et al. |
| 5,741,663 A | 4/1998 | Russell |
| 5,741,668 A | 4/1998 | Ward et al. |
| 5,756,087 A | 5/1998 | Ligon et al. |
| 5,757,051 A | 5/1998 | Wu et al. |
| 5,766,926 A | 6/1998 | Blanchette et al. |
| 5,773,600 A | 6/1998 | Burnette, III |
| 5,776,730 A | 7/1998 | Stuart |
| 5,777,079 A | 7/1998 | Tsien et al. |
| 5,795,759 A | 8/1998 | Rosazza et al. |
| 5,804,387 A | 9/1998 | Cormack et al. |
| 5,824,472 A | 10/1998 | Betlach et al. |
| 5,834,250 A | 11/1998 | Wells et al. |
| 5,840,554 A | 11/1998 | Thompson et al. |
| 5,869,038 A | 2/1999 | Leifert et al. |
| 5,874,304 A | 2/1999 | Zolotukhin et al. |
| 5,891,688 A | 4/1999 | Gaffney et al. |
| 5,914,233 A | 6/1999 | Mundy et al. |
| 5,914,254 A | 6/1999 | Mascarenhas et al. |
| 5,919,445 A | 7/1999 | Chao |
| 5,922,576 A | 7/1999 | He et al. |
| 5,925,558 A | 7/1999 | Tsien et al. |
| 5,932,435 A | 8/1999 | Atkins et al. |
| 5,942,387 A | 8/1999 | Hollinshead |
| 5,948,681 A | 9/1999 | Scanlin et al. |
| 5,948,889 A | 9/1999 | de Boer et al. |
| 5,952,208 A | 9/1999 | Darzins et al. |
| 5,955,348 A | 9/1999 | Ligon et al. |
| 5,958,713 A | 9/1999 | Thastrup et al. |
| 5,968,738 A | 10/1999 | Anderson et al. |
| 5,968,773 A | 10/1999 | Heddle et al. |
| 5,968,779 A * | 10/1999 | Campfield et al. .......... 435/69.4 |
| 5,985,577 A | 11/1999 | Bulinski |
| 5,986,779 A | 11/1999 | Campfield et al. |
| 5,989,808 A | 11/1999 | Young et al. |
| 5,993,778 A | 11/1999 | Firestein et al. |
| 5,994,071 A | 11/1999 | Ross et al. |
| 5,994,077 A | 11/1999 | Valdivia et al. |
| 6,013,447 A | 1/2000 | Nilsen et al. |
| 6,015,557 A | 1/2000 | Tobinick et al. |
| 6,020,192 A | 2/2000 | Muzyczka et al. |
| 6,037,133 A | 3/2000 | Li |
| 6,040,138 A | 3/2000 | Lockhart et al. |
| 6,051,383 A | 4/2000 | Thomashow et al. |
| 6,054,321 A | 4/2000 | Tsien et al. |
| 6,060,247 A | 5/2000 | Miller et al. |
| 6,066,476 A | 5/2000 | Tsien et al. |
| 6,071,738 A | 6/2000 | Johnson et al. |
| 6,077,707 A | 6/2000 | Tsien et al. |
| 6,080,576 A | 6/2000 | Zambrowicz et al. |
| 6,083,690 A | 7/2000 | Harris et al. |
| 6,090,919 A | 7/2000 | Cormack et al. |
| 6,093,808 A | 7/2000 | Li |
| 6,096,717 A | 8/2000 | Jarvik |
| 6,096,865 A | 8/2000 | Michaels |
| 6,110,711 A | 8/2000 | Serafini et al. |
| 6,117,670 A | 9/2000 | Ligon et al. |
| 6,121,247 A | 9/2000 | Huang et al. |
| 6,124,128 A | 9/2000 | Tsien et al. |
| 6,130,313 A | 10/2000 | Li et al. |
| 6,133,429 A | 10/2000 | Davis et al. |
| 6,136,538 A | 10/2000 | Olivo et al. |
| 6,136,539 A | 10/2000 | Basbaum et al. |
| 6,136,566 A | 10/2000 | Sands et al. |
| 6,140,132 A | 10/2000 | Tsien et al. |
| 6,146,826 A | 11/2000 | Chalfie et al. |
| 6,150,176 A | 11/2000 | Tsien et al. |
| 6,156,313 A | 12/2000 | Burton et al. |
| 6,156,552 A | 12/2000 | Okkels et al. |
| 6,180,343 B1 | 1/2001 | Anderson et al. |
| 6,184,440 B1 | 2/2001 | Shoseyov et al. |
| 6,194,194 B1 | 2/2001 | Molloy |
| 6,197,928 B1 | 3/2001 | Tsien et al. |
| 6,203,986 B1 | 3/2001 | Singer et al. |
| 6,204,023 B1 | 3/2001 | Robinson et al. |
| 6,210,910 B1 | 4/2001 | Walt et al. |
| 6,214,563 B1 | 4/2001 | Negulescu et al. |
| 6,214,567 B1 | 4/2001 | Allen-Hoffmann et al. |
| 6,218,185 B1 | 4/2001 | Shirk et al. |
| 6,221,612 B1 | 4/2001 | Knapp et al. |
| 6,225,082 B1 | 5/2001 | Carson et al. |
| 6,232,107 B1 | 5/2001 | Bryan et al. |
| 6,246,543 B1 | 6/2001 | Baumgart et al. |
| 6,248,550 B1 | 6/2001 | Tsien et al. |
| 6,248,558 B1 | 6/2001 | Lin et al. |
| 6,251,384 B1 | 6/2001 | Tan et al. |
| 6,251,582 B1 | 6/2001 | Littman et al. |
| 6,251,602 B1 | 6/2001 | Young et al. |
| 6,251,677 B1 | 6/2001 | Wilson et al. |
| 6,255,071 B1 | 7/2001 | Beach et al. |
| 6,255,558 B1 | 7/2001 | Haseloff et al. |
| 6,258,560 B1 | 7/2001 | Leung et al. |
| 6,261,760 B1 | 7/2001 | Fielding et al. |
| 6,261,776 B1 | 7/2001 | Pirrung et al. |
| 6,265,548 B1 | 7/2001 | Pavlakis et al. |
| 6,268,201 B1 | 7/2001 | Alland et al. |
| 6,268,549 B1 | 7/2001 | Sailland et al. |
| 6,270,958 B1 | 8/2001 | Olivo et al. |
| 6,274,354 B1 | 8/2001 | Wilson et al. |
| 6,277,625 B1 | 8/2001 | Huang et al. |
| 6,284,519 B1 | 9/2001 | Young et al. |
| 6,291,175 B1 | 9/2001 | Sevigny et al. |
| 6,303,373 B1 | 10/2001 | Bogan et al. |
| 6,316,181 B1 | 11/2001 | Fillmore et al. |
| 6,319,669 B1 | 11/2001 | Tsien et al. |
| 6,329,172 B1 | 12/2001 | Rhee et al. |
| 6,344,316 B1 | 2/2002 | Lockhart et al. |
| 6,372,225 B1 | 4/2002 | Matsuda et al. |
| 6,403,957 B1 | 6/2002 | Fodor et al. |
| 6,410,229 B1 | 6/2002 | Lockhart et al. |
| 6,420,108 B2 | 7/2002 | Mack et al. |
| 6,447,770 B1 | 9/2002 | Raaijmakers et al. |
| 6,451,536 B1 | 9/2002 | Fodor et al. |
| 6,495,357 B1 | 12/2002 | Fuglsang et al. |
| 6,506,559 B1 | 1/2003 | Fire et al. |
| 6,509,181 B1 | 1/2003 | Danielsen et al. |
| 6,524,827 B2 | 2/2003 | Moller et al. |
| 6,528,298 B1 | 3/2003 | Svendsen et al. |
| 6,532,462 B2 | 3/2003 | Balaban |
| 6,551,784 B2 | 4/2003 | Fodor et al. |
| 6,558,939 B1 | 5/2003 | Nørregaard-Madsen et al. |
| 6,567,540 B2 | 5/2003 | Balaban et al. |
| 6,573,099 B2 | 6/2003 | Graham |
| 6,576,424 B2 | 6/2003 | Fodor et al. |
| 6,600,031 B1 | 7/2003 | Fodor et al. |
| 6,607,885 B1 | 8/2003 | Larossa et al. |
| 6,608,018 B1 | 8/2003 | Shinohara |
| 6,617,143 B1 | 9/2003 | Fukuyama |
| 6,642,030 B1 | 11/2003 | English et al. |
| 6,673,580 B2 | 1/2004 | Koren et al. |
| 6,687,692 B1 | 2/2004 | Balaban et al. |
| 6,696,561 B1 | 2/2004 | Pompujus et al. |
| 6,800,738 B1 | 10/2004 | Carter et al. |
| 6,979,556 B2 | 12/2005 | Simmons et al. |
| 7,112,324 B1 | 9/2006 | Dorken et al. |
| 7,175,840 B2 | 2/2007 | Kim et al. |
| 7,189,389 B2 | 3/2007 | Yanai et al. |
| 7,217,796 B2 | 5/2007 | Wang et al. |
| 7,235,641 B2 | 6/2007 | Kufer et al. |
| 7,270,993 B2 | 9/2007 | Smit et al. |
| 7,338,794 B2 | 3/2008 | Gaertner et al. |
| 7,381,804 B2 | 6/2008 | Osslund |
| 7,399,463 B2 | 7/2008 | Shirley et al. |
| 7,416,849 B2 | 8/2008 | Allen et al. |
| 7,427,596 B2 | 9/2008 | Keyt et al. |
| 7,439,063 B2 | 10/2008 | Digicaylioglu et al. |
| 7,439,323 B2 | 10/2008 | Bielicki |
| 7,445,772 B2 | 11/2008 | West et al. |
| 7,452,971 B2 | 11/2008 | Vitetta et al. |
| 7,459,540 B1 | 12/2008 | Thomason et al. |
| 7,491,697 B2 | 2/2009 | Beals et al. |
| 7,504,237 B2 | 3/2009 | Jensen et al. |
| 7,524,931 B2 | 4/2009 | Van Den Hazel et al. |

(56) References Cited

U.S. PATENT DOCUMENTS

| | | | |
|---|---|---|---|
| 7,537,771 | B2 | 5/2009 | Williamson et al. |
| 7,544,519 | B2 | 6/2009 | Hsu et al. |
| 7,547,821 | B2 | 6/2009 | Moloney et al. |
| 7,553,940 | B2 | 6/2009 | Fares et al. |
| 7,553,941 | B2 | 6/2009 | Fares et al. |
| 7,556,817 | B2 | 7/2009 | Steward et al. |
| 7,560,112 | B2 | 7/2009 | Chen et al. |
| 7,563,443 | B2 | 7/2009 | Grant et al. |
| 7,566,566 | B2 | 7/2009 | Alitalo et al. |
| 7,566,769 | B2 | 7/2009 | Browning et al. |
| 7,575,923 | B2 | 8/2009 | Dorken et al. |
| 7,576,190 | B2 | 8/2009 | Glaesner et al. |
| 7,582,607 | B2 | 9/2009 | Frye et al. |
| 7,585,942 | B2 | 9/2009 | Harrison et al. |
| 7,618,799 | B2 | 11/2009 | Coleman et al. |
| 7,985,564 | B2 | 7/2011 | Retallack et al. |
| 8,288,127 | B2 | 10/2012 | Schneider et al. |
| 8,603,824 | B2 | 12/2013 | Ramseier et al. |
| 2003/0013150 | A1 | 1/2003 | Manosroi et al. |
| 2003/0044906 | A1 | 3/2003 | Habermann et al. |
| 2003/0064435 | A1 | 4/2003 | Weiner et al. |
| 2003/0108923 | A1 | 6/2003 | Tuschl et al. |
| 2003/0114409 | A1 | 6/2003 | Mello et al. |
| 2003/0157069 | A1 | 8/2003 | Lyman et al. |
| 2003/0180937 | A1 | 9/2003 | Georgiou et al. |
| 2004/0138127 | A1 | 7/2004 | Davidson et al. |
| 2004/0146484 | A1* | 7/2004 | Gaertner et al. .............. 424/85.1 |
| 2004/0180378 | A1 | 9/2004 | Tozer et al. |
| 2005/0186666 | A1 | 8/2005 | Schneider et al. |
| 2005/0214321 | A1 | 9/2005 | Rasochova et al. |
| 2006/0008877 | A1 | 1/2006 | Retallack et al. |
| 2006/0040352 | A1 | 2/2006 | Retallack et al. |
| 2006/0062784 | A1 | 3/2006 | Grant et al. |
| 2006/0110747 | A1 | 5/2006 | Ramseier et al. |
| 2006/0115470 | A1 | 6/2006 | Silence et al. |
| 2006/0149041 | A1 | 7/2006 | Silence |
| 2006/0193852 | A1 | 8/2006 | Dorken et al. |
| 2006/0211088 | A1 | 9/2006 | Hermans et al. |
| 2006/0234346 | A1 | 10/2006 | Retallack et al. |
| 2006/0246477 | A1 | 11/2006 | Hermans et al. |
| 2007/0123479 | A1 | 5/2007 | Kufer et al. |
| 2008/0107601 | A1 | 5/2008 | Lauwereys et al. |
| 2008/0107673 | A1 | 5/2008 | Ballard et al. |
| 2008/0267949 | A1 | 10/2008 | Revets et al. |
| 2009/0062143 | A1 | 3/2009 | Ramseier et al. |
| 2009/0148438 | A1 | 6/2009 | Nuttal et al. |
| 2009/0226432 | A1 | 9/2009 | Lutterbuse et al. |
| 2009/0226444 | A1 | 9/2009 | Rau et al. |
| 2009/0238829 | A1 | 9/2009 | Silence et al. |
| 2014/0162279 | A1 | 6/2014 | Ramseier et al. |

FOREIGN PATENT DOCUMENTS

| | | |
|---|---|---|
| EP | 0288451 A2 | 10/1988 |
| EP | 0 404 097 | 12/1990 |
| EP | 0 207 459 B1 | 3/1991 |
| EP | 0207459 B1 | 3/1991 |
| JP | 2001-299360 A | 10/2001 |
| JP | 2001-299360 A | 10/2001 |
| JP | 2004502929 A | 1/2004 |
| JP | 2006-501811 | 1/2006 |
| JP | H9-506508 | 6/2009 |
| WO | WO 87/05937 | 10/1987 |
| WO | WO 87/05938 | 10/1987 |
| WO | WO-89-10971 | 11/1989 |
| WO | WO-90-03438 | 4/1990 |
| WO | WO-92-15673 | 9/1992 |
| WO | WO-93-11161 | 6/1993 |
| WO | WO 95/03395 | 2/1995 |
| WO | WO-95-07463 | 3/1995 |
| WO | WO-96-17943 | 6/1996 |
| WO | WO-97-22687 A1 | 6/1997 |
| WO | WO-98-14605 | 4/1998 |
| WO | WO 98/24919 | 6/1998 |
| WO | WO-98-26277 | 6/1998 |
| WO | WO 99/09834 | 3/1999 |
| WO | WO-99-15650 | 4/1999 |
| WO | WO 99-49019 | 9/1999 |
| WO | WO 99/53035 | 10/1999 |
| WO | WO 00/15761 | 3/2000 |
| WO | WO 00/29604 | 5/2000 |
| WO | WO-00-59537 | 10/2000 |
| WO | WO-01-21662 | 3/2001 |
| WO | WO 01/27258 | 4/2001 |
| WO | WO-01-32844 A1 | 5/2001 |
| WO | WO 02-02794 | 1/2002 |
| WO | WO 02/14551 | 2/2002 |
| WO | WO 02/16940 | 2/2002 |
| WO | WO-02-40696 | 5/2002 |
| WO | WO-02-48376 A2 | 6/2002 |
| WO | WO 02/068660 | 9/2002 |
| WO | WO-02-068660 | 9/2002 |
| WO | WO-03-006477 | 1/2003 |
| WO | WO-03-012052 | 2/2003 |
| WO | WO-03-023015 | 3/2003 |
| WO | WO-03-056022 | 7/2003 |
| WO | WO-03-0064435 | 8/2003 |
| WO | WO-03-064621 | 8/2003 |
| WO | WO 03/068926 | 8/2003 |
| WO | WO 03/068926 A2 | 8/2003 |
| WO | WO-03-070966 | 8/2003 |
| WO | WO-03-079007 | 9/2003 |
| WO | WO 03/089455 | 10/2003 |
| WO | WO 03/089455 A2 | 10/2003 |
| WO | WO 2004/005221 | 1/2004 |
| WO | WO 2004/005221 A2 | 1/2004 |
| WO | WO 2004/006657 | 1/2004 |
| WO | WO 2004/011628 | 2/2004 |
| WO | WO-2004-055206 | 7/2004 |
| WO | WO 2004/087864 | 10/2004 |
| WO | WO-2005-014639 A2 | 2/2005 |
| WO | WO-2005-052151 A1 | 6/2005 |
| WO | WO-2005-069913 | 8/2005 |
| WO | WO-2005-089093 | 9/2005 |
| WO | WO-2005-103077 | 11/2005 |
| WO | WO-2005-115622 | 12/2005 |
| WO | WO-2006-014899 | 2/2006 |
| WO | WO 2006-059701 | 6/2006 |
| WO | WO-2006-066001 | 6/2006 |
| WO | WO-2008-017906 | 2/2008 |
| WO | WO-2008-134461 | 7/2008 |
| WO | WO-2008-094986 | 8/2008 |

OTHER PUBLICATIONS

Gaertner, "Amended Recombinant Cells (ARCs) for the Production and Delivery of INF-y," presentation of Mar. 18, 2004 at Florida A&M University, pp. 1-26.

Goeddel et al., Expression in *Escherichia coli* of chemically synthesized genes for human insulin, Jan. 1979, Proc. Natl. Acad. Sci. USA, vol. 76, No. 1, pp. 106-110.

Casavant, Carol, et al., Use of a site-specific recombination-based biosensor for detecting bioavailable toluene and related compounds on roots, Environmental Microbiology, Apr. 2003, pp. 238-249, vol. 5, No. 4, Society for Applied Microbiology.

De Marco, Ario, et al., Native Folding of Aggregation-Prone Recombinant Proteins in *Escherichia coli* by Osmolytes,Plasmid- or Benzyl Alcohol-Overexpressed Molecular Chaperones, Cell Stress and Chaperones, 2005,10 (4), pp. 329-339, Cell Stress Society International.

Gaertner, Frank H., et al., Amended recombinant cells (ARCs(TM)): An economical and surprisingly effective production and delivery vehicle for recombinant bovine IFN-y, Journal of Controlled Release, Oct. 2005, pp. 189-202, vol. 107, Elsevier B.V.

Goeddel, David V., et al., Expression in *Escherichia coli* of Chemically Synthesized Genes for Human Insulin, Proc. Natl. Acad. Sci. USA, Jan. 1979, pp. 106-110, vol. 76, No. 1.

Nakashima, Nobutaka, et al. Cell-free protein synthesis using cell extract of Pseudomonas fluorescens and CspA promoter, Biochemical and Biophysical Research Communications, Jun. 2004, pp. 671-676, vol. 319, No. 2, Elsevier.

(56) References Cited

OTHER PUBLICATIONS

Nomine, Yves, et al., Formation of Soluble Inclusion Bodies by HPV E6 Oncoprotein Fused to Maltose-Binding Protein, Protein Expression and Purification, 2001, pp. 22-32, vol. 23, Academic Press.

Retallack, Diane, et al., Pseudomonas fluorescens—a robust expression platform for pharmaceutical protein production, Microbial Cell Factories, 2006, p. S28, vol. 5 (Suppl. 1), BioMed Central.

Retallack, Diane, et al., Transport of heterologous proteins to the periplasmic space of Pseudomonas fluorescens using a variety of native signal sequences, Biotechnology Letters, 2007, pp. 1483-1491, vol. 29, Springer Science+Business Media B.V.

Supplementary European Search Report for Application No. EP 05 70 5852, Dated Mar. 18, 2008.

Vera, Andrea, et al., The Conformational Quality of Insoluble Recombinant Proteins Is Enhanced at Low Growth Temperatures, Biotechnology and Engineering, Apr. 15, 2007, pp. 1101-1106, vol. 96, No. 6.

Vincentelli, Renaud, et al., Medium-Scale Structural Genomics: Strategies for Protein Expression and Crystallization, Acc. Chem. Res., 2003, pp. 165-172, vol. 36, No. 3.

Ada, Gordon, et al., Overview of Host Defense Mechanisms with Special Reference to Viral Infections, Gamma Interferon in Antiviral Defense, 1997, Chapter 1, pp. 1-18, R.G. Landes Company.

Altschul, Stephen F., et al., Basic Alignment Search Tool, J. Mol. Biol., 1990, pp. 403-410, vol. 215.

Anderson, Kevin P., et al., Enhancement of a Secondary Anitbody Response to Vesicular Stomatitis Virus "G" Protein by IFN-y Treatment at Primary Immunization, The Journal of Immunology, 1988, pp. 3599-3604, vol. 140, No. 10, The American Association of Immunologists.

Babiuk, L.A., et al., Symposium: Immunobiology of Cytokines and Their Application in Disease Prevention in Dairy Cattle, J. Dairy Sci., 1991, vol. 74, pp. 4385-4398, Veterinary Infectious Disease Organization.

Bagdasarian, M., et al., Specific-Purpose Plasmid Cloning Vectors, II. Broad Host Range, High Copy Number, RSF1010—Derived Vectors, and a Host-Vector System for Gene Cloning in Pseudomonas, Gene, 1981, pp. 237-247, vol. 16, Elsevier/North-Holland Biomedical Press.

Bagdasarian, Michael, et al., Host: Vector Systems for Gene Cloning in Pseudomonas, Curr. Topics Microbiol. Immunol., 1982, pp. 47-67, vol. 96.

Baldwin, G.S., Comparison of Transferrin Sequences Form Different Species, Comp. Biochem. Physiol., 1993, pp. 203-218, vol. 106B. No. 1, Pergamon Press Ltd.

Broxmeyer, HE, Monocyte-Macrophage-Derived Acidic Isoferritins: Normal Feedback Regulators of Granulocyte-Macrophage Progenitor Cells In Vitro, Blood, 1982, pp. 595-607, vol. 60,. American Society of Hematology.

Carrier, M.J., et al., Expression of Human IL-1B in *Salmonella typhimurium* A Model System for the Delivery of Recombinant Therapeutic Proteins in Vivo, The Journal of Immunology, 1992, pp. 1176-1181, vol. 148, No. 4, The American Association of Immunologists.

Cerretti, Douglas Pat., et al., Cloning, Sequence, and Expression of Bovine Interferon-y, The Journal of Immunology, 1986, pp. 4561-4564, vol. 136, No. 12, The American Association of Immunologists.

Cho, Won-Kyung, et al., Production and In Vitro Refolding of a Single-Chain Antibody Specific for Human Plasma Apolipoprotein A-I, Journal of Biotechnology, 2000, pp. 169-178, vol. 77, Elsevier Science B.V.

Clark-Curtiss, Josephine, et al., Analysis of Recombinant DNA, Methods in Enzymology, 1983, pp. 347-, vol. 101, Academic Press, Inc.

Davis, Bernard D., et al., Mutants of *Escherichia coli* Requiring Methionine or Vitamin B(12), J. Bact., 1950, pp. 17-28, vol. 60.

Doudoroff, M., et al., Gram-Negative Aerobic Rods and Cocci, Bergey's Manual of Determinative Bacteriology, 1974, pp. 217-289, edited by Buchanan and Gibbons.

Dmitrij, Frishman, et al, Starts of Bacterial Genes: Estimating the Reliability of Computer Predictions, Gene, 1999, pp. 257-265, vol. 234, Elsevier Science B.V.

Fox, L.K., et al., The Effect of Interferon-y Intramammary Administration on Mammary Phagocyte Function, J. Vet. Med., 1990, pp. 28-30, Paul Parey Scientific Publishers.

Friedman, Robert M., et al., Interferons with Special Emphasis on the Immune System, Advances in Immunology, pp. 97-140, 1983, vol. 34, Academic Press Inc.

Gaertner, Frank H., CellCap: An Encapsulation System for Insecticidal Biotoxin Proteins, Advanced Engineered Pesticides, 1993, pp. 73-83, Marcel Deker, New York.

Graupner, Stefan, et al., A Broad-Host-Range Expression Vector Series Including a Ptac Test Plasmid and Its Application in the Expression of the dod Gene of Serratia Marcescens (Coding for Ribulose-5-Phosphate 3-Epimerase) in Pseudomonas Stutzeri, Biomeleular Engineering, 2000, pp. 11-16, vol. 17, Elsevier Science B.V.

Hayase, Nobuki, et al., Secretion of Human Epidermal Growth Factor (EGF) in Autotrophic Culture by a Recombinant Hydrogen-Utilizing Bacterium, Pseudomonas Psedoflava, Carrying-Broad-Host-Range EGF Secretion Vector pKSEGF2, Applied and Environmental Microbiology, Sep. 1994, pp. 3336-3342, vol. 60, No. 9, American Society for Microbiology.

Heffron, Fred, et al., Translocation of a Plasmid DNA Sequence Which Mediates Ampicillin Resistance: Molecular Nature and Specificity of Insertion, Proc. Nat. Acad. Sci., Sep. 1975, pp. 3623-3627, vol. 72, No. 9.

Holtwick, Rita, et al., A Novel Rolling-Circle-Replicating Plasmid From Pseudomonas Putida P8: Molecular Characterization and use As a Vector, Microbiology, 2001, pp. 337-344, vol. 147.

Ishii, Toshinori, et al., Elastase Gene Expression in Non-Elastase-Producing Psuedomonas Aeruginosa Strains Using Novel Shuttle Vector Systems, FEMS Microbiology Letters, 1994, pp. 307-314, vol. 116, Federation of European Microbiological Societies, pp. 307-314.

Jonathan, D. G., et al., An Efficient Mobilizable Cosmid Vector, pRK7813, and its Use in a Rapid Method for Marler Exchange in Pseudomonas Flourescens Strain HV37a, Gene, 1987, pp. 299-306, Elsevier Science Publishers B.V.

Knight Jr., E., Antiviral and Cell Growth Inhibitory Activities Reside in the Same Glycoprotein of Human Fibroblast Interferon, Nature, 1976, pp. 302-303, vol. 262, Nature Publishing Group.

Kodama, Takao, et al., The Initial Phosphate Burst in ATP Hydrolysis by Myosin and Subfragment-1 as Studied by a Modified Malachite Green Method for Determination of Inorganic Phosphate, J. Biochem. 1986, pp. 1465-1472, vol. 99.

Lawn, Richard, et al., The Sequence of Human Serum Albumin cDNA and its Expression in *E. coli*, Nucleic Acids Research, 1981, pp. 6103-6114, vol. 9, No. 22, IRL Press Limited, London.

Lee, Myung-Hoon, Bacterial Expression and in Vitro Refolding of a Single-Chain Fv Antibody Specific for Human Plasma Apolipoprotein B-100, Protein Expression and Purification, 2002, pp. 166-173, vol. 25, Elsevier Science USA.

Lofthouse, S.A., et al., Cytokines as Adjuvants for Ruminant Vaccines, International Journal of Parasitology, 1996, pp. 835-842, vol. 26, No. 8/9, Elsevier Science.

Lombillo, Vivian A., Antibodies to the Kinesin Motor Domain and CENP-E Inhibit Microtubule Depolyrnerization-Dependent Motion of Chromosomes In Vitro, The Journal of Cell Biology, 1995, pp. 107-115, vol. 182, Nos. 1 & 2, The Rockefeller University Press.

Lushnikov, A.A., et al., Shuttle Vector for *Escherichia coli*, Pseudomonas Putida, and Pseudomonas Aeruginosa, Basic Life Sci., 1985, pp. 657-662, vol. 30.

Michalski, Wojtek, et al., Recombinant Chicken IFN-y Express in *Escherichia coli*: Analysis of C-Terminal Truncation and Effect on Biologic Activity, Journal of Interferon and Cytokine Research, 1999, pp. 383-392, vol. 19, Mary Ann Liebert, Inc.

Mukhopadhyay, Pradip, et al., Construction of a Stable Shuttle Vector for High-Frequency Transformation in *Pseudomonas syringae* pv. *syringae*, Journal of Bacteriology, Jan. 1990, pp. 477-480, vol. 172, No. 1, American Society for Microbiology.

(56) References Cited

OTHER PUBLICATIONS

Morrison, D.A., Transformation in *Escherichia coli*: Cryogenic Preservation of Competent Cells, Journal of Bacteriology, Oct. 1977, pp. 349-351, vol. 132, No. 1, American Society for Microbiology.
Mukhija, Reema, et al., High-Level Production and One-Step Purification of Biologically Active Human Growth Hormone in *Escherichia coli*, Gene, 1995, pp. 303-306. vol. 165, Elsevier Scicence B.V.
Nagahari, Kenji, et al., RSF1010 Plasmid as a Potentially Useful Vector in *Pseudomonas* Species, Journal of Bacteriology, Mar. 1978, pp. 1527-1529, vol. 133, No. 3, American Society for Microbiology.
Needleman, Saul B., et al., A General Method Applicable to the Search for Similarities in the Amino Acid Sequence of two Proteins, J. Mol. Biol., 1970, pp. 443-453, vol. 48.
Nielsen, Henrik, et al., Short Communication, Identification of Prokaryotic and Eukaryotic Signal Peptides and Prediction of their Clevage Sites, Protein Engineering 1997, pp. 1-6, vol. 10, No. I, Oxford University Press.
Nieto, C., et al., Cloning Vectors, Derived From a Naturally Occurring Plasmid of Psedomonas Savastanoi, Specifically Tailored for Genetic Manipulation in Psedoomonas, Gene, 1990, pp. 145-149, vol. 87, Elsevier.
Olekhnovich, Igor N., et al., Controlled-Expression Shuttle Vector for Pseudomonads Based on the trpIBA genes of Pseudomonas Putida, Gene, 1994, pp. 63-65, vol. 140, Elsevier Science.
Opdenakker, G., et al., Interaction of Interferon With Other Cytokines, Experientia, 1989, pp. 513-520, vol. 45, Birkhauser Verlag, Switzerland.
PCT International Search Report for Application PCT/US05/01549, mailed Jul. 19, 2005.
Patra, Ashok K., et al., Optimization of Inclusion Body Solubilization and Renaturation of Recombinant Human Growth Hormone from *Esherichia coli*, Protein Expression and Purification, 2000, pp. 182-192, vol. 18, Academic Press.
Pearson, William R., et al., Improved Tools for Biological Sequence Comparison, Proc. Natl. Acad. Sci., Apr. 1988, pp. 2444-2448, vol. 85.
Perussia, Bice, et al., Immune Interferon Induces the Receptor for Monomeric IgG1 on Human Monocytic and Myeloid Cells, J. Exp. Med., 1983, pp. 1092-1113, vol. 158, Rockefeller University Press.
Pestka, Sidney, et al., Interferons and Their Actions, Arum Rev. Biochem., 1987, pp. 727-777, vol. 56, Annual Reviews, Inc.
Pighetti, Gina M., et al., Specific Immune Responses of Dairy Cattle After Primary Inoculation with Recombinant Bonvine Interferon-y as an Adjuvant When Vaccinating Against Mastitis, American Journal of Veterinary Research, 1996, pp. 819-824, vol. 57, No. 6.
Ralph, Peter, Human B Cell-Inducing Factor(s) for Production of IgM, IgG and IgA; Independence From IL 2(1), The Journal of Immunology, Apr. 1984, pp. 1858-1862, vol. 132, No. 4, The American Society of Immunologists.
Riesenberg, D., et al., High Cell Density Cultivation of *Escherichia coli* at Controlled Specific Growth Rate, Journal of Biotechnology, 1991, pp. 17-28, vol. 20, Elsevier Science Publishers, B.V.
Saiki, Osamu, et al., Induction of Human Immunoglobulin Secretion I. Synergistic Effect of B Cell Mitogen Cowan 1 Plus T Cell Mitogens or Factors, The Journal of Immunology, Sep. 1981, pp. 1044-1047, vol. 127, No. 3, The American Association of Immunologists.
Steidler, L., et al., Mucosal Delivery of Murine Interleukin-2 (IL-2) and IL-6 by Recombinant Strains of Lactococcus Lactis Coexpressing Antigen and Cytokine, Infection and Immunity, 1998, pp. 3183-3189, vol. 66, No. 7.
Steinbeck, M.J., et al., Activation of Bovine Neutrophils by Recombinant Interferon-y, Cell. Innnunol., 1986, pp. 137-144, vol. 98.
Stewart, Russell J., et al., Direction of Microtubule Movement is an Intrinsic Property of the Motor Domains of Kinesin Heavy Chain and *Drosophila* Ned Protein, Proc. Natl. Acad. Sci., 1993, pp. 5209-5213, vol. 90.
Suzek, Baris E., et al., A Probalistic Method for Identifying Start Codons in Bacterial Genomes, Bioinformatics, 2001, pp. 1123-1130, vol. 17, No. 12, Oxford University Press.
Tsuda, Masataka, et al., A Mutagenesis System Utilizing a Tn1722 Derivative Containing an *Escherichia coli*-Specific Vector Plasmid: Application to *Pseduomonas* Species, Gene, 1993, pp. 257-262, vol. 136, Elsevier Science Publisher B.V.
Vale, Ronald D., et al., Identification of a Novel Force-Generating Protein, Kinesin, Involved in Microtubule-Based Motility, Cell, Aug. 1985, pp. 39-50, vol. 42, MIT.
Vinogradov, Alexi A, et al., Solubilization and Refolding of Inclusion Body Proteins in Reverse Micelles, Analytical Biochemistry, 2003, pp. 234-238, vol. 320, Elsevier Science.
Waterman, Michael S., Comparison of Biosequences, Advances in Applied Mathematics, 1981, pp. 482-489, vol. 2, Academic Press, Inc.
Wood, David O., et al., Versatile Cloning Vector for Pseudomonas Aeruginosa, Journal of Bacteriology, Mar. 1981, pp. 1448-1451, vol. 14, No. 3.
Yang, Funmei, et al., Human Transferrin: cDNA Characterization and Chromosomal Localization, Proc. Natl. Acad. Sci. USA, May 1984, pp. 2752-2756, vol. 81.
Yilma T., et al., Enhancement of Primary and Secondary Immune Responses by Interferon-Gamma, Adv. Exp. Med. Biol., 1989, pp. 145-152, vol. 251.
Yip, Y.K., et al., Purification and Structural-Functional Characterization of Human Immune Interferon, J. Biol. Chem. 1984, p. p. 283, vol. 3.
Zuffa, A., et al., Protection of Cattle Vaccinated with Inactivated Oil-Adjuvant Infectious Bovine Rhino Trachetis Vaccine Against Experimental Infection, Zbl. Vet. Med. G., 1989, pp. 725-733, vol. 27.
Casavant et al., "Use of a site-specific recombination-based biosensor for detecting bioavailable toluene and related compounds on roots," Environmental Microbiology 5(4):238-249 (2003).
De Marco et al., "Native Folding of Aggregation-Prone Recombinant Proteins in *Escerichia coli* by Osmolytes, Plasmid—or—Benzyl Alcohol-Overexpressed Molecular Chaperones," Cell Stress and Chaperones 10(4):329-339 (2005).
Landry et al., "Safety evaluation of an a-anylase enzyme preparation derived from the archaeal order Thermococcales as expressed in Pseudomonas fluorescens biovar 1," Regulatory Toxicology and Pharmacology 37:149-168 (2003).
Nakashima et al., "Cell-free protein synthesis using cell extract of Pseudomonas fluorescens and CspA promoter," Biochem Biophys Res. Comm. 319(2):671-676 (2004).
Nomine et al., "Formatio of Soluble Inclusion Bodies by HPV E6 Oncoprotein Fused to Maltose-Binding Protein," Protein Expression and Purification 23:22-23 (2001).
Retallack et al., "Pseudomonas fluorescens—a robust expression platform for pharmaceutical protein production," Microbial Cell Factories 5(Suppl. 1):S28 (2006).
Retallack et al., "Transport of heterologous proteins to the periplasmic space of Pseudomonas fluorescens using a variety of native signal sequences," Biotech. Lett. 29:1483-1491 (2007).
EP 05705852 Supplementary EP Search Report dated Mar. 18, 2008.
Vera et al., "The Conformational Quality of Insoluble Recombinant Proteins is Enhanced at Low Growth Temperatures," Biotech. Eng. 96(6):1101-1106 (2007).
Vincentelli et al., "Medium-Scale Structural Genomics: Strategies for Protein Expression and Crystallization," Acc. Chem. Res. 36(3):165-172 (2003).
Gellison, ed. Production of Recombinant Proteins. Novel Microbial and Eukaryotic Expression Systems, Wiley-VCH 2005, pp. 47-48.
Thomas, J.G., et al., "Molecular chaperones, folding catalysts and the recovery of active recombinant proteins from *E. coli*: to fold or to refold," 1997, Appl Biochem Biotechnol 66, pp. 197-238.
Baneyx, F. and G. Georgiou, "Construction and Characterization of *Escherichia coil* Strains Deficient in Multiple Secreted Proteases: Protease III Degrades High-Molecular-Weight Substrates In Vivo," 1991, J. Bacterial., pp. 2696-2703, vol. 173, No. 8.

(56) References Cited

OTHER PUBLICATIONS

Abdullah, et al., "System-48" high-throughput cloning and protein expression analysis, Methods Mol Biol 498:117-127 (2009).
Akao, et al., "Purification and Characterization of a Peptide Essential for Formation of Streptolysin S by *Streptococcus pyogenes*," 1992, Infection and Immunity 60(11):4777-4780.
Amitani, et al., "Purification and Characterization of Factors Produced by *Aspergillus fumigatus* Which Affect Human Ciliated Respiratory Epithelium," 1995, Infection and Immunity 63 (9):3266-3271.
Aricescu, et al., "A time- and cost-efficient system for high-level protein production in mammalian cells," 2006, Acta Cryst D62:1243-1250.
Aricescu, et al., "Eukaryotic expression: developments for structural proteomics," Acta Cryst D62:1114-1124 (2006).
Bahia, et al., "Optimisation of insect cell growth in deep-well blocks: development of a high-throughput insect cell expression screen," 2005, Protein Expression and Purification 39:61-70.
Baldwin, et al., "Subunit Vaccine against the Seven Serotypes of Botulism," 2008, Infection and Immunity 76(3):1314-1318.
Bebbington and Yarranton, "Antibodies for the treatment of bacterial infections: current experience and future prospects," 2008, Curr Op Biotech 19(6):613-619.
Boettner, et al., "High-throughput screening for expression of heterologous proteins in the yeast *Pichia pastoris*," 2002, J Biotech 99:51-62.
Buzzi, et al., "CRM197: reduction of atherosclerosis stenoses in carotids of three elderly patients," Therapy 4(3):293-298 (2007).
Calvete, et al., "The disulfide bond pattern of catrocollastatin C, a disintegrin-like/cysteine-rich protein isolated from *Crotalus atrox* venom," Protein Science 2000, 9:1365-1373.
Damasceno, et al., "Cooverexpression of chaperones for enhanced secretion of a single-chain antibody fragment in *Pichia pastoris*," 2007, Appl Microbiol Biotechnol 74:381-389.
Duetz and Witholt, "Oxygen transfer by orbital shaking of square vessels and deepwell microtiter plates of various dimensions," 2004, Biochem Eng J 17:181-185.
Duetz, et al., "Methods for Intense Aeration, Growth, Storage, and Replication of Bacterial Strains in Microtiter Plates," 2000, Appl Env Microbiol 66(6):2641-2646.
Edmond, et al., "Optimized and Automated Protocols for High-Throughput Screening of Amylosucrase Libraries," 2007, J Biomol Screen 12:715-723.
Fang et al., "Development of a high-throughput yeast two-hybrid screening system to study protein-protein interactions in plants," 2002, Mol Genet Genomics 267:142-153.
Fischer and Montal, "Crucial Role of the Disulfide Bridge between Botulinum Neurotoxin Light and Heavy Chains in Protease Translocation across Membranes," 2007, Biol Chem 282(40):29604-29611.
Georgopoulos, Costa, "Toothpicks, Serendipity and the Emergence of the *Escherichia coil* DnaK (Hsp70) and GroEL (Hsp60) 2006, Chaperone Machines," Genetics 174:1699-1707.
Giannini G., et al., "The amino-acid sequence of two non-toxic mutants of diphtheria toxin: CRM45 and CRM197," 1984, Nucl Acids Res 12(10):4063-4069.
Gonzalez Barrios et al., "Autoinducer 2 Controls Biofilm Formation in *Escherichia coli* through a Novel Motility Quorum-Sensing Regulator (MqsR, B3022)," 2006, J Bacteriol 188:305-316.
Halling, K., et al., "Genomic cloning and characterization of a ricin gene from *Ricinus communis*," 1985, Nucl Acids Res 13(22):8019-8033.
Holz, et al., "A micro-scale process for high-throughput expression of cDNAs in the yeast *Saccharomyces cerevisiae*," 2002, Protein Expression and Purification 25:372-378.
Hsu, et al., "Engineering the Assembly Pathway of the Baculovirus-Insect Cell Expression System." 1994, Annals New York Academy of Sciences 721:208-217.
Jarvis, et al., "Influence of Different Signal Peptides and Prosequences on Expression and Secretion of Human Tissue Plasminogen Activator in the Baculovirus System," 1993, J Biol Chem 268:pp. 16754-16762.
Kim, W., et al., "Glycosyltransferase—a specific marker for the discrimination of *Bacillus anthracis* from the *Bacillus cereus* group," 2008, J. Med Microbiol 57:279-286.
Larsen, et al., "Expression of *Candida antarctica* lipase B in *Pichia pastoris* and various *Escherichia coli* systems," 2008, Protein Expression and Purification 62:90-97.
Makarenkova, et al., "Dendritic cells and natural killer cells interact via multiple TNF family molecules," J Leukocyte Biol 77:408-413 (2005).
Mitamura, et al., "Diphtheria Toxin Binds to the Epidermal Growth Factor (EGF)-like Domain of Human Heparin-binding EGF-like Growth Factor/Diphetheria Toxin Receptor and Inhibits Specifically Its Mitogenic Activity," J Biol Chem 270(3):1015-1019 (1995).
Montgomerie, et al., "Improving the accuracy of protein secondary structure prediction using structural alignment," BMC Bioinformatics 7:301 (2006).
Naamati, et al., "ClanTox: a classifier of short animal toxins," 2009, Nucleic Acids Research 37, Web Server issue W363 -W368; doi:10.1093/nar/gkp299.
Niwa, et al., "Bimodal protein solubility distribution revealed by an aggregation analysis of the entire ensemble of *Escherichia coli* proteins," PNAS 106(11):4201-4206 (2009).
Novak, et al., "Bacterial growth properties at low optical densities," Antonie Van Leeuwenhoek 96(3):267-274 (2009).
Orr, et al., "Expression and Immunogenecity of a Mutant Diphtheria Toxin Molecule, CRM 197, and Its Fragments in *Salmonella typhi* Vaccine Strain CVD 908-htrA," Infection and Immunity 67(8):4290-4294 (1999).
Papini, et al., "Cell Penetration of Diphtheria Toxin," J Biol Chem 268(3):1567-1574 (1993).
Randolph, et al., "Amino acid sequence of fibrolase, a direct-acting fibrinolytic enzyme from Agkistrodon contortrix contortrix venom," Protein Science 1:590-600 (1992).
Schiavo, et al., "An intact interchain disulfide bond is required for the neurotoxicity of tetanus toxin," 1990, Infection and Immunity 58(12):4136-4141.
Shu, et al., "The structure of spider toxin huwentoxin-II with unique disulfide linkage: Evidence for structural evolution," Protein Science 11:245-252 (2002).
Smialowski, et al., "Protein solubility: sequence based prediction and experimental verification," Bioinformatics 23(19):2536-2542 (2007).
Tsai and Rapoport, "Unfolded cholera toxin is transferred to the ER membrane and released from protein disulfide isomerase upon oxidation by Ero1," J Cell Biol 159(2):207-215 (2002).
Tsunawaki, et al., "Fungal Metabolite Gliotoxin Inhibits Assembly of the Human Respiratory Burst NADPH Oxidase," Infection and Immunity 72 (6):3373-3382 (2004).
Usami, et al., "Primary structure of two-chain botrocetin, a von Willebrand factor modulator purified from the venom of *Bothrops jararaca*," PNAS USA 90:928-932 (1993).
Vad, et al., "Engineering of a Pichia pastoris expression system for secretion of high amounts of intact human parathyroid hormone," J Biotechnology 116:251-260 (2005).
Yuan, et al., "Discovery of a Distinct Superfamily of Kunitz-Type Toxin (KTT) from Tarantulas," PLoS One 3(10):e3414 (2008).
Zhang, et al., "Enhanced Secretion of Heterologous Proteins in Pichia pastoris Following Overexpression of *Saccharomyces cerevisiae* Chaperone Proteins," Biotechnol Prog 22:1090-1095 (2006).
Wall, G.J. and Pluckthun, A., "Effects of Overexpressing Folding Modulators on the in vivo Folding of Heterologous Proteins in *Escherichia coli*," Curr. Op. Biotechnol. 6:507-516 (1995).
Wu, et al., "Cell-biological applications to transfected-cell microarrays," (2002) Trends in Cell Biology, 12(10): 485-488.
Akao, et al., "Unique synthetic peptides stimulating streptolysin S production in streptococci," 1999, J. Biochem. 125(1):27-30.

(56) References Cited

OTHER PUBLICATIONS

Ames, et al., "Simple, Rapid, and Quantitative Release of Periplasmic Proteins by Chloroform." 1984, J. Bacteriol., 160(3): pp. 1181-1183.

Andersen, D.C. et al., "Production technologies for monoclonal antibodies and their fragments." Current Opinion in Biotechnology, London, GB, vol. 15, No. 5, Oct. 1, 2004, pp. 456-462.

Anderson, et al., 1997, "A homologue of the TNF receptor and its ligand enhance T-cell growth and dendritic-cell function," Nature 390 (6656), 175-179.

Appa Rao, et al., "High-Level Expression of Ovine Growth Hormone in *Escherichia coli*: Single-Step Purification and Characterization," Protein Expr Purif, 1997, vol. 1, No. 2, pp. 201-208.

Ariga, et al., "Release of Thermophilic α-amylase from Transformed *Escherichia coli* by Addition of Glycine," 1989, J. Ferm. Bioeng., 68:243-246.

Arthur, et al., High Level expression of interleukin-1beta in a recombinant *Escherichia coli* strain for use in a controlled bioreactor, Journal of Biotechnology, Elsevier Science Publishers, 1990, vol. 13, No. 1, pp. 29-46.

Asai, et al., "DNA micro array analysis of *Bacillus subtilis* sigma factors of extracytoplasmic function family," 2003, FEMS Microbiol. Ltrs. 220(1):155-160.

Asami, et al., "Synchronized disruption of *Escherichia coli* cells by T4 Phage Infection," 1997, J. Ferment and Bioeng., 83: pp. 511-516.

AU Patent Application 2008245696 Office Action issued Oct. 24, 2012.

AU Patent Application 2005269527 Office Action issued Nov. 3, 2010.

AU Patent Application 2005206951 Office Action issued Jan. 16, 2009.

Baldwin, G.S., Comparison of Transferrin Sequences From Different Species. 1993, Comp. Biocherm Physiol., pp. 203-218, vol. 106B. No. 1, Pergamon Press Ltd.

Baneyx, Francois, "Recombinant protein expression in *Escherichia coli*." 1999, Curr. Op. Biotech. 10:411-421.

Bardwell, et al. "Pathways of Disulfide Bond Formation in Proteins in Vivo." 1994, Phosphate Microorg. Chapter 45, pp. 270-275.

Davis and ES Mingioli, "Mutants of *Escherichia coli* Requiring Methionin or Vitamin B12," (1950) J. Bact. 60:17-28.

Bellini, et al., "Production processes of recombinant IL-1beta from Bacillus subtilis: comparison between intracellular and exocellular expression," Journal of Biotechnology, Elsevier Science, 1991, vol. 18, No. 3, pp. 177-192.

Benoist & Chambon, "In vivo sequence requirements of the SV40 early promoter region," (1981) Nature 290:304-310.

Berrow, N.S. et al., "Recombinant protein expression and solubility screening in *Escherichia coli*: a comparative study," 2006, Biological Crystallography. 62: 1218-1226.

Blattner, et al., "The Complete Genome Sequence for *Escherichia coli* K-12." 1997, Science 277 (5331): 1453-74.

Bohnsack, R.N., "Site-directed mutagenesis using positive antibiotic selection," 1996, Meth. Mol. Biol. 57,1-12.

Foss, FM, 2001, "Interleukin-2 fusion toxin: targeted therapy for cutaneous T cell lymphoma," Ann N Y Acad Sci. 941:166-76.

Broxmeyer, H.E., Monocyte-Macrophage-Derived Acidic Isoferritins: Nomal Feedback Regulators of Granulocyte-Macrophage Progenitor Cells In Vitro, Blood, 1982, pp. 595-607, vol. 60, American Society of Hematology.

Butte, A., "The use and analysis of microarray data," 2002, Nat Rev Drug Discov 1:951-60.

Canadian Patent Application CA2553503 Exam Report dated May 10, 2011.

Canadian Patent Application CA2574953 Office Action dated Jun. 27, 2012.

Carrier, M.I., et al., Expression of Human IL-1B in *Salmonella typhimurium* A Model System for the Delivery of Recombinant Therapeutic Proteins in Vivo, The Journal of Immunology, 1992, pp. 1176-1181, vol. 148, No. 4, The American Association of Immunologists.

Cerretti, Douglas Pat., et al., Cloning, Sequence, and Expression of Bovine Interferon-γ, The Journal of Immunology, 1986, pp. 4561-4564, vol. 136, No. 12, The American Association of Immunologists.

Chalfie, et al., "Green fluorescent protein as a marker for gene expression," 1994, Science 263(5148):802-805.

Chang and Cohen, "Construction and Characterization of Amplifiable Multiopy DNA Cloning Vehicles Derived from the P15A Cryptic Miniplasmid," 1978, Journal of Bacteriology, vol. 134, No. 3, p. 1141-1156.

Chew, et al., "Production of Recombinant Proteins. Novel Microbial and Eucaryotic Expression Systems," 2005, G. Gellissen, Weinheim, Wiley-VCH: 45-66.

Cho, Won-Kyung, et al., "Production and In Vitro Refolding of a Single-Chain Antibody Specific for Human Plasma Apolipoprotein A-I," Journal of Biotechnology, 2000, pp. 169-178, vol. 77, Elsevier Science B.V.

Clark-Curtiss, Josepiiine, et al., "Analysis of Recombinant DNA Using *Escherichia coli* Minicells," Methods in Enzymology, 1983, vol. 101, pp. 347-362, Academic Press, Inc.

CN200580032245 Office Action dated Apr. 12, 2012.

CN200880022208 Secord Office Action dated Jul. 16, 2012.

Cosman, "A Family of Ligands for the TNF Receptor Superfamily," Stem Cells, 1994: 12:440-455.

Dabora and Cooney, "Intracellular lytic enzyme systems and their use for disruption of *Escherichia coli*," 1990, Advances in Biochemical Engineering/Biotechnology, vol. 43, A. Fiechter, ed. (Springer-Verlag: Berlin), pp. 11-30.

De Marco, Ario, et al., Native folding of aggregation-prone recombinant proteins in *Escherichia coli* by osmolytes, plasmid- or benzyl alcohol-overexpressed molecular chaperones, 2005, Cell Stress and Chaperones, 10(4), pp. 329-339, Cell Stress Society International.

Deng, W.P. and Nickoloff, J.A., "Site-directed mutagenesis of virtually any plasmid by eliminating a unique site," (1992) Anal. Biochem. 200, 81.

Doudoroff, M., et al., Gram-Negative Aerobic Rods and Cocci, 1974, Bergey's Manual of Determinative Bacteriology, pp. 217-289, edited by Buchanan and Gibbons.

Dulebohn, D., "Trans-Translation: The tmRNA-Mediated Surveillance Mechanism for Ribosome Rescue, Directed Protein Degradation, and Nonstop mRNA Decay," Biochemistry, 2007, 46 (16): 4681-4693.

Elbashir et al., "Duplexes of 21-nucleotide RNAs mediate RNA interference in cultured mammalian cells," 2001, Nature 411(6836): 494-8.

Elbashir et al., "RNA interference is mediated by 21-and 22-nucleotide RNAs," (2001) Genes & Development 15(2):188-200.

EP05705852 European Search Report dated Oct. 5, 2011.
EP05774619 Examination Report dated Oct. 29, 2010.
EP05774619 International Search Report dated Apr. 4, 2009.
EP08746833.6 Exam Report dated Feb. 15, 2012.
EP11173331.7 Extended search report dated Apr. 18, 2012.
EP11173331.7 Partial Search Report dated Dec. 27, 2011.
EP11176612 Extended European Search Report dated Jul. 18, 2012.
EP11176612 Partial European Search Report dated Jan. 25, 2012.
EP11173331.7 Examination Report issued Dec. 19, 2012.

Espejo, A., "Protein-domain microarrays Processes." 2004, Mol Biol., 264:173-81.

Eymann C., et al., "*Bacillis subtilis* Functional Genomics: Global Characterization of the Stringent Response by Proteome and Transcriptome Analysis," 2002, J Bacteriol 184(9), pp. 2500-2520.

Fathallah-Shaykh, H.M., "Microarrays: applications and pitfalls," 2005, Arch. Neurol. 62(11):1669-1672.

Fire, A. et al., "Potent and specific genetic interference by double-stranded RNA in Caenorhabdtis elegans." 1998, Nature 391:806-11.

Fransen, Lucie, et al., Recombinant Tumor Necrosis Factor: Species Specificity for a Variety of Human and Murine Transformed Cell Lines, Cellular Immunology, 1986, pp. 260-267, vol. 100, Academic Press, Inc.

Frishman, Dmitrij, et al., Starts of bacterial genes: estimating the reliability of computer predictions, Gene, 1999, pp. 257-265, vol. 234, Elsevier Science B.V.

(56) References Cited

OTHER PUBLICATIONS

Gaertner, Frank H., et al., Amended recombinant cells (ARCs(TM)): An economical and surprisingly effective production and delivery vehicle for recombinant bovine IFN-γ, Journal of Controlled Release, Oct. 2005, pp. 189-202, vol. 107, Elsevier B.V.
Gardiner, et al., "Bioinformatic and expression analysis of the putative gliotoxin biosynthetic gene cluster of Aspergillus fumigatus," 2005, FEMS Microbiol. Lett. 248(2):241-248.
Gellison, ed. Production of Recombinant Proteins, Novel Microbial and Eukaryotic Expression Systems, Wiley-VCH 2005, pp. 47-48.
Gene Ontology Consortium 2004. The Gene Ontology (GO) database and informatics resource. Nucleic Acids Research 32: D258-D261.
Georgiou, et al., "Preparative expression of secreted proteins in bacteria: status report and future prospects," 2005, Current Opinion in Biotechnology; vol. 16, pp. 538-545.
Gill, et al., "Genomic Analysis of High-Cell-Density Recombinant *Escherichia coli* Fermentation and "Cell Conditioning" for Improving Recombinant Protein Yield," 2001, Biotech. Bioengin 72, pp. 85-95.
Goeddel, et al., "Expression in *Escherichia coli* of chemically synthesized genes for human insulin," Jan. 1979, Proc. Nat. Acad. Sci. USA, vol. 76, No. 1, pp. 106-110.
Gottesman, Susan, "Proteases and their Targets in *Escherichia coli*," 1996, Annu. Rev. Genet 30, pp. 465-506.
Gough, R.E., et al., Further Studies on the Adjuvant Effect of an Interferon Inducer (BRL 5907) on Newcastle Disease and Avian Influenza Inactivated Vaccines, Research in Veterinary Science, 1975, pp. 185-188, vol. 19.
Graupner, S. & Wackernagel, W., "A broad-host-range expression vector series including a Ptac test plasmid and its application in the expression of the *dod* gene of *Serratia marcescens* (coding for ribulose-5-phosphate 3-epimerase) in *Pseudomonas stutzeri*," 2000, Biomolecular Engineering, pp. 11-16, vol. 17, Elsevier Science B.V.
Gray, et al. "Pseudomonas Aeruginosa Secretes and Correctly Processes Human Growth Hormone," (Bio/Technology, Feb. 1984, pp. 161-165).
Greenfield, L., et al., "Nucleotide sequence of the structural gene for diphtheria toxin carried by corynebacteriophage beta," 1983, Proc. Natl. Acad. Sci. USA, 80(22):6853-6857.
Gresser, Ion, et al., Anti-Tumor Effects of Interferon in Mice Injected with Interferon Sensitive and Interferon-Resistant Friend Leukemia Cells. VI. Adjuvant Therapy After Surgery in the Inhibition of Liver and Spleen Metastases, Int. J. Cancer, 1987, pp. 789-792, vol. 39, Alan R. Liss, Inc.
Gruss, P., et al., "Simian virus 40 tandem repeated sequences as an element of the early promoter." 1981, Proc. Nat. Acad. Sci. USA 78:943-947.
Gubler, U., et al., "Recombinant Human Interleukin 1-Alpha Purification and Biological Characterization," Journal of Immunology, 1986, vol. 136, No. 7, pp. 2492-2497.
Guzman, M., et al., "Tight Regulation, Modulation and High-Level Expression by Vectors Containing the Arabinose PBAD Promoter," 1995, Journal of Bacteriology 177(14):4121-30.
Gygi, et al., "Quantitative analysis of complex protein mixtures using isotope-coded affinity tags," Nat. Biotech, Oct. 1999, 17:994-999.
Hamilton, et al., "New Method for generating deletions and gene replacements in *Escherichia coli*," 1989, Journal of Bacteriology 171(9): 4617-4622.
Han, et al., "Engineering *Escherichia coli* for Increased Productivity of Serine-Rich Proteins Based on Proteome Profiling," 2003, Applied Env. Microbiol. 69(10):5772-5781.
Heffron, F., et al., "Translocation of a plasmid DNA sequence which mediates ampicillin resistance: Molecular nature and specificity of Insertion," Sep. 1975, Proc. Nat. Acad. Sci., pp. 3623-3627, vol. 72, No. 9.
Heim and Tsien, "Engineering green fluorescent protein for improved brightness, longer wavelengths and fluorescence resonance energy transfer," (1996) Curr. Biol. 6:178-182.
Herman, C., et al ., "Degradation of carboxy-terminal-tagged cytoplasmic proteins by the *Escherichia coli* protease HflB (FtsH)," 1998, Genes Dev 12, pp. 1348-1355.
Hochuli, Erich, "Purification of Recombinant Proteins with Metal Chelate Absorbent," 1990, Genetic Engineering, vol. 12, pp. 87-91.
Hockney, Robert C., "Recent developments in heterologous protein production in *Escherichia coli*." 1994, Trends Bio Technology, 12: pp. 456-463.
Holliday, R., "A Mechanism for Gene Conversion in Fungi," Genet Res. 5:282 (1964).
Holtwick, R., et al., "A novel rolling-circle-replicating plasmid from Pseudomonas putida P8: molecular characterization and use as a vector," 2001, Microbiology, vol. 147, Pt. 2, pp. 337-344.
Horton, et al., "Gene splicing by overlap extension: tailor-made genes using the polymerase chain reaction," 1990, Bio Techniques 8(5): 528-30, 532, 534-5.
Hsieh, et al., "Pairing of homologous DNA sequences by proteins: evidence for three-stranded DNA," 1990, Genes & Development 4: 1951-1963.
Ikehata, O., et al., Primary structure of nitrite hydratase deduced from the nucleotide sequence of a *Rhodococcus* species and its expression in *Escherichia coli*, 1989, Eur. J. Biochem, pp. 563-570, vol. 181.
Indian Patent Application 523/DELNP/07 Office Action issued Sep. 6, 2012.
Ishii, T., et al., Elastase gene expression in non-elastase-producing *Pseudomonas* aeruginosa strains using novel shuttle vector systems, 1994, FEMS Microbiology Letters, pp. 307-314, vol. 116, Federation of European Microbiological Societies, pp. 307-314.
Japanese Patent Application 2006-549690 Office Action mailed Sep. 11, 2012.
Japanese Patent Application 2007-523707 Office Action dated May 17, 2011.
Japanese Patent Application 2010-0506503 Office Action dated Jun. 5, 2012.
Jin, H., et al., "Soluble periplasmic production of human granulocyte colony-stimulating factor (G-CSF) in *Pseudomonas fluorescens*." 2011, Protein Expression and Purification, vol. 78, No. 1, pp. 69-77.
Jones, Jonathan D.G., et al., An Efficient Mobilizable Cosmid Vector, pRK7813, and its Use in a Rapid Method for Markler Exchange in Pseudomonas Flourescens Strain HV37a, Gene, 1987, pp. 299-306, Elsevier Science Publishers B.V.
Joseph-Liazun, et al., "Human recombinant interleukin-1β isolated from *Escherichia coli* by simple osmotic shock," 1990, Gene 86:291-295.
Kabir, et al., "Gene expression patterns for metabolic pathway in *pgi* knockout *Escherichia coli* with and without *phb* genes based on RT-PCR," 2003, J. Biotech. 105(1-2):11-31.
Kaster, K.R., et al., "Analysis of a bacterial hygromycin B resistance gene by transcriptional and translational fusions and by DNA sequencing," 1983, Nucleic Acids Res. (19):6895-911.
Khoury, G. and Gruss, P., "Enhancer Elements," 1983, Cell, vol. 33:313-314.
Knight, et al., Construction and initial characterization of a mouse-human chimeric anti-TNF antibody. Mol Immunol. Nov. 1993; 30(16):1443-53.
Kodama, T., et al., "The Initial Phosphate Burst in ATP Hydrolysis by Myosin and Subfragment-1 as Studied by a Modified Malachite Green Method for Determination of Inorganic Phosphate." 1986, J. Biochem. pp. 1465-1472, vol. 99.
Korean Patent Application 10-2006-7014191 Office Action dated Apr. 24, 2012.
Korean Patent Application 10-2006-7014191 Office Action dated Sep. 8, 2011 (English Translation only).
Korean Patent Application 10-2007-7004418 Final Rejection dated Sep. 11, 2012.
Korean Patent Application 10-2007-7004418 Exam Report dated Dec. 22, 2011.
Korean Patent Application 10-2007-7004418 Exam Report dated Nov. 26, 2012.
Korean Patent Application 10-2012-7013463 Office Action dated Sep. 2, 2012 (Office action in Korean only).

(56) References Cited

OTHER PUBLICATIONS

Kumar, et al., "The highly efficient productions of full-length and mutant rat brain calcium-binding proteins (calbindins-28K) in a bacterial expression system," Arch Biochem Biophys, 1994, vol. 308, No. 1, pp. 311-317.

Landry, T., et al., "Safety evaluation of an α-amylase enzyme preparation derived from the archaeal order *Thermococcales* as expressed in *Pseudomonas fluorescens* biovar I," 2003, Regulatory Toxicology and Pharmacology, vol. 37, pp. 149-168, see whole article, particularly pp. 151-152.

Lawn, R., et al., "The sequence of human serum albumin cDNA and its expression in *E. coli*," 1981, Nucleic Acids Research, pp. 6103-6114, vol. 9, No. 22, IRL Press Limited, London.

Lee, S., et al., "Effect of Overproduction of Heat Shock Chaperones GroESL and DnaK on Human Procollagenase Production in *Escherichia coli*," 1992, Journal of Biological Chemistry vol. 267, No. 5, pp. 2849-2852.

Lee, M.H., "Bacterial Expression and in Vitro Refolding of a Single-Chain Fv Antibody Specific for Human Plasma Apolipoprotein B-100," 2002, Protein Expression and Purification, pp. 166-173, vol. 25, Elsevier Science USA.

Lewis, M.K. and Thompson, D.V., "Efficient site directed in vitro mutagenesis using ampicillin selection," 1990, Nucl. Acids Res. 18, No. 12, pp. 3439-3443.

Lockhart, et al., "Expression monitoring by hybridization to high-density oligonucleotide arrays," 1996, Nat Biotechnol 14:1675-80.

Lombardo, et al, "*Escherichia coli* PapD in Guidebook to Molecular Chaperones and Protein Folding Catalysts," Gething M-J Ed. Oxford University Press Inc. New York. 1997, pp. 463-465.

Lombillo, Vivian A., Antibodies to the Kinesin Motor Domain and CENP-E Inhibit Microtubule Depolymerization-dependent Motion of Chromosomes In Vitro, 1995, The Journal of Cell Biology, pp. 107-115, vol. 128, Nos. 1 & 2, The Rockefeller University Press.

Lundell, et al., "Cytoplasmic and periplasmic expression of a highly basic protein, human interleukin 4, in *Escherichia coli*," 1990, J. Indust. Microbio. 5: pp. 215-228.

Lushnikov, A.A., et al., "Shuttle Vector for *Escherichia coli, Pseudomonas putida*, and *Pseudomonas aeruginosa*," 1985, Basic Life Sci., pp. 657-662, vol. 30.

MacBeath, G. & Schreiber, SL, "Printing proteins as microarrays for high-throughput function determination," 2000, Science 289:1760-1763.

Magnan, et al., SOLpro: accurate sequence-based prediction of protein solubility, 2009, Bioinformatics 25(17): 2200-2207.

Manoil, Colin, "Tagging Exported Proteins Using *Escherichia coli* Alkaline Phosphatase Gene Fusions," 2000, Methods in Enzymol. 326: 35-47.

Martineau, Pierre, et al., Expression of an Antibody Fragment at High Levels in the Bacterial Cytoplasm, J. Mol. Biol., 1998, pp. 117-127, vol. 280, Academic Press.

McCarthy, et al., (1990) "Translational Control of Prokaryotic Gene Expression," Trends in Genetics 6:78-85.

Mezghani-Abdelmoula, et al., "Invasive Behavior and Depolarization Effect of Pseudomonas Fluorescens on Rat Cerebellar Granule Neurons," African Journal of Clinical and Experimental Microbiology, Jan. 2005, pp. 1-13).

Michalski, Wojtek, et at., Recombinant Chicken IFN-y Expressed in *Escherichia coli*: Analysis of C-Terminal Truncation and Effect on Biologic Activity, Journal of Interferon and Cytokine Research, 1999, pp. 383-392, vol. 19, Mary Ann Liebert, Inc.

Miksch, G., et al., "The kil gene of the ColE1 plasmid of *Escherichia coli* controlled by a growth-phase-dependant promoter mediates the secretion of a heterologous periplasmic protein during the stationary phase," 1997 Arch. Microbiol. 167:143-150.

Mukhija, Reema, et at., High-Level Production and One-Step Purification of Biologically Active Human Growth Hormone in *Escherichia coli*, Gene, 1995, pp. 303-306. vol. 165, Elsevier Science B.V.

Mulder, et al., "InterPro, progress and status in 2005," Nucleic Acids Res., 2005, 33, Database Issue: D201-5.

Nagahari, Kenji, et al., "RSF1010 Plasmid as a Potentially Useful Vector in *Pseudomonas* Species." Journal of Bacteriology, Mar. 1978, pp. 1527-1529, vol. 133, No. 3, American Society for Microbiology.

Nagahira, et al., Humanization of a mouse neutralizing monoclonal antibody against tumor necrosis factor-alpha (TNF-alpha), J Immunol Methods. Jan. 1, 1999;222(1-2):83-92.

Nakamaye, K. and Eckstein F., "Inhibition of restriction endonuclease Nci I cleavage by phosphorothioate groups and its application to oligonucleotide-directed mutagenesis," 1986, Nucl. Acids Res. 14, 9679-98.

Nedospasov, et al., 1986, "Tandem arrangement of genes coding for tumor necrosis factor (TNF-alpha) and lymphotoxin (TNF-beta) in the human genome," Cold Spring Harb. Symp. Quant. Biol. 51 Pt 1, 611-624.

Needleman, Saul B., et al., "A General Method Applicable to the Search for Similarities in the Amino Acid Sequence of Two Proteins," J. Mol. Biol., 1970, pp. 443-453, vol. 48.

Neu and Heppel, "The Release of Ribonuclease into the Medium when *Escherichia coli* Cells are converted to Spheroplasts," (1964) J. Biol. Chem 239: 3893-3900.

Nieto, C., et al., "Cloning Vectors, Derived From a Naturally Occurring Plasmid of Pseudomonas Savastanoi, Specifically Tailored for Genetic Manipulation in Pseudomonas," Gene, 1990, pp. 145-149, vol. 87, Elsevier.

Niwa, et al., "An Efficient Gene-Trap Method Using Poly A Trap Vectors and Characterization of Gene-Trap Events," 1993, J. Biochem 113:343-349.

Olekhnovich, Igor N., el al., "Controlled-Expression Shuttle Vector for Pseudomonads Based on the trpIBA genes of Pseudomonas Putida," Gene, 1994, pp. 63-65, vol. 140, Elsevier Science.

Park, S., et al., "Secretory production of recombinant protein by a high density culture of a protease negative mutant *Escherichia coli* strain," 1999, Biotechnol. Progr 15, pp. 164-167.

PCT/US05/01549 International Search Report mailed Jul. 19, 2005.

PCT/US08/61483 Search Report dated Nov. 7, 2008.

Perussia, Bice, et al., "Immune Interferon Induces the Receptor for Monomeric IgG1 on Human Monocytic and Myeloid Cells," J. Exp. Med., 1983, pp. 1092-1113, vol. 158, Rockefeller University Press.

Pierce, et al., "Expression and Recovery of cominant periplasmically secreted or amyase derived from Streptomyces thermoviolaceus," (1995) Icheme Research Event 2: 995-997.

Pighetti, Gina M., et al., Specific Immune Responses of Dairy Cattle Atter Primary Inoculation with Recombinant Bonvine Interferon-y as an Adjuvant When Vaccinating Against Mastitis, American Journal of Veterinary Research, 1996, pp. 819-824, vol. 57, No. 6.

Pilon, et al., "High-Level expression and efficient recovery of ubiquitin fusion proteins from *Escherichia coli*." Biotechnol Prog., 1996, vol. 12, No. 3, pp. 331-337.

Puehler, et al., 1984, Advanced Molecular Genetics New York, Heidelberg, Berlin, Tokyo, Springer Verlag.

Quevillon et al., "InterPro Scan: protein domains identifier," 2005, Nucleic Acids Research 33: W116-W120.

Radding, C.M., "Homologous pairing and strand exchange in genetic recombination." (1982) Ann. Rev. Genet. 16: 405.

Ralph, Peter, "Human B Cell-Inducing Factor(s) for Production of IgM, IgG and 19A; Independence From IL 2(1)." The Journal of Immunology, Apr. 1984, pp. 1858-1862, vol. 132, No. 4, The American Society of Immunologists.

Ranson, et al., "Chaperonins," 1998, BioChem. J. 333, 233-242.

Rao, et al., "Stable three-stranded DNA made by RecA protein," 1991, PNAS 88: pp. 2984-2988.

Retallack, Diane, et al., "Transport of heterologous proteins to the periplasmic space of Pseudomonas fluorescens using a variety of native signal sequences," Biotechnology Letters, 2007, pp. 1483-1491, vol. 29, Springer Science+Business Media B.V.

Riesenberg, D., et al., "High Cell Density Cultivation of *Escherichia coli* at Controlled Specific Growth Rate," Journal of Biotechnology, 1991, pp. 17-28, vol. 20, Elsevier Science Publishers, B.V.

Rosenberg, et al. "Vectors for selective expression of cloned DNAs by T7 RNA polymerase." 1987, Gene, 56(1): 125-35.

(56) References Cited

OTHER PUBLICATIONS

Ruiz-Taylor, LA et al., "Monolayers of derivatized poly(L-lysine)-grafted poly(ethylene glycol) on metal oxides as a class of biomolecular interfaces," 2001, Proc Natl Acad Sci USA, 98:852-857.
Ruiz-Taylor, LA, et al., "X-ray photoelectron spectroscopy and radiometry studies of biotin-derivatized poly(L-lysine)-grafted-poly(ethylene glycol) monolayers on metal oxides," 2001, Langmuir, 7313-7322.
Sabina, J., et al., "Interfering with Different Steps of Protein Synthesis Explored by Transcriptional Profiling of Escherichia coli K-12," 2003, J. Bacteriol 185, pp. 6158-6170.
Saiki, Osamu, et al., Induction of Human Immunoglobulin Secretion—I. Synergistic Effect of B Cell Mitogen Cowan I Plus T Cell Mitogens or Factors, The Journal of Immunology, Sep. 1981, pp. 1044-1047, vol. 127, No. 3, The American Association of Immunologists.
Sanchez-Romero & V. De Lorenzo, (1999) Manual of Industrial Microbiology and Biotechnology (A. Demain & J. Davies, eds.) pp. 460-474.
Sciiein, C.II., "Production of Soluble recombinant Proteins in Bacteria," Bio/Technology (1989), 7:1141-1149.
Schena, M., et al., "Quantitative monitoring of gene expression patterns with a complementary DNA microarray,"1995, Science 270:467-70.
Schweizer, Herbert P., et al., Vector Design and Development of Host Systems for Pseudomonas, Genetic Engineering, (2001) pp. 69-81, vol. 23, Kluwer Academic/Plenum Publishers.
Schweizer, Herbert P., Vectors to Express Foreign Genes and Techniques to Monitor Gene Expression in Pseudomonads, Current Opinion in Biotechnology, 2001, pp. 439-445, vol. 12, Elsevier Science Ltd.
Service, R.F., et al., "Tapping DNA for structures produces a trickle." Science 298:948-950 (2002).
SG200906987-3 Exam Report dated Sep. 26, 2011.
Shine and Dalgarno, "The 3'-terminal sequence of Escherichia coli ribosomal RNA: complementarity to nonsense triplets and ribosome binding sites," (1974) Proc. Natl. Sci. USA 71:1342-1346.
Shokri, et al., "Growth rate-dependent changes in Escherichia coli membrane structure and protein leakage," (2002) App. Microbiol. Biotechnol 58:386-392.
Simmons, et al., "Expression of full-length immunoglobins in Escherichia coli: rapid and efficient production of aglycosylated," (2002) J. Immun. Meth. 263:133-147.
Singleton, Paul & Sainsbury, Diana: "Dictionary of Microbiology," 1978, John Wiley & Sons Ltd., Chichester, UK, XP002667935 pp. 332-333.
Smith & Waterman, Michael S., "Comparison of Biosequences." 1981, Adv. Appl. Math 2:482-489.
Smits, et al., "New Alkane-responsive expression vectors for Escherichia coli and pseudomonas," Plasmid, 2001, vol. 46, p. 16-24.
Song, K.Y., et al., "Accurate modification of a chromosomal plasmid by homologous recombination in human cells," (1987) Proc. Natl. Acad. Sci. USA 84:6820-6824.
Sordillo, L.M., Controlling Acute Escherichia coli Mastitis During the Periparturient Period with Recombinant Bovine Interferon-Gamma, Veterinary Microbiology, 1991, pp. 189-198, vol. 28.
Southern, P. and P. Berg, "Transformation of mammalian cells to antibiotic resistance with a bacterial gene under control of the SV40 early region promoter," (1982) J. Mol. Appl. Genet. 1:327-341.
Squires, et al., "Heterologous protein production in P. Fluorescens," Bioprocess International, 2004, vol. 2, No. 11, pp. 54-56, 58-59.
Steidler, L., In Situ Delivery of Cytokines by Genetically Engineered Lactococcus Lactis, Antonie van Leeuwenhoek, 2002, pp. 323-331, vol. 82.
Studier, F.W. and B.A. Moffatt, "Use of bacteriophage T7 RNA polymerase to direct selective high-level expression of cloned genes," 1986, Journal of Molecular Biology 189(1):113-30.

Suzek, Baris E., et al., "A Probalistic Method for Identifying Start Codons in Bacterial Genomes." Bioinformatics, 2001, pp. 1123-1130, vol. 17, No. 12, Oxford University Press.
Taguchi, et al., "Comparison of secretory expression in Escherichia coli and Streptomyces subtilisin inhibtor (SSI) gene." (1990) Biochimica Biophysica Acta 1049: 278-85.
Tanji, et al., "Controlled Expression of Lysis Genes Encoded in T4 Phage for the Gentle Disruption of Escherichia coli cells," (1998) J. Ferment and Bioeng., 85:74-78.
Taub, Dennis D., "Cytokine, growth factor, and chemokine ligand database," Current Protocols in Immunology, 2004, XP002677096, DOI: 10.1002/0471142735.im0629s61, [Retrieved from the Internet: URL:http://onlinelibrary.wiley.com/doi/10.1002/0471142735.im0629s61/full [retrieved on Jun. 1, 2012].
Taylor, J.W., et al., "The use of phosphorothioate-modified DNA in restriction enzyme reactions to prepare nicked DNA," 1985, Nucl. Acids Res. 13, No. 24, pp. 8749-8764.
Te Riele H., et al., "Consecutive inactivation of both alleles of the pim-1 proto-oncogene by homologous recombination in embryonic stem cells." (1990) Nature 348:649-651.
Tsuda & Nakazawa, "A mutagenesis system utilizing a Tn1722 derivative containing an Escherichia coli-specific vector plasmid: application to Pseudomonas species," (1993) Gene 136 (1-2): 257-62.
U.S. Appl. No. 12/109,554 Non Final Office Action mailed Dec. 30, 2010.
U.S. Appl. No. 12/109,554 Final Office Action mailed Jun. 15, 2011.
U.S. Appl. No. 11/189,375 Non Final Office Action mailed Feb. 7, 2008.
U.S. Appl. No. 11/189,375 Non Final Office Action mailed Sep. 9, 2009.
U.S. Appl. No. 11/189,375 Final Office Action mailed Jun. 16, 2010.
U.S. Appl. No. 11/189,375 Final Office Action mailed Mar. 19, 2009.
U.S. Appl. No. 12/610,207 Final Office Action issued Nov. 30, 2012.
U.S. Appl. No. 11/038,901 Office Action mailed Nov. 25, 2011.
U.S. Appl. No. 11/038,901 Non Final Office Action mailed Apr. 15, 2011.
U.S. Appl. No. 11/038,901 Final Office Action mailed Sep. 17, 2009.
U.S. Appl. No. 11/038,901 Non Final Office Action mailed Aug. 6, 2008.
U.S. Appl. No. 11/038,901 Final Office Action mailed Feb. 27, 2008.
U.S. Appl. No. 11/038,901 Non-Final Office Action mailed Jul. 27, 2007.
U.S. Appl. No. 11/400,840 Office Action mailed Feb. 14, 2008.
U.S. Appl. No. 11/400,840 Office Action mailed Sep. 17, 2008.
U.S. Appl. No. 11/400,840 Office Action mailed Dec. 24, 2009.
Vincentelli, Renaud, et al., "Medium-Scale Structural Genomics: Strategies for Protein Expression and Crystallization," Ace. Chem. Res., 2003, pp. 165-172, vol. 36, No. 3.
Vinogradov, Alexi A., et al., Solubilization and Refolding of Inclusion Body Proteins in Reverse Micelles, Analytical Biochemistry, 2003, pp. 234-238, vol. 320, Elsevier Science.
Wackemagel, et al., "The periplasmic endonuclease I of Escherichia coli has amino-acid sequence homology to the extracellular Dnases of Vibrio cholerae and aeromonas hydrophila," (1995) Gene 154: 55-59.
Wang, et al., 1985, "Molecular cloning of the complementary DNA for human tumor necrosis factor," Science 228 (4696), 149-154.
Waterman, Michael. S., Comparison of Biosequences, Advances in Applied Mathematics, 1981, pp. 482-489, vol. 2, Academic Press, Inc.
Wei, Y., et al., "High-density microarray-mediated gene expression profiling of Escherichia coli," 2001, J. Bacteriol 183(2), pp. 545-556.
Wesolowski, et al., 2009, "Single domain antibodies: promising experimental and therapeutic tools in infection and immunity," Med Microbiol Immunol. 198(3): 157-174.

(56) References Cited

OTHER PUBLICATIONS

Wilson, D.S., et al., "The use of mRNA display to select high-affinity protein-binding peptides," 2001, Proc Nat Acad Sci USA 98:3750-3755.
Yilma, T.K., et al., Expression of an Adjuvant Gene (Interferon-y) an Infectious Vaccinia Virus Recombinants, Vaccines, 1987, pp. 393-396, vol. 87.
Yoshida, et al., "A new strategy of gene trapping in ES cells using 3'RACE," Transgenic Research 4:277-287 (1995).
Zapata et al., 1995, "Engineering linear F(ab')2 fragments for efficient production in *Escherichia coli* and enhanced antiproliferative activity," Protein *Eng.* 8(10): 1057-1062.
Zinder and Arndt, "Production of Protoplasts of *Escherichia coli* by Lysozyme Treatment," Proc. Mathl. Acad. Sci. USA 1956, 42: 586-590.
Canadian Patent Application CA2553503 Exam Report dated May 2, 2013.
Canadian Patent Application CA2553503 Exam Report dated Apr. 29, 2014.
Canadian Patent Application CA2574953 Office Action dated Jul. 23, 2013.
Canadian Patent Application CA2685326 Office Action dated May 22, 2014.
EP11173331.7 Office action dated Nov. 6, 2013.
EP12198545 Extended European Search Report dated Jun. 14, 2013.
Hsiung et al., "Use of Bacteriocin Release Protein in *E. coli* for Excretion of Human Growth Hormone into the Culture Medium," (1989), Biol Technology 7:267-71.
Japanese Patent Application 2006-549690 Office Action mailed Mar. 11, 2014.
Japanese Patent Application 2011-132011 Office Action mailed Jul. 9, 2013.
Japanese Patent Application 2011-132011 Office Action mailed Mar. 18, 2014.
Japanese Patent Application 2010-506503 Office Action dated May 14, 2013.
Korean Patent Application 10-2007-7004418 Exam Report dated Jun. 25, 2013.
Korean Patent Application 10-2013-7002343 Office Action dated Feb. 25, 2014.
Singleton, et al., "Cloning, expression, and characterization of pyrrolidone carboxyl peptidase from the archaeon Thermococcus litoralis" Extremophiles 4(5):297-303 (2000).
Takara Bio Inc., Product Information Bulletin, "Chaperone Plasmid Set," pp. 1-8, Catalog #3340, Version 0401, Mar. 22, 2013.
U.S. Appl. No. 11/038,901 Office Action mailed Dec. 17, 2013.
U.S. Appl. No. 11/189,375 Final Office Action mailed Mar. 29, 2013.
U.S. Appl. No. 11/400,840 Office Action mailed Mar. 28, 2014.
EP Application No. 05705852.1 Invitation pursuant to Article 94(3) dated May 26, 2015.
Korean Patent Application 10-2009-7024636 Office Action dated Nov. 26, 2014.
U.S. Appl. No. 14/071,273 Office Action mailed Oct. 9, 2014.
U.S. Appl. No. 11/400,840 Office Action mailed Apr. 30, 2015.

\* cited by examiner

A.
MFPTIPLSRPFDNAMLRAHRLHQLAFDTYQEFEEAYIPKEQKYSFLQNPQTSLCFSESI
PTPSNREETQQKSNLELLRISLLLIQSWLEPVQFLRSVFANSLVYGASDSNVYDLLKDL
EEGIQTLMGRLEDGSPRTGQIFKQTYSKFDTNSHNDDALLKNYGLLYCFRKDMDKVE
TFLRIVQCRSVEGSCGF (SEQ ID NO: 16)

B.

```
                agagaactagtaaaaaggagaaatccATGCAGGGCCAATTTTTTAGA
    1       ---------+---------+---------+---------+-------- 47
                tctcttgatcatttttcctctttaggTACGTCCCGGTTAAAAAATCT

M  Q  G  Q  F  F  R

GAAATAGAAAACTTAAAGGAGTATTTTAATGCAAGTAGCCCAGATGTAGCTAAGGGTGGG
    48      ---------+---------+---------+---------+ ---------+---------+ 107
            CTTTATCTTTTGAATTTCCTCATAAAATTACGTTCATCGGGTCTACATCGATTCCCACCC

E  I  E  N  L  K  E  Y  F  N  A  S  S  P  D  V  A  K  G  G

CCTCTCTTCTCAGAAATTTTGAAGAATTGGAAAGATGAAAGTGACAAAAAAATTATTCAG
    108     ---------+---------+---------+---------+---------+---------+ 167
            GGAGAGAAGAGTCTTTAAAACTTCTTAACCTTTCTACTTTCACTGTTTTTTTAATAAGTC

P  L  F  S  E  I  L  K  N  W  K  D  E  S  D  K  K  I  I  Q

AGCCAAATTGTCTCCTTCTACTTCAAACTCTTTGAAAACCTCAAAGATAACCAGGTCATT
    168     ---------+---------+---------+---------+---------+---------+ 227
            TCGGTTTAACAGAGGAAGATGAAGTTTGAGAAACTTTTGGAGTTTCTATTGGTCCAGTAA

S  Q  I  V  S  F  Y  F  K  L  F  E  N  L  K  D  N  Q  V  I

CAAAGGAGCATGGATATCATCAAGCAAGACATGTTTCAGAAGTTCTTGAATGGCAGCTCT
    228     ---------+---------+---------+---------+---------+---------+ 287
            GTTTCCTCGTACCTATAGTAGTTCGTTCTGTACAAAGTCTTCAAGAACTTACCGTCGAGA

Q  R  S  M  D  I  I  K  Q  D  M  F  Q  K  F  L  N  G  S  S

GAGAAACTGGAGGACTTCAAAAAGCTGATTCAAATTCCGGTGGATGATCTGCAGATCCAG
    288     ---------+---------+---------+---------+---------+---------+ 347
            CTCTTTGACCTCCTGAAGTTTTTCGACTAAGTTTAAGGCCACCTACTAGACGTCTAGGTC

E  K  L  E  D  F  K  K  L  I  Q  I  P  V  D  D  L  Q  I  Q

CGCAAAGCCATAAATGAACTCATCAAAGTGATGAATGACCTGTCACCAAAATCTAACCTC
    348     ---------+---------+---------+---------+---------+---------+ 407
            GCGTTTCGGTATTTACTTGAGTAGTTTCACTACTTACTGGACAGTGGTTTTAGATTGGAG

R  K  A  I  N  E  L  I  K  V  M  N  D  L  S  P  K  S  N  L

AGAAAGCGGAAGAGAAGTCAGAATCTCTTTCGAGGCCGGAGAGCATCAACGtaatgactcgagtctct
    408     ---------+---------+---------+---------+---------+---------+-------- 475
            TCTTTCGCCTTCTCTTCAGTCTTAGAGAAAGCTCCGGCCTCTCGTAGTTGCattactgagctcagaga

R  K  R  K  R  S  Q  N  L  F  R  G  R  R  A  S  T  *

(SEQ ID NO: 17)
```

FIGURE 7

```
atg aaa ctg aaa cgt ctg atg gcg gca atg act ttt gtc gct gct ggc      48
Met Lys Leu Lys Arg Leu Met Ala Ala Met Thr Phe Val Ala Ala Gly
 1               5                  10                  15 gtt gcg acc gcc aac gcg gtg gcc gcc cag gtg cag ctg cag gag tcg      96
Val Ala Thr Ala Asn Ala Val Ala Ala Gln Val Gln Leu Gln Glu Ser
             20                  25                  30 ggc cca gga ctg gtg aag cct tcg gag acc ctg tcc ctc acc tgc act     144
Gly Pro Gly Leu Val Lys Pro Ser Glu Thr Leu Ser Leu Thr Cys Thr
         35                  40                  45 gtc tct ggt ggt tcc atc agt agt tat cac tgg agc tgg atc cgg cag     192
Val Ser Gly Gly Ser Ile Ser Ser Tyr His Trp Ser Trp Ile Arg Gln
     50                  55                  60 ccc cca ggg aag gga ctg gag tgg att ggg tat atc tat tac agt ggg     240
Pro Pro Gly Lys Gly Leu Glu Trp Ile Gly Tyr Ile Tyr Tyr Ser Gly
 65                  70                  75                  80 agc acc aac tac aac ccc tcc ctc aag aat cga gtc acc ata tct gta     288
Ser Thr Asn Tyr Asn Pro Ser Leu Lys Asn Arg Val Thr Ile Ser Val
                 85                  90                  95 gac acg tcc aag aac cag ttc tcc ctg aac ctg agg tct gtg acc gct     336
Asp Thr Ser Lys Asn Gln Phe Ser Leu Asn Leu Arg Ser Val Thr Ala
            100                 105                 110 gca gac acg gcc gtg tat tac tgt gcg cga gga acg tat ggc cca gcc     384
Ala Asp Thr Ala Val Tyr Tyr Cys Ala Arg Gly Thr Tyr Gly Pro Ala
        115                 120                 125 gga gat gct ttt gat atc tgg ggg caa ggg acc acg gtc acc gtc tcg     432
Gly Asp Ala Phe Asp Ile Trp Gly Gln Gly Thr Thr Val Thr Val Ser
    130                 135                 140 agt ggt gga ggc ggt tca ggc gga ggt ggc agc ggc ggt ggc gga tcg     480
Ser Gly Gly Gly Gly Ser Gly Gly Gly Gly Ser Gly Gly Gly Gly Ser
145                 150                 155                 160 gac atc cag atg acc cag tct cct tcc acc ctg tct gca tct att gga     528
Asp Ile Gln Met Thr Gln Ser Pro Ser Thr Leu Ser Ala Ser Ile Gly
                165                 170                 175 gac aga gtc acc atc acc tgc cgg gcc agt gag ggt att tat cac tgg     576
Asp Arg Val Thr Ile Thr Cys Arg Ala Ser Glu Gly Ile Tyr His Trp
            180                 185                 190 ctg gcc tgg tat cag cag aag cca ggg aaa gcc cct aaa ctc ctg atc     624
Leu Ala Trp Tyr Gln Gln Lys Pro Gly Lys Ala Pro Lys Leu Leu Ile
        195                 200                 205 tat aag gcc tct agt tta gcc agt ggg gcc cca tca agg ttc agc ggc     672
Tyr Lys Ala Ser Ser Leu Ala Ser Gly Ala Pro Ser Arg Phe Ser Gly
    210                 215                 220 agt gga tct ggg aca gat ttc act ctc acc atc agc agc ctg cag cct     720
Ser Gly Ser Gly Thr Asp Phe Thr Leu Thr Ile Ser Ser Leu Gln Pro
225                 230                 235                 240 gat gat ttt gca act tat tac tgc caa caa tat agt aat tat ccg ctc     768
Asp Asp Phe Ala Thr Tyr Tyr Cys Gln Gln Tyr Ser Asn Tyr Pro Leu
                245                 250                 255 act ttc ggc gga ggg acc aag ctg gag atc aaa cgt gcg gcc gca cat     816
Thr Phe Gly Gly Gly Thr Lys Leu Glu Ile Lys Arg Ala Ala Ala His
            260                 265                 270 cac cat cat cac cat taa    (SEQ ID NO: 18)                           834
His His His His His
        275
```

FIGURE 8

Met Lys Leu Lys Arg Leu Met Ala Ala Met Thr Phe Val Ala Ala Gly

Val Ala Thr Ala Asn Ala Val Ala Ala Gln Val Gln Leu Gln Glu Ser
            20                  25                30

Gly Pro Gly Leu Val Lys Pro Ser Glu Thr Leu Ser Leu Thr Cys Thr
        35                  40              45

Val Ser Gly Gly Ser Ile Ser Ser Tyr His Trp Ser Trp Ile Arg Gln
    50              55                  60

Pro Pro Gly Lys Gly Leu Glu Trp Ile Gly Tyr Ile Tyr Tyr Ser Gly
65              70                  75                  80

Ser Thr Asn Tyr Asn Pro Ser Leu Lys Asn Arg Val Thr Ile Ser Val
            85                  90                  95

Asp Thr Ser Lys Asn Gln Phe Ser Leu Asn Leu Arg Ser Val Thr Ala
            100                 105                 110

Ala Asp Thr Ala Val Tyr Tyr Cys Ala Arg Gly Thr Tyr Gly Pro Ala
        115             120                 125

Gly Asp Ala Phe Asp Ile Trp Gly Gln Gly Thr Thr Val Thr Val Ser
    130             135                 140

Ser Gly Gly Gly Gly Ser Gly Gly Gly Gly Ser Gly Gly Gly Gly Ser
145             150                 155                 160

Asp Ile Gln Met Thr Gln Ser Pro Ser Thr Leu Ser Ala Ser Ile Gly
            165                 170                 175

Asp Arg Val Thr Ile Thr Cys Arg Ala Ser Glu Gly Ile Tyr His Trp
            180                 185                 190

Leu Ala Trp Tyr Gln Gln Lys Pro Gly Lys Ala Pro Lys Leu Leu Ile
        195                 200             205

Tyr Lys Ala Ser Ser Leu Ala Ser Gly Ala Pro Ser Arg Phe Ser Gly
    210             215                 220

Ser Gly Ser Gly Thr Asp Phe Thr Leu Thr Ile Ser Ser Leu Gln Pro
225             230                 235                 240

Asp Asp Phe Ala Thr Tyr Tyr Cys Gln Gln Tyr Ser Asn Tyr Pro Leu
            245             250                 255

Thr Phe Gly Gly Gly Thr Lys Leu Glu Ile Lys Arg Ala Ala Ala His
        260             265                 270
His His His His His        (SEQ ID NO: 19)
        275

FIGURE 9

```
atg aaa ctg aaa cgt ttg atg gcg gca atg act ttt gtc gct gct ggc        48
Met Lys Leu Lys Arg Leu Met Ala Ala Met Thr Phe Val Ala Ala Gly
1               5                   10                  15 gtt gcg acc gcc aac gcg gtg gcc ttc cca acc att ccc tta tcc agg        96
Val Ala Thr Ala Asn Ala Val Ala Phe Pro Thr Ile Pro Leu Ser Arg
            20                  25                  30 cct ttt gac aac gct atg ctc cgc gcc cat cgt ctg cac cag ctg gcc       144
Pro Phe Asp Asn Ala Met Leu Arg Ala His Arg Leu His Gln Leu Ala
        35                  40                  45 ttt gac acc tac cag gag ttt gaa gaa gcc tat atc cca aag gaa cag       192
Phe Asp Thr Tyr Gln Glu Phe Glu Glu Ala Tyr Ile Pro Lys Glu Gln
    50                  55                  60 aag tat tca ttc ctg cag aac ccc cag acc tcc ctc tgt ttc tca gag       240
Lys Tyr Ser Phe Leu Gln Asn Pro Gln Thr Ser Leu Cys Phe Ser Glu
65              70                  75                  80 tct att ccg aca ccc tcc aac agg gag gaa aca caa cag aaa tcc aac       288
Ser Ile Pro Thr Pro Ser Asn Arg Glu Glu Thr Gln Gln Lys Ser Asn
            85                  90                  95 cta gag ctg ctc cgc atc tcc ctg ctg ctc atc cag tcg tgg ctg gag       336
Leu Glu Leu Leu Arg Ile Ser Leu Leu Leu Ile Gln Ser Trp Leu Glu
        100                 105                 110 ccc gtg cag ttc ctc agg agt gtc ttc gcc aac agc ctg gtg tac ggc       384
Pro Val Gln Phe Leu Arg Ser Val Phe Ala Asn Ser Leu Val Tyr Gly
    115                 120                 125 gcc tct gac agc aac gtc tat gac ctc cta aag gac cta gag gaa ggc       432
Ala Ser Asp Ser Asn Val Tyr Asp Leu Leu Lys Asp Leu Glu Glu Gly
130                 135                 140 atc caa acg ctg atg ggg agg ctg gaa gat ggc agc ccc cgg act ggg       480
Ile Gln Thr Leu Met Gly Arg Leu Glu Asp Gly Ser Pro Arg Thr Gly
145             150                 155                 160 cag atc ttc aag cag acc tac agc aag ttc gac aca aac tca cac aac       528
Gln Ile Phe Lys Gln Thr Tyr Ser Lys Phe Asp Thr Asn Ser His Asn
        165                 170                 175 gat gac gca cta ctc aag aac tac ggg ctg ctc tac tgc ttc agg aag       576
Asp Asp Ala Leu Leu Lys Asn Tyr Gly Leu Leu Tyr Cys Phe Arg Lys
            180                 185                 190 gac atg gac aag gtc gag aca ttc ctg cgc atc gtg cag tgc cgc tct       624
Asp Met Asp Lys Val Glu Thr Phe Leu Arg Ile Val Gln Cys Arg Ser
        195                 200                 205 gtg gag ggc agc tgt ggc ttc taa    (SEQ ID NO: 20)                    648
Val Glu Gly Ser Cys Gly Phe
210                 215
```

FIGURE 10

Met Lys Leu Lys Arg Leu Met Ala Ala Met Thr Phe Val Ala Ala Gly
1               5                   10                  15

Val Ala Thr Ala Asn Ala Val Ala Phe Pro Thr Ile Pro Leu Ser Arg
                20                  25                  30

Pro Phe Asp Asn Ala Met Leu Arg Ala His Arg Leu His Gln Leu Ala
            35                  40                  45

Phe Asp Thr Tyr Gln Glu Phe Glu Glu Ala Tyr Ile Pro Lys Glu Gln
        50                  55                  60

Lys Tyr Ser Phe Leu Gln Asn Pro Gln Thr Ser Leu Cys Phe Ser Glu
65                  70                  75                  80

Ser Ile Pro Thr Pro Ser Asn Arg Glu Glu Thr Gln Gln Lys Ser Asn
                85                  90                  95

Leu Glu Leu Leu Arg Ile Ser Leu Leu Leu Ile Gln Ser Trp Leu Glu
            100                 105                 110

Pro Val Gln Phe Leu Arg Ser Val Phe Ala Asn Ser Leu Val Tyr Gly
        115                 120                 125

Ala Ser Asp Ser Asn Val Tyr Asp Leu Leu Lys Asp Leu Glu Glu Gly
    130                 135                 140

Ile Gln Thr Leu Met Gly Arg Leu Glu Asp Gly Ser Pro Arg Thr Gly
145                 150                 155                 160

Gln Ile Phe Lys Gln Thr Tyr Ser Lys Phe Asp Thr Asn Ser His Asn
            165                 170                 175

Asp Asp Ala Leu Leu Lys Asn Tyr Gly Leu Leu Tyr Cys Phe Arg Lys
            180                 185                 190

Asp Met Asp Lys Val Glu Thr Phe Leu Arg Ile Val Gln Cys Arg Ser
        195                 200                 205

Val Glu Gly Ser Cys Gly Phe     (SEQ ID NO: 21)
    210             215

FIGURE 11

SEQUENCE LISTING

<160> NUMBER OF SEQ ID NOS: 29

<210> SEQ ID NO 1
<211> LENGTH: 609
<212> TYPE: PRT
<213> ORGANISM: Homo sapiens

<400> SEQUENCE: 1

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

```
Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Lys Gln Leu Gly Glu Tyr Lys Phe Gln Asn Ala Leu Leu
                420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
                500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
                580                 585                 590

Ala Glu Glu Gly Lys Lys Leu Val Ala Ala Ser Gln Ala Ala Leu Gly
        595                 600                 605

Leu

<210> SEQ ID NO 2
<211> LENGTH: 698
<212> TYPE: PRT
<213> ORGANISM: Homo sapiens

<400> SEQUENCE: 2

Met Arg Leu Ala Val Gly Ala Leu Leu Val Cys Ala Val Leu Gly Leu
1               5                   10                  15

Cys Leu Ala Val Pro Asp Lys Thr Val Arg Trp Cys Ala Val Ser Glu
                20                  25                  30

His Glu Ala Thr Lys Cys Gln Ser Phe Arg Asp His Met Lys Ser Val
            35                  40                  45

Ile Pro Ser Asp Gly Pro Ser Val Ala Cys Val Lys Lys Ala Ser Tyr
        50                  55                  60

Leu Asp Cys Ile Arg Ala Ile Ala Ala Asn Glu Ala Asp Ala Val Thr
65                  70                  75                  80

Leu Asp Ala Gly Leu Val Tyr Asp Ala Tyr Leu Ala Pro Asn Asn Leu
                85                  90                  95

Lys Pro Val Val Ala Glu Phe Tyr Gly Ser Lys Glu Asp Pro Gln Thr
                100                 105                 110

Phe Tyr Tyr Ala Val Ala Val Val Lys Lys Asp Ser Gly Phe Gln Met
            115                 120                 125
```

```
Asn Gln Leu Arg Gly Lys Lys Ser Cys His Thr Gly Leu Gly Arg Ser
    130                 135                 140

Ala Gly Trp Asn Ile Pro Ile Gly Leu Leu Tyr Cys Asp Leu Pro Glu
145                 150                 155                 160

Pro Arg Lys Pro Leu Glu Lys Ala Val Ala Asn Phe Phe Ser Gly Ser
                165                 170                 175

Cys Ala Pro Cys Ala Asp Gly Thr Asp Phe Pro Gln Leu Cys Gln Leu
            180                 185                 190

Cys Pro Gly Cys Gly Cys Ser Thr Leu Asn Gln Tyr Phe Gly Tyr Ser
        195                 200                 205

Gly Ala Phe Lys Cys Leu Lys Asn Gly Ala Gly Asp Val Ala Phe Val
    210                 215                 220

Lys His Ser Thr Ile Phe Glu Asn Leu Ala Asn Lys Ala Asp Arg Asp
225                 230                 235                 240

Gln Tyr Glu Leu Leu Cys Leu Asp Asn Thr Arg Lys Pro Val Asp Glu
                245                 250                 255

Tyr Lys Asp Cys His Leu Ala Gln Val Pro Ser His Thr Val Val Ala
            260                 265                 270

Arg Ser Met Gly Gly Lys Glu Asp Leu Ile Trp Glu Leu Leu Asn Gln
        275                 280                 285

Ala Gln Glu His Phe Gly Lys Asp Lys Ser Lys Glu Phe Gln Leu Phe
    290                 295                 300

Ser Ser Pro His Gly Lys Asp Leu Leu Phe Lys Asp Ser Ala His Gly
305                 310                 315                 320

Phe Leu Lys Val Pro Pro Arg Met Asp Ala Lys Met Tyr Leu Gly Tyr
                325                 330                 335

Glu Tyr Val Thr Ala Ile Arg Asn Leu Arg Glu Gly Thr Cys Gln Glu
            340                 345                 350

Ala Pro Thr Asp Glu Cys Lys Pro Val Lys Trp Cys Ala Leu Ser His
        355                 360                 365

His Glu Arg Leu Lys Cys Asp Glu Trp Ser Val Asn Ser Val Gly Lys
    370                 375                 380

Ile Glu Cys Val Ser Ala Glu Thr Thr Glu Asp Cys Ile Ala Lys Ile
385                 390                 395                 400

Met Asn Gly Glu Ala Asp Ala Met Ser Leu Asp Gly Gly Phe Val Tyr
                405                 410                 415

Ile Ala Gly Lys Cys Gly Leu Val Pro Val Leu Ala Glu Asn Tyr Asn
            420                 425                 430

Lys Ser Asp Asn Cys Glu Asp Thr Pro Glu Ala Gly Tyr Phe Ala Val
        435                 440                 445

Ala Val Val Lys Lys Ser Ala Ser Asp Leu Thr Trp Asp Asn Leu Lys
    450                 455                 460

Gly Lys Lys Ser Cys His Thr Ala Val Gly Arg Thr Ala Gly Trp Asn
465                 470                 475                 480

Ile Pro Met Gly Leu Leu Tyr Asn Lys Ile Asn His Cys Arg Phe Asp
                485                 490                 495

Glu Phe Phe Ser Glu Gly Cys Ala Pro Gly Ser Lys Lys Asp Ser Ser
            500                 505                 510

Leu Cys Lys Leu Cys Met Gly Ser Gly Leu Asn Leu Cys Glu Pro Asn
        515                 520                 525

Asn Lys Glu Gly Tyr Tyr Gly Tyr Thr Gly Ala Phe Arg Cys Leu Val
    530                 535                 540

Glu Lys Gly Asp Val Ala Phe Val Lys His Gln Thr Val Pro Gln Asn
```

```
            545                 550                 555                 560
        Thr Gly Gly Lys Asn Pro Asp Pro Trp Ala Lys Asn Leu Asn Glu Lys
                        565                 570                 575

Asp Tyr Glu Leu Leu Cys Leu Asp Gly Thr Arg Lys Pro Val Glu Glu
                    580                 585                 590

Tyr Ala Asn Cys His Leu Ala Arg Ala Pro Asn His Ala Val Val Thr
                595                 600                 605

Arg Lys Asp Lys Glu Ala Cys Val His Lys Ile Leu Arg Gln Gln Gln
            610                 615                 620

His Leu Phe Gly Ser Asn Val Thr Asp Cys Ser Gly Asn Phe Cys Leu
        625                 630                 635                 640

Phe Arg Ser Glu Thr Lys Asp Leu Leu Phe Arg Asp Asp Thr Val Cys
                        645                 650                 655

Leu Ala Lys Leu His Asp Arg Asn Thr Tyr Glu Lys Tyr Leu Gly Glu
                    660                 665                 670

Glu Tyr Val Lys Ala Val Gly Asn Leu Arg Lys Cys Ser Thr Ser Ser
                675                 680                 685

Leu Leu Glu Ala Cys Thr Phe Arg Arg Pro
            690                 695

<210> SEQ ID NO 3
<211> LENGTH: 333
<212> TYPE: DNA
<213> ORGANISM: Homo sapiens

<400> SEQUENCE: 3
atggccctgt ggatgcgcct cctgcccctg ctggcgctgc tggccctctg gggacctgac     60
ccagccgcag cctttgtgaa ccaacacctg tgcggctcac acctggtgga agctctctac    120
ctagtgtgcg gggaacgagg cttcttctac acacccaaga cccgccggga ggcagaggac    180
ctgcaggtgg gcaggtgga gctgggcggg ggccctggtg caggcagcct gcagcccttg    240
gccctggagg ggtccctgca gaagcgtggc attgtggaac aatgctgtac cagcatctgc    300
tccctctacc agctggagaa ctactgcaac tag                                 333

<210> SEQ ID NO 4
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agagaactag taaaaaggag aaatccatgt tcccaaccat tcccttatc                  49

<210> SEQ ID NO 5
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agagaactag taaaaaggag aaatccatgt tcccaaccat tcccttatcc aggccttttg     60
ac                                                                    62

<210> SEQ ID NO 6
```

```
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agagaactag taaaaaggag aaatccatgg ctacaggctc ccggacgtcc            50

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agagactcga gtcattagaa gccacagctg ccctccac                         38

<210> SEQ ID NO 8
<211> LENGTH: 20
<212> TYPE: PRT
<213> ORGANISM: Pseudomonas fluorescens

<400> SEQUENCE: 8

Lys Lys Ser Thr Leu Ala Val Ala Val Thr Leu Gly Ala Ile Ala Gln
1               5                   10                  15

Gln Ala Gly Ala
            20

<210> SEQ ID NO 9
<211> LENGTH: 15
<212> TYPE: PRT
<213> ORGANISM: Pseudomonas fluorescens

<400> SEQUENCE: 9

Lys Leu Lys Arg Leu Met Ala Ala Met Thr Phe Val Ala Ala Gly
1               5                   10                  15

<210> SEQ ID NO 10
<211> LENGTH: 19
<212> TYPE: PRT
<213> ORGANISM: Pseudomonas fluorescens

<400> SEQUENCE: 10

Phe Ala Lys Leu Val Ala Val Ser Leu Leu Thr Leu Ala Ser Gly Gln
1               5                   10                  15

Leu Leu Ala

<210> SEQ ID NO 11
<211> LENGTH: 15
<212> TYPE: PRT
<213> ORGANISM: Pseudomonas fluorescens

<400> SEQUENCE: 11

Ile Lys Arg Asn Leu Leu Val Met Gly Leu Ala Val Leu Leu Ser
1               5                   10                  15

<210> SEQ ID NO 12
<211> LENGTH: 22
<212> TYPE: PRT
<213> ORGANISM: Pseudomonas fluorescens
```

```
<400> SEQUENCE: 12

Gln Asn Tyr Lys Lys Phe Leu Leu Ala Ala Ala Val Ser Met Ala Phe
1               5                   10                  15

Ser Ala Thr Ala Met Ala
            20

<210> SEQ ID NO 13
<211> LENGTH: 31
<212> TYPE: PRT
<213> ORGANISM: Pseudomonas fluorescens

<400> SEQUENCE: 13

Met Ile Arg Asp Asn Arg Leu Lys Thr Ser Leu Leu Arg Gly Leu Thr
1               5                   10                  15

Leu Thr Leu Leu Ser Leu Thr Leu Leu Ser Pro Ala Ala His Ser
            20                  25                  30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gccaacgcgg tggccttccc aaccattccc                                              30

<210> SEQ ID NO 15
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
agagactcga gtcattagaa gccacagctg ccctccacag agcggcac                          48

<210> SEQ ID NO 16
<211> LENGTH: 192
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Phe Pro Thr Ile Pro Leu Ser Arg Pro Phe Asp Asn Ala Met Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110
```

```
Asp Leu Leu Lys Asp Leu Glu Glu Gly Ile Gln Thr Leu Met Gly Arg
        115                 120                 125

Leu Glu Asp Gly Ser Pro Arg Thr Gly Gln Ile Phe Lys Gln Thr Tyr
130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190

<210> SEQ ID NO 17
<211> LENGTH: 475
<212> TYPE: DNA
<213> ORGANISM: Homo sapiens
<220> FEATURE:
<221> NAME/KEY: CDS
<222> LOCATION: (27)..(458)

<400> SEQUENCE: 17
agagaactag taaaaaggag aaatcc atg cag ggc caa ttt ttt aga gaa ata      53
                            Met Gln Gly Gln Phe Phe Arg Glu Ile
                             1               5 gaa aac tta aag gag tat ttt aat gca agt agc cca gat gta gct aag     101
Glu Asn Leu Lys Glu Tyr Phe Asn Ala Ser Ser Pro Asp Val Ala Lys
 10              15                  20                  25 ggt ggg cct ctc ttc tca gaa att ttg aag aat tgg aaa gat gaa agt     149
Gly Gly Pro Leu Phe Ser Glu Ile Leu Lys Asn Trp Lys Asp Glu Ser
                 30                  35                  40 gac aaa aaa att att cag agc caa att gtc tcc ttc tac ttc aaa ctc     197
Asp Lys Lys Ile Ile Gln Ser Gln Ile Val Ser Phe Tyr Phe Lys Leu
             45                  50                  55 ttt gaa aac ctc aaa gat aac cag gtc att caa agg agc atg gat atc     245
Phe Glu Asn Leu Lys Asp Asn Gln Val Ile Gln Arg Ser Met Asp Ile
         60                  65                  70 atc aag caa gac atg ttt cag aag ttc ttg aat ggc agc tct gag aaa     293
Ile Lys Gln Asp Met Phe Gln Lys Phe Leu Asn Gly Ser Ser Glu Lys
     75                  80                  85 ctg gag gac ttc aaa aag ctg att caa att ccg gtg gat gat ctg cag     341
Leu Glu Asp Phe Lys Lys Leu Ile Gln Ile Pro Val Asp Asp Leu Gln
 90                  95                 100                 105 atc cag cgc aaa gcc ata aat gaa ctc atc aaa gtg atg aat gac ctg     389
Ile Gln Arg Lys Ala Ile Asn Glu Leu Ile Lys Val Met Asn Asp Leu
                110                 115                 120 tca cca aaa tct aac ctc aga aag cgg aag aga agt cag aat ctc ttt     437
Ser Pro Lys Ser Asn Leu Arg Lys Arg Lys Arg Ser Gln Asn Leu Phe
            125                 130                 135 cga ggc cgg aga gca tca acg taatgactcg agtctct                      475
Arg Gly Arg Arg Ala Ser Thr
        140

<210> SEQ ID NO 18
<211> LENGTH: 834
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(831)
```

<400> SEQUENCE: 18

| | | | | | | | | | | | | | | | | |
|---|---|---|---|---|---|---|---|---|---|---|---|---|---|---|---|---|
| atg | aaa | ctg | aaa | cgt | ttg | atg | gcg | gca | atg | act | ttt | gtc | gct | gct | ggc | 48 |
| Met | Lys | Leu | Lys | Arg | Leu | Met | Ala | Ala | Met | Thr | Phe | Val | Ala | Ala | Gly | |
| 1 | | | | 5 | | | | | 10 | | | | | 15 | | |

| gtt | gcg | acc | gcc | aac | gcg | gtg | gcc | gcc | cag | gtg | cag | ctg | cag | gag | tcg | 96 |
|---|---|---|---|---|---|---|---|---|---|---|---|---|---|---|---|---|
| Val | Ala | Thr | Ala | Asn | Ala | Val | Ala | Ala | Gln | Val | Gln | Leu | Gln | Glu | Ser | |
| | | 20 | | | | | 25 | | | | | 30 | | | | |

| ggc | cca | gga | ctg | gtg | aag | cct | tcg | gag | acc | ctg | tcc | ctc | acc | tgc | act | 144 |
|---|---|---|---|---|---|---|---|---|---|---|---|---|---|---|---|---|
| Gly | Pro | Gly | Leu | Val | Lys | Pro | Ser | Glu | Thr | Leu | Ser | Leu | Thr | Cys | Thr | |
| | 35 | | | | | 40 | | | | | 45 | | | | | |

| gtc | tct | ggt | ggt | tcc | atc | agt | agt | tat | cac | tgg | agc | tgg | atc | cgg | cag | 192 |
|---|---|---|---|---|---|---|---|---|---|---|---|---|---|---|---|---|
| Val | Ser | Gly | Gly | Ser | Ile | Ser | Ser | Tyr | His | Trp | Ser | Trp | Ile | Arg | Gln | |
| 50 | | | | | 55 | | | | | 60 | | | | | | |

| ccc | cca | ggg | aag | gga | ctg | gag | tgg | att | ggg | tat | atc | tat | tac | agt | ggg | 240 |
|---|---|---|---|---|---|---|---|---|---|---|---|---|---|---|---|---|
| Pro | Pro | Gly | Lys | Gly | Leu | Glu | Trp | Ile | Gly | Tyr | Ile | Tyr | Tyr | Ser | Gly | |
| 65 | | | | | 70 | | | | | 75 | | | | | 80 | |

| agc | acc | aac | tac | aac | ccc | tcc | ctc | aag | aat | cga | gtc | acc | ata | tct | gta | 288 |
|---|---|---|---|---|---|---|---|---|---|---|---|---|---|---|---|---|
| Ser | Thr | Asn | Tyr | Asn | Pro | Ser | Leu | Lys | Asn | Arg | Val | Thr | Ile | Ser | Val | |
| | | | | 85 | | | | | 90 | | | | | 95 | | |

| gac | acg | tcc | aag | aac | cag | ttc | tcc | ctg | aac | ctg | agg | tct | gtg | acc | gct | 336 |
|---|---|---|---|---|---|---|---|---|---|---|---|---|---|---|---|---|
| Asp | Thr | Ser | Lys | Asn | Gln | Phe | Ser | Leu | Asn | Leu | Arg | Ser | Val | Thr | Ala | |
| | | | 100 | | | | | 105 | | | | | 110 | | | |

| gca | gac | acg | gcc | gtg | tat | tac | tgt | gcg | cga | gga | acg | tat | ggc | cca | gcc | 384 |
|---|---|---|---|---|---|---|---|---|---|---|---|---|---|---|---|---|
| Ala | Asp | Thr | Ala | Val | Tyr | Tyr | Cys | Ala | Arg | Gly | Thr | Tyr | Gly | Pro | Ala | |
| | | 115 | | | | | 120 | | | | | 125 | | | | |

| gga | gat | gct | ttt | gat | atc | tgg | ggg | caa | ggg | acc | acg | gtc | acc | gtc | tcg | 432 |
|---|---|---|---|---|---|---|---|---|---|---|---|---|---|---|---|---|
| Gly | Asp | Ala | Phe | Asp | Ile | Trp | Gly | Gln | Gly | Thr | Thr | Val | Thr | Val | Ser | |
| | 130 | | | | | 135 | | | | | 140 | | | | | |

| agt | ggt | gga | ggc | ggt | tca | ggc | gga | ggt | ggc | agc | ggc | ggt | ggc | gga | tcg | 480 |
|---|---|---|---|---|---|---|---|---|---|---|---|---|---|---|---|---|
| Ser | Gly | Gly | Gly | Gly | Ser | Gly | Gly | Gly | Gly | Ser | Gly | Gly | Gly | Gly | Ser | |
| 145 | | | | | 150 | | | | | 155 | | | | | 160 | |

| gac | atc | cag | atg | acc | cag | tct | cct | tcc | acc | ctg | tct | gca | tct | att | gga | 528 |
|---|---|---|---|---|---|---|---|---|---|---|---|---|---|---|---|---|
| Asp | Ile | Gln | Met | Thr | Gln | Ser | Pro | Ser | Thr | Leu | Ser | Ala | Ser | Ile | Gly | |
| | | | | 165 | | | | | 170 | | | | | 175 | | |

| gac | aga | gtc | acc | atc | acc | tgc | cgg | gcc | agt | gag | ggt | att | tat | cac | tgg | 576 |
|---|---|---|---|---|---|---|---|---|---|---|---|---|---|---|---|---|
| Asp | Arg | Val | Thr | Ile | Thr | Cys | Arg | Ala | Ser | Glu | Gly | Ile | Tyr | His | Trp | |
| | | | 180 | | | | | 185 | | | | | 190 | | | |

| ttg | gcc | tgg | tat | cag | cag | aag | cca | ggg | aaa | gcc | cct | aaa | ctc | ctg | atc | 624 |
|---|---|---|---|---|---|---|---|---|---|---|---|---|---|---|---|---|
| Leu | Ala | Trp | Tyr | Gln | Gln | Lys | Pro | Gly | Lys | Ala | Pro | Lys | Leu | Leu | Ile | |
| | | 195 | | | | | 200 | | | | | 205 | | | | |

| tat | aag | gcc | tct | agt | tta | gcc | agt | ggg | gcc | cca | tca | agg | ttc | agc | ggc | 672 |
|---|---|---|---|---|---|---|---|---|---|---|---|---|---|---|---|---|
| Tyr | Lys | Ala | Ser | Ser | Leu | Ala | Ser | Gly | Ala | Pro | Ser | Arg | Phe | Ser | Gly | |
| | 210 | | | | | 215 | | | | | 220 | | | | | |

| agt | gga | tct | ggg | aca | gat | ttc | act | ctc | acc | atc | agc | agc | ctg | cag | cct | 720 |
|---|---|---|---|---|---|---|---|---|---|---|---|---|---|---|---|---|
| Ser | Gly | Ser | Gly | Thr | Asp | Phe | Thr | Leu | Thr | Ile | Ser | Ser | Leu | Gln | Pro | |
| 225 | | | | | 230 | | | | | 235 | | | | | 240 | |

| gat | gat | ttt | gca | act | tat | tac | tgc | caa | caa | tat | agt | aat | tat | ccg | ctc | 768 |
|---|---|---|---|---|---|---|---|---|---|---|---|---|---|---|---|---|
| Asp | Asp | Phe | Ala | Thr | Tyr | Tyr | Cys | Gln | Gln | Tyr | Ser | Asn | Tyr | Pro | Leu | |
| | | | | 245 | | | | | 250 | | | | | 255 | | |

| act | ttc | ggc | gga | ggg | acc | aag | ctg | gag | atc | aaa | cgt | gcg | gcc | gca | cat | 816 |
|---|---|---|---|---|---|---|---|---|---|---|---|---|---|---|---|---|
| Thr | Phe | Gly | Gly | Gly | Thr | Lys | Leu | Glu | Ile | Lys | Arg | Ala | Ala | Ala | His | |
| | | | 260 | | | | | 265 | | | | | 270 | | | |

| cac | cat | cat | cac | cat | taa | | | | | | | | | | | 834 |
|---|---|---|---|---|---|---|---|---|---|---|---|---|---|---|---|---|
| His | His | His | His | His | | | | | | | | | | | | |
| | | | 275 | | | | | | | | | | | | | |

<210> SEQ ID NO 19
<211> LENGTH: 277
<212> TYPE: PRT
<213> ORGANISM: Artificial Sequence -continued

```
<220> FEATURE:
<223> OTHER INFORMATION: Description of Artificial Sequence: Synthetic
      polypeptide

<400> SEQUENCE: 19

Met Lys Leu Lys Arg Leu Met Ala Ala Met Thr Phe Val Ala Ala Gly
1               5                   10                  15

Val Ala Thr Ala Asn Ala Val Ala Ala Gln Val Gln Leu Gln Glu Ser
            20                  25                  30

Gly Pro Gly Leu Val Lys Pro Ser Glu Thr Leu Ser Leu Thr Cys Thr
        35                  40                  45

Val Ser Gly Gly Ser Ile Ser Ser Tyr His Trp Ser Trp Ile Arg Gln
50                  55                  60

Pro Pro Gly Lys Gly Leu Glu Trp Ile Gly Tyr Ile Tyr Tyr Ser Gly
65                  70                  75                  80

Ser Thr Asn Tyr Asn Pro Ser Leu Lys Asn Arg Val Thr Ile Ser Val
                85                  90                  95

Asp Thr Ser Lys Asn Gln Phe Ser Leu Asn Leu Arg Ser Val Thr Ala
            100                 105                 110

Ala Asp Thr Ala Val Tyr Tyr Cys Ala Arg Gly Thr Tyr Gly Pro Ala
        115                 120                 125

Gly Asp Ala Phe Asp Ile Trp Gly Gln Gly Thr Thr Val Thr Val Ser
130                 135                 140

Ser Gly Gly Gly Gly Ser Gly Gly Gly Gly Ser Gly Gly Gly Gly Ser
145                 150                 155                 160

Asp Ile Gln Met Thr Gln Ser Pro Ser Thr Leu Ser Ala Ser Ile Gly
                165                 170                 175

Asp Arg Val Thr Ile Thr Cys Arg Ala Ser Glu Gly Ile Tyr His Trp
            180                 185                 190

Leu Ala Trp Tyr Gln Gln Lys Pro Gly Lys Ala Pro Lys Leu Leu Ile
        195                 200                 205

Tyr Lys Ala Ser Ser Leu Ala Ser Gly Ala Pro Ser Arg Phe Ser Gly
    210                 215                 220

Ser Gly Ser Gly Thr Asp Phe Thr Leu Thr Ile Ser Ser Leu Gln Pro
225                 230                 235                 240

Asp Asp Phe Ala Thr Tyr Tyr Cys Gln Gln Tyr Ser Asn Tyr Pro Leu
                245                 250                 255

Thr Phe Gly Gly Gly Thr Lys Leu Glu Ile Lys Arg Ala Ala Ala His
            260                 265                 270

His His His His His
        275

<210> SEQ ID NO 20
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(645)

<400> SEQUENCE: 20 atg aaa ctg aaa cgt ttg atg gcg gca atg act ttt gtc gct gct ggc     48
Met Lys Leu Lys Arg Leu Met Ala Ala Met Thr Phe Val Ala Ala Gly
1               5                   10                  15 gtt gcg acc gcc aac gcg gtg gcc ttc cca acc att ccc tta tcc agg     96
```

```
Val Ala Thr Ala Asn Ala Val Ala Phe Pro Thr Ile Pro Leu Ser Arg
            20                  25                  30 cct ttt gac aac gct atg ctc cgc gcc cat cgt ctg cac cag ctg gcc      144
Pro Phe Asp Asn Ala Met Leu Arg Ala His Arg Leu His Gln Leu Ala
            35                  40                  45 ttt gac acc tac cag gag ttt gaa gaa gcc tat atc cca aag gaa cag      192
Phe Asp Thr Tyr Gln Glu Phe Glu Glu Ala Tyr Ile Pro Lys Glu Gln
 50                  55                  60 aag tat tca ttc ctg cag aac ccc cag acc tcc ctc tgt ttc tca gag      240
Lys Tyr Ser Phe Leu Gln Asn Pro Gln Thr Ser Leu Cys Phe Ser Glu
 65                  70                  75                  80 tct att ccg aca ccc tcc aac agg gag gaa aca caa cag aaa tcc aac      288
Ser Ile Pro Thr Pro Ser Asn Arg Glu Glu Thr Gln Gln Lys Ser Asn
            85                  90                  95 cta gag ctg ctc cgc atc tcc ctg ctc atc cag tcg tgg ctg gag          336
Leu Glu Leu Leu Arg Ile Ser Leu Leu Ile Gln Ser Trp Leu Glu
            100                 105                 110 ccc gtg cag ttc ctc agg agt gtc ttc gcc aac agc ctg gtg tac ggc      384
Pro Val Gln Phe Leu Arg Ser Val Phe Ala Asn Ser Leu Val Tyr Gly
            115                 120                 125 gcc tct gac agc aac gtc tat gac ctc cta aag gac cta gag gaa ggc      432
Ala Ser Asp Ser Asn Val Tyr Asp Leu Leu Lys Asp Leu Glu Glu Gly
130                 135                 140 atc caa acg ctg atg ggg agg ctg gaa gat ggc agc ccc cgg act ggg      480
Ile Gln Thr Leu Met Gly Arg Leu Glu Asp Gly Ser Pro Arg Thr Gly
145                 150                 155                 160 cag atc ttc aag cag acc tac agc aag ttc gac aca aac tca cac aac      528
Gln Ile Phe Lys Gln Thr Tyr Ser Lys Phe Asp Thr Asn Ser His Asn
            165                 170                 175 gat gac gca cta ctc aag aac tac ggg ctg ctc tac tgc ttc agg aag      576
Asp Asp Ala Leu Leu Lys Asn Tyr Gly Leu Leu Tyr Cys Phe Arg Lys
            180                 185                 190 gac atg gac aag gtc gag aca ttc ctg cgc atc gtg cag tgc cgc tct      624
Asp Met Asp Lys Val Glu Thr Phe Leu Arg Ile Val Gln Cys Arg Ser
            195                 200                 205 gtg gag ggc agc tgt ggc ttc taa                                      648
Val Glu Gly Ser Cys Gly Phe
            210                 215

<210> SEQ ID NO 21
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Lys Leu Lys Arg Leu Met Ala Ala Met Thr Phe Val Ala Gly
1               5                   10                  15

Val Ala Thr Ala Asn Ala Val Ala Phe Pro Thr Ile Pro Leu Ser Arg
            20                  25                  30

Pro Phe Asp Asn Ala Met Leu Arg Ala His Arg Leu His Gln Leu Ala
            35                  40                  45

Phe Asp Thr Tyr Gln Glu Phe Glu Glu Ala Tyr Ile Pro Lys Glu Gln
 50                  55                  60

Lys Tyr Ser Phe Leu Gln Asn Pro Gln Thr Ser Leu Cys Phe Ser Glu
 65                  70                  75                  80
```

-continued

```
Ser Ile Pro Thr Pro Ser Asn Arg Glu Glu Thr Gln Gln Lys Ser Asn
            85                  90                  95

Leu Glu Leu Leu Arg Ile Ser Leu Leu Leu Ile Gln Ser Trp Leu Glu
        100                 105                 110

Pro Val Gln Phe Leu Arg Ser Val Phe Ala Asn Ser Leu Val Tyr Gly
    115                 120                 125

Ala Ser Asp Ser Asn Val Tyr Asp Leu Leu Lys Asp Leu Glu Glu Gly
130                 135                 140

Ile Gln Thr Leu Met Gly Arg Leu Glu Asp Gly Ser Pro Arg Thr Gly
145                 150                 155                 160

Gln Ile Phe Lys Gln Thr Tyr Ser Lys Phe Asp Thr Asn Ser His Asn
                165                 170                 175

Asp Asp Ala Leu Leu Lys Asn Tyr Gly Leu Leu Tyr Cys Phe Arg Lys
            180                 185                 190

Asp Met Asp Lys Val Glu Thr Phe Leu Arg Ile Val Gln Cys Arg Ser
        195                 200                 205

Val Glu Gly Ser Cys Gly Phe
    210                 215
```

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gctctagagg aggtaactta tgaaactgaa acg         33

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gggaatggtt gggaaggcca ccgcgttggc            30

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ctgcacctgg gcggccaccg cgtt                  24

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 25
aaccgcggtg gccgcccagg tgcag                                          25

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
acgcgtcgac ttattaatgg tg                                             22

<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
atgatggtga tgtgcggccg cacgtttgat c                                   31

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Met Cys Tyr Cys Gln Asp Pro
1               5

<210> SEQ ID NO 29
<211> LENGTH: 144
<212> TYPE: PRT
<213> ORGANISM: Homo sapiens

<400> SEQUENCE: 29

Met Gln Gly Gln Phe Phe Arg Glu Ile Glu Asn Leu Lys Glu Tyr Phe
1               5                   10                  15

Asn Ala Ser Ser Pro Asp Val Ala Lys Gly Gly Pro Leu Phe Ser Glu
            20                  25                  30

Ile Leu Lys Asn Trp Lys Asp Glu Ser Asp Lys Lys Ile Ile Gln Ser
        35                  40                  45

Gln Ile Val Ser Phe Tyr Phe Lys Leu Phe Glu Asn Leu Lys Asp Asn
    50                  55                  60

Gln Val Ile Gln Arg Ser Met Asp Ile Ile Lys Gln Asp Met Phe Gln
65                  70                  75                  80

Lys Phe Leu Asn Gly Ser Ser Glu Lys Leu Glu Asp Phe Lys Lys Leu
                85                  90                  95

Ile Gln Ile Pro Val Asp Asp Leu Gln Ile Gln Arg Lys Ala Ile Asn
            100                 105                 110

Glu Leu Ile Lys Val Met Asn Asp Leu Ser Pro Lys Ser Asn Leu Arg
        115                 120                 125

Lys Arg Lys Arg Ser Gln Asn Leu Phe Arg Gly Arg Arg Ala Ser Thr
    130                 135                 140
```

EXPRESSION OF MAMMALIAN PROTEINS IN *PSEUDOMONAS FLUORESCENS*

REFERENCE TO PRIOR APPLICATIONS

This application claims priority to U.S. Provisional Application No. 60/564,798, entitled "Expression of Mammalian Proteins in *Pseudomonas fluorescens*," filed Apr. 22, 2004, and No. 60/537,148, entitled "Protein Expression Systems," filed Jan. 16, 2004. This application is also a continuation-in-part of U.S. application Ser. No. 10/681,540, entitled "Amended Recombinant Cells for the Production and Delivery of Gamma Interferon as an Antiviral Agent, Adjuvant And Vaccine Accelerant," filed Oct. 7, 2003, now U.S. Pat. No. 7,338,794 which claims priority to U.S. Provisional Application No. 60/417,124, filed Oct. 8, 2002.

SEQUENCE LISTING

The instant application contains a Sequence Listing which has been submitted electronically in ASCII format and is hereby incorporated by reference in its entirety. Said ASCII copy, created on Jan. 14, 2015, is named 38194-703.501_SL.txt and is 34,547 bytes in size.

FIELD OF THE INVENTION

The invention is a process for improved production of a recombinant mammalian protein by expression in a Pseudomonad, particularly in a *Pseudomonas fluorescens* organism. The process improves production of mammalian protein expression over known expression systems.

BACKGROUND OF THE INVENTION

More than 325 million people worldwide have been helped by the more than 155 biotechnology drugs and vaccines approved by the U.S. Food and Drug Administration (FDA). In addition, there are more than 370 biotech drug products and vaccines currently in clinical trials targeting more than 200 diseases, including various cancers, Alzheimer's disease, heart disease, diabetes, multiple sclerosis, AIDS and arthritis. Unlike traditional small molecule therapeutics that are produced through classical chemical synthesis, proteins are ususally produced in living cells inefficiently and at high cost. Due to the high cost and complexity, there is a shortage of manufacturing capacity for protein-based therapeutics.

The use of microbial cells to produce products has a very long history. As early as 1897, Buchner discovered that enzymes extracted from yeast are effective in converting sugar into alcohol, leading to the production of key industrial chemicals using microorganisms. By the 1940s, large-scale production of penicillin via fermentation was achieved. Techniques for the insertion of foreign genes into bacteria were first developed in the early 1970s. Bacterial production of commercially viable recombinant mammalian protein was first exploited in the production of human insulin (Goeddel, et al., 1979a; Wong, 1997). Today fermentation and cell culture underlie the bulk of the industry's production of alcohol, antibiotics, biochemicals and therapeutic proteins. However, development and manufacturing of therapeutically useful proteins has been hampered due, in large part, to the limitations of the current organisms used to express these exogenous proteins.

Prokaryotic vs. Eukaryotic Protein Expression

Although bacterial expression system are often used to produce recombinant eukaryotic proteins, typically the proteins yielded differ significantly from their original counterparts. In general, it is a challenge to reproduce the eukaryotic secondary and tertiary structures in *E. coli* expression systems. At the same time, while the eukaryotic expression systems currently are better able to form the secondary and tertiary structures of recombinant eukaryotic proteins, the capacity of these systems to produce recombinant proteins in large quantity is limited.

Post-translational modifications represent the most significant differences between prokaryotic and eukaryotic protein expression. Prokaryotes (i.e., bacteria) have a very simply cellular structure and no membrane-bound organelles. In eukaryotes, a protein is often modified after it is intially produced. These modifications, in many cases, are necessary to convert the peptide into a functional form. Thus, even when exisiting bacterial expression systems produce a protein with the correct primary structure, the protein may not be post-translationally modified and is therefore often nonfunctional. Common modifications include disulfide bond formation, glycosylation, acetylation, acylation, phosphorylation, and gamma-carboxylation, all of which can regulate protein folding and biological activity. Bacterial expression systems generally do not properly glycosylate, acetylate, acylate, phosphorylate, or gamma-carboxylate eukaryotic proteins.

Bacteria, such as *E. coli*, can form disulfide bonds, but the bonds are often formed in the incorrect configuration required for biological activity; therefore, denaturation and refolding is usually required to produce active eukaryotic proteins. Molecular chaperone proteins are present in both prokaryotes and eukaryotes that facilitate the folding of other proteins. In the absence of such chaperones, unfolded or partially folded polypeptide chains are unstable within the cell, frequently folding incorrectly or aggregating into insoluble complexes. The binding of chaperones stabilizes these unfolded polypeptides, thereby preventing incorrect folding or aggregation and allowing the polypeptide chain to fold into its correct conformation. However, chaperones differ in each type of cell, and can be differentially expressed based on extracellular conditions.

Problems with Current Expression Systems

*Escherichia coli* (*E. coli*) is the most widely and routinely used protein expression system. Production in *E. coli* is inexpensive, fast, and well characterized. Further, scale-up and harvesting is possible and cGMP production is well established. However, there are significant limitations to the use of *E. coli*, which often prove difficult to overcome, particularly when expressing recombinant mammalian proteins.

Along with the limitations described above, the high-level expression of recombinant gene products in *E. coli* often results in the misfolding of the protein of interest and its subsequent degradation by cellular proteases or deposition into biologically inactive aggregates known as inclusion bodies. Protein found in inclusion bodies typically must be extracted and renautred for activity, adding time and expense to the process. Typical renaturation methods involve attempts to dissolve the aggregate in concentrated denaturant, and subsequent removal of the denaturant by dilution. Some of the factors which have been suggested to be involved in inclusion body formation include the high local concentration of protein; a reducing environment in the cytoplasm (*E. coli* cytoplasm has a high level of glutathione) preventing formation of disulfide bonds; lack of post-translational modifications, which can increase the protein solubility; improper interactions with chaperones and other enzymes involved in in vivo folding; intermolecular cross-linking via disulfide or other covalent bonds; and increased aggregation of folding intermediates due to their limited solubility. It is probably a combination of these factors, as well as a limited availability of chaperones, which most commonly lead to the formation of inclusion bodies.

Yeast expression systems, such as *Saccharomyces cerevisiae* or *Pichia pastoris*, are also commonly used to produce proteins. These systems are well characterized, provide good expression levels and are relatively fast and inexpensive compared to other eukaryotic ecpression systems. However, yeast can accomplish only limited post-translational protein modifications, the protein may need refolding, and harvesting of the protein can be a problem due to the characteristics of the cell wall.

Insect cell expression systems have also emerged as an attractive, but expensive, alternative as a protein expression system. Correctly folded proteins that are generally post-translationally modified can sometimes be produced and extracellular expression has been achieved. However, it is not as rapid as bacteria and yeast, and scale-up is generally challenging.

Mammalian cell expression systems, such as Chinese hamster ovary cells, are often used for complex protein expression. This system usually produces correctly folded proteins with the appropriate post-translational modifications and the proteins can be expressed extracellularly. However, the system is very expensive, scale-up is slow and often not feasible, and protein yields are lower than in any other system.

*Pseudomonas fluorescens* (*P. fluorescens*)

*Pseudomonas fluorescens* encompasses a group of common, nonpathogenic saprophytes that colonize soil, water and plant surface environments. *P. fluorescens* are extensively used in agricultural and industrial processes, including commercially for the production of non-mammalian industrial and agricultural proteins. Nonmammalian enzymes derived from *P. fluorescens* have been used to reduce environmental contamination, as detergent additives, and for stereoselective hydrolysis. Mycogen began expressing recombinant bacterial proteins in *P. fluorescens* in the mid-1980's and filed its first patent application on the expression of the *Bacillus thuringiensis* toxin in *P. fluorescens* on Jan. 22, 1985 ("Cellular encapsulation of biological pesticides"). Between 1985 and 2004, Mycogen, later Dow Agro Sciences, as well as other companies, capitalized on the agricultural use of *P. fluorescens* in patent applications on the production of pesticidal, insecticidal, and nematocidal toxins, as well as on specific toxic sequences and genetic manipulation to enhance expression of these. Examples of patent applications directed to the expression of recombinant bacterial proteins in *P. fluorescens* include: U.S. Pat. Nos. 3,844,893; 3,878,093, 4,169,010; 5,292,507; 5,558,862; 5,559,015; 5,610,044; 5,622,846; 5,643,774; 5,662,898; 5,677,127; 5,686,282; 3,844,893; 3,878,093; 4,169,010; 5,232,840; 5,292,507; 5,558,862; 5,559,015; 5,610,044; 5,622,846; 5,643,774; 5,662,898; 5,677,127; 5,686,282; 5,686,283; 5,698,425; 5,710,031; 5,728,574; 5,731,280; 5,741,663; 5,756,087; 5,766,926; 5,824,472; 5,869,038; 5,891,688; 5,952,208; 5,955,348; 6,051,383; 6,117,670; 6,184,440; 6,194,194; 6,268,549; 6,277,625; 6,339,172; 6,447,770; as well as PCT Publication Nos. WO 00/15761; WO 00/29604; WO 01/27258; WO 02/068660; WO 02/14551; WO 02/16940; WO 03/089455; WO 04/006657; WO 04/011628; WO 87/05937; WO 87/05938; WO 95/03395; WO 98/24919; WO 99/09834; and WO 99/53035.

On Oct. 8, 2003, Dow AgroSciences filed PCT Publication No. 04/087864 entitled, "Amended Recombinant Cells (ARCs) for the Production and Delivery of Antiviral Agents, Adjuvants and Vaccine Accelerants". The application describes recombinant cells that can include at least one heterologous gene encoding a chemokine or a cytokine and the administration of such cells to a host to accelerate an immune response. The application demonstrates the production of bovine interferon-$\alpha$ and interferon-$\gamma$ in *P. fluorescens*.

Dow Global Technologies currently has several pending patent applications in the area of use of *P. fluorescens* to produce recombinant proteins. PCT Application WO 03/068926 to Dow Global Technologies, filed Feb. 13, 2003, entitled, "Over-Expression of Extremozyme Genes in *Pseudomonas* and Closely Related Bacteria" describes an expression system in which pseudomonads, specifically *P. fluorescens*, can be used as host cells for the production of extremozyme enzymes. These enzymes are typically ancient, found in prokaryotes, eukaryotes including fungi, yeast, lichen, protists and protozoa, algae and mosses, tardigrades and fish. The patent discloses that enzymes can be derived from certain extremophilic fungi and yeast, but are typically derived from extremophilic bacteria.

PCT publication No. WO 03/089455 to Dow Global Technologies, filed Apr. 22, 2003, entitled "Low-Cost Production of Peptides" describes a method of producing small peptides, primarily antimicrobial peptides, as concatameric precursors in Pseudomonads, specifically *P. fluorescens*.

PCT publication No. WO 04/005221 to Dow Global Technologies, entitled "Benzoate and Antranilate Inducible Promoters" provides novel benzoate- or anthranilate-inducible promoters from *P. fluorescens*, as well as novel tandem promoters, variants and improved mutants thereof, that are useful for commercial prokaryotic fermentation systems.

U.S. Pat. No. 5,232,840 to Monsanto Co. describes the use of novel ribosomal binding sites to enhance expression of certain proteins in prokaryotic cells. In one example, the cells are used to express porcine growth hormone in several organisms, including *E. coli*, *P. fluorescens*, and *P. putida*. The data shows that *P. fluorescens* is less efficient at expressing the growth hormone when compared to *E. coli*. In contrast, when expressing a bacterial protein, *P. fluorescens* is much more effective at protein production than *E. coli* under comparable conditions. In fact, *P. fluorescens* cells described in this patent produce several-fold more bacterially-derived $\beta$-galactosidase than *E. coli* (compare table 4 to tables 1 and 2).

While progress has been made in the production of proteins of commercial interest, a strong need remains to improve the capability and production level of recombinant mammalian, and in particular human, proteins.

Therefore, it is an object of the present invention to provide a process for the production of recombinant mammalian, in particular human, proteins that can be isolated and purified for therapeutic use, and cells which can accomplish this process.

It is a further object of the present invention to provide improved processes for the production of active recombinant mammalian proteins, including complex mammalian proteins.

It is a further object of the present invention to provide improved processes for the production of high levels of recombinant mammalian, in particular human, proteins.

It is a further object of the present invention to provide transformed organisms that provide high expression levels of soluble or insoluble recombinant mammalian proteins.

SUMMARY OF THE INVENTION

It has been discovered that *Pseudomonas fluorescens* is a superior organism for the production of recombinant proteins, and in particular recombinant mammalian proteins, such as recombinant human proteins. Based on these discoveries, the present invention provides a process of producing recombinant mammalian or mammalian-derived proteins in *P. fluorescens*. In addition, the invention provides *P. fluorescens* transformed to produce recombinant mammalian, including human, proteins.

In one embodiment, the invention provides a process of producing a mammalian protein in a *P. fluorescens* organism in which the protein is produced at a higher level or concentration per cell or per liter of fermentation reaction than in an *E. coli* organism under comparable conditions. In yet another embodiment, the invention provides a process of producing mammalian proteins in an *P. fluorescens* organism in a batch culture which produces higher amounts of protein per liter than a corresponding batch of recombinant *E. coli* organisms.

Comparable conditions or substantially comparable conditions particularly refers to expression of recombinant protein using the same operably linked transcriptional promoter and ribosomal binding site in different organisms, and using the same initial induction conditions. Comparable conditions can further include using the same vector and associated regulatory elements, including, but not limited to, enhancer sequences, termination sequences, and origin or replication sequences. Comparable conditions can also include the same total volume of cell fermentation reaction. Comparable conditions can also include the same concentration of total cells per liter of reaction. In one embodiment, the conditions also include total induction times (before measurement) that are similar or the same. However, in another embodiment, the induction times can vary depending on the organism. Specifically, *P. fluorescens* has a capacity for increased growth time over *E. coli* without reducing protein production, such that protein production can be measured in *P. fluorescens* at a time point at which *E. coli* cells are largely silent. One way to measure the comparable conditions is to compare the percentage of recombinant protein per total cell protein. The comparable conditions also do not require identical media for growth. The media can be adjusted to ensure optimal production for the individual organisms.

In another embodiment, the invention provides a process for producing recombinant mammalian proteins by producing the proteins in a *P. fluorescens* organism and isolating the produced protein. In one sub-embodiment, the process includes substantially purifying the protein. In one embodiment, the protein is derived from a human protein, or is humanized.

The invention also provides the use of *P. fluorescens* in at least the following embodiments:
- (i) the production of recombinant mammalian, including human, proteins present in the cell in a range of between 1 and 75 percent total cell protein (% tcp), or in particular, at least greater than approximately 5% tcp, 10% tcp, at least 15% tcp, at least 20% tcp or more;
- (ii) the production of recombinant mammalian, including human, proteins that are soluble and present in the cytoplasm of the cell in a range of between 1 and 75% tcp or in particular, at least greater than approximately 5% tcp, 10% tcp, at least 15% tcp, at least 20% tcp or more;
- (iii) the production of recombinant mammalian, including human, proteins that are insoluble in the cytoplasm of the cell, in a range of between 1 and 75% tcp or in particular, at least greater than approximately 5% tcp, 10% tcp, at least 15% tcp, at least 20% tcp or more;
- (iv) the production of recombinant mammalian, including human, proteins that are soluble in the periplasm of the cell in a range of between 1 and 75% tcp or in particular, at least greater than approximately 5% tcp, 10% tcp, at least 15% tcp, at least 20% tcp or more;
- (v) the production of recombinant mammalian, including human, proteins that are insoluble in the periplasm in a range of between 1 and 75% tcp or in particular, at least greater than approximately 5% tcp, 10% tcp, at least 15% tcp, at least 20% tcp or more;
- (vi) the production or recombinant mammalian, including human, proteins in the cell in a range of between 1 and 75% tcp, or particularly at least greater than approximately 5% tcp, 10% tcp, at least 15% tcp, at least 20% tcp or more, when grown at a cell density of at least 40 g/L;
- (vii) the production of recombinant mammalian, including human, proteins present in the cell in an active form;
- (viii) the production of multi-subunit recombinant mammalian, including human, proteins in active form;
- (ix) the production of recombinant mammalian, including human, proteins that are then isolated and purified; and
- (x) the production of recombinant mammalian, including human, proteins that are renatured.

In one embodiment, the recombinant mammalian protein is selected from the group consisting of a multi-subunit protein, a blood carrier protein, an enzyme, a full length antibody, an antibody fragment, or a transcriptional factor.

In another embodiment, the invention includes:
- (i) *Pseudomonas fluorescens* organisms that are transformed to produce recombinant mammalian, including human, proteins at a higher level or concentration than a corresponding *E. coli* organism when grown under substantially corresponding conditions;
- (ii) *Pseudomonas fluorescens* organisms that are transformed to produce recombinant mammalian, including human, proteins and peptides that are present in the cell in a range of between 1 and 75% tcp or in particular, at least greater than approximately 5% tcp, 10% tcp, at least 15% tcp, at least 20% tcp or more;
- (iii) *Pseudomonas fluorescens* organisms that are transformed to produce recombinant mammalian, including human, proteins that are present in the cell in active form;
- (iv) *Pseudomonas fluorescens* organisms that are transformed to produce recombinant mammalian, including human, proteins that are soluble in the cytoplasm of the cell in a range of between 1 and 75% tcp or in particular, at least greater than approximately 5% tcp, 10% tcp, at least 15% tcp, at least 20% tcp or more;
- (v) *Pseudomonas fluorescens* organisms that are transformed to produce recombinant mammalian, including human, proteins that are insoluble in the cytoplasm of the cell in a range of between 1 and 75% tcp or in particular, at least greater than approximately 5% tcp, 10% tcp, at least 15% tcp, at least 20% tcp or more;
- (vi) *Pseudomonas fluorescens* organisms that are transformed to produce recombinant mammalian, including human, proteins that are soluble in the periplasm of the cell in a range of between 1 and 75% tcp or in, particular, at least greater than approximately 5% tcp, 10% tcp, at least 15% tcp, at least 20% tcp or more;

(vii) *Pseudomonas fluorescens* organisms that are transformed to produce recombinant mammalian, including human, proteins that are insoluble in the periplasm of the cell in a range of between 1 and 75% tcp or in particular, at least greater than approximately 5% tcp, 10% tcp, at least 15% tcp, at least 20% tcp or more;

(viii) *Pseudomonas fluorescens* organisms that are transformed to produce multi-subunit recombinant mammalian, including human, proteins;

(ix) *Pseudomonas fluorescens* organisms that are transformed to produce multi-subunit recombinant mammalian, including human, proteins present in the cell in active form.

In an alternative embodiment, a *Pseudomonas* organisms and closely related bacteria other than fluorescens are used as host cells in this invention, as described in more detail below. In one embodiment, the host cell will be selected generally from the genus *Pseudomonas* and specifically from a nonpathogenic *Pseudomonas* species. Likewise, any *Pseudomonas fluorescens* strain can be used that accomplishes the desired inventive goal, including but not limited to strain MB101, or a strain that is modified to include at least one host-cell-expressible, inserted copy of at least one Lac repressor protein-encoding lacI transgene, such as MB214 and MB217. The *Pseudomonas* organism can also optionally be genetically modified to add or delete one or more genes to improve performance, processing, or other characteristics.

In one embodiment, the *Pseudomonas* organism is transformed with a nucleic acid encoding a recombinant mammalian protein selected from the group consisting of a multi-subunit protein, a blood carrier protein, an enzyme, a full length antibody, an antibody fragment, or a transcriptional factor. In one embodiment, the *P. fluorescens* organism expresses a recombinant mammalian protein selected from the group consisting of a multi-subunit protein, a blood carrier protein, an enzyme, a full length antibody, an antibody fragment, or a transcriptional factor.

The expressed recombinant mammalian or human protein will typically have a mass of at least about 1 kD, and up to about 100, 200, 300, 400 or 500 kD, often between about 10 kD and about 100 kD, and usually greater than about 30 kD.

BRIEF DESCRIPTION OF THE FIGURES

FIG. 7 shows that all the transformants selected had the desired interferon insert, as verified by sequencing the inserted DNA. The sequence of the inserted DNA (SEQ ID NO: 17) encodes an amino acid sequence (SEQ ID NO: 29).

FIG. 8 represents the nucleotide sequence for the phosphate binding protein-gal2 single chain antibody fusion protein. The sequence of the DNA (SEQ ID NO : 18) encodes an amino acid sequence (SEQ ID NO: 19).

FIG. 9 represents the amino acid sequence for the phosphate binding protein-gal2 single chain antibody fusion protein.

FIG. 10 represents the nucleotide sequence for the phosphate binding protein-human growth hormone fusion protein.The sequence of the DNA (SEQ ID NO: 20) encodes an amino acid sequence (SEQ ID NO: 21).

FIG. 11 represents the amino acid sequence for the phosphate binding protein-human growth hormone fusion protein.

DETAILED DESCRIPTION OF THE INVENTION

Process for Producing Recombinant Mammalian Proteins

Figure 1:
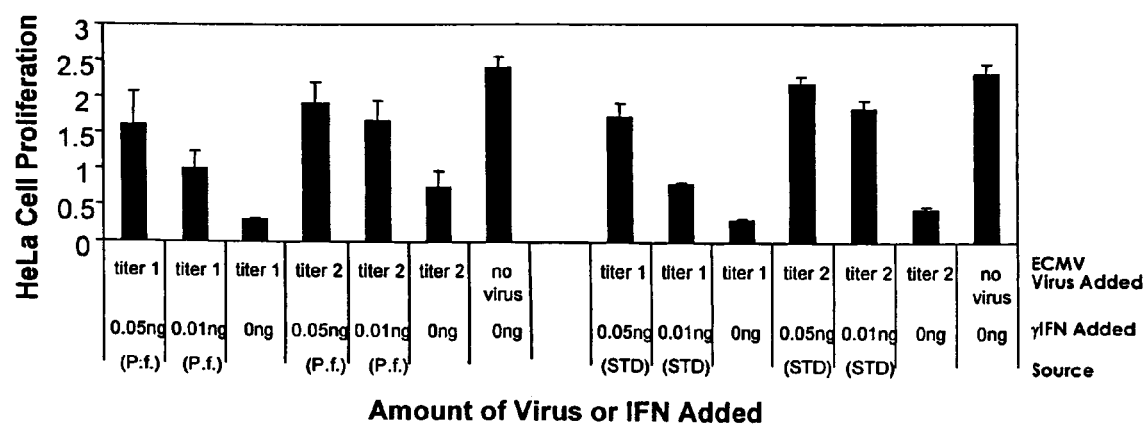
FIG. 1 is a graph showing hu-γ-IFN purified from the soluble fraction of *P. fluorescens* samples displays activity comparable to a commercially available standard.

The invention provides processes and transformed *Pseudomonas fluorescens* organisms that produce recombinant mammalian proteins.

In one embodiment, the invention provides a process for producing recombinant mammalian proteins by producing the proteins in a *P. fluorescens* organism and isolating the produced protein. The protein can be isolated after expression by techniques known in the art, including, but not limited to, affinity chromatography, ion-exchange chromatography, antibody affinity, size-exclusion, or any other method that eliminates a substantial portion of the cellular debris from the protein. In one sub-embodiment, the process provides a substantially purified protein. The isolated protein can have activity similar to that of the native protein that it is derived from. The protein can be isolated in a correctly folded state or conformation, approximating that of the native protein, or can be further renatured or modified to put it into a correctly folded conformation. In one sub-embodiment, the protein is derived from a human protein, or is humanized. A "humanized" protein is typically a chimeric mammalian-type protein which is partially comprised of a human-derived protein sequence. Humanization is particularly useful in antibody production and the development of humanized antibodies has been extensively described, for example in U.S. Pat. No. 6,800,738.

In one embodiment, expression of the protein by the host cell is followed by isolation of the protein. In another embodiment, the protein of peptide is purified. In an alternative embodiment, the protein is purified following isolation of the protein. Optionally the isolated or purified protein can be renatured or refolded in order to produce active proteins.

In another embodiment, the invention provides a process of producing a mammalian protein in a *P. fluorescens* organism in which the protein is produced at a higher level or concentration than in an *E. coli* organism. The suitability of *P. fluorescens* organisms for high level production of mammalian proteins was unexpected based on the lack of success in producing such proteins in these organisms in the prior art. The present inventors have found that these organisms are indeed capable of high levels of production of mammalian proteins, and typically express protein in higher yield or at higher levels than *E. coli* when tested in corresponding assays. In another embodiment, the invention provides a process of producing mammalian proteins in an *P. fluorescens* organism in a batch culture which produces higher amounts of protein per liter than a corresponding batch of recombinant *E. coli* organisms.

In some embodiments, processes are provided that include producing recombinant mammalian, including human, multi-subunit proteins in active form in *P. fluorescens*; producing recombinant mammalian blood carrier proteins, including human blood carrier proteins such as transferrin and albumin in *P. fluorescens*; producing recombinant mammalian enzymes, including recombinant mammalian enzymes in active form in *P. fluorescens*; producing antibodies and antibody fragments, including single chain antibodies and Fab fragments in *P. fluorescens*; and producing recombinant mammalian, including human, transcriptional factors in *P. fluorescens*.

In one embodiment, the recombinant mammalian protein is produced as a multimer, or in a concatameric precursor, for example, in the form of at least two small peptide (1-15 amino acids) units in tandem. In an alternative embodiment, the recombinant mammalian protein is not produced as a multimer, or in concatameric precursors, but instead is produced as a single chain polypeptide.

Screening of Biomolecules

A separate embodiment of the present invention provides *P. fluorescens* organisms in a process of screening libraries of mammalian biomolecules to identify at least one that exhibits a desired activity or property. The *P. fluorescens* cells can be transformed with a number of mammalian derived nucleic acids for which testing is desired, producing a library of transformed host cells. Upon expression, polypeptides encoded by at least some of the nucleic acids are produced for testing either in cytoplasm or following recovery from the cell. Examples of activities and properties for which testing may be performed include: polypeptide expression level; polypeptide stability; and biocatalytic activities and properties. Illustrative examples of biocatalytic activities and properties include: enzymatic activities; protein interactions/binding; protein stabilization; substrate usage; product formation; reaction conditions, such as pH, salinity, or reaction temperature; biocatalytic parameters for a given catalyzed reaction, such as Km and Vmax; and stability behavior, such as thermostability and biocatalyst half-life. The test results obtained may be used to selected library member(s) for further development.

Protein Expression

A key aspect of this invention is the expression of high levels of recombinant mammalian, for example human, proteins in a range of between 1 and 75 percent total cell protein (% tcp) by expression in *P. fluorescens* organisms. The expressed proteins can be soluble or insoluble while in the *P. fluorescens* cell. Such high levels of soluble or insoluble recombinant mammalian proteins can be an improvement over previously known mammalian protein expression systems. In particular, high levels of recovered mammalian proteins in large scale fermentation reactions are not typically possible with known techniques.

In one embodiment, the invention provides expression levels of mammalian proteins that exceed those found in *E. coli* expression systems. In one embodiment, the concentration of recombinant protein in each cell is higher than that found in *E. coli* in comparative assays. In one embodiment, the level of recombinant protein as compared to total cell protein measured in the *P. fluorescens* expression system is higher than that of the same recombinant protein expressed in *E. coli*. In another embodiment, the level or amount of soluble protein in the *P. fluorescens* expression system described herein is higher than the level or amount of soluble recombinant protein in a comparable *E. coli* expression system. In another embodiment, the total amount of active protein is higher than the amount derived from an *E. coli* expression system. In a separate embodiment, the level of recombinant active protein as compared to total cell protein measured in the *P. fluorescens* expression system is higher than that of the same recombinant protein expressed in *E. coli*. In one embodiment, the level, concentration, or amount of protein expressed in *P. fluorescens* is at least 2×, at least 3×, at least 4×, at least 5×, at least 6×, at least 7×, at least 8×, at least 9×, at least 10×, or more the level, concentration, or amount of recombinant protein expressed in *E. coli* in comparable assays.

One of the benefits of *P. fluorescens* as an expression system is that the cells can be grown in large scale cultures without negatively impacting their capacity for protein production. This capacity exceeds that found in other bacterial systems, such as *E. coli*. In another embodiment, the process includes producing mammalian proteins in batch cultures in which the recombinant protein is produced at a higher total level in *P. fluorescens* than in *E. coli* batch cultures. In yet another embodiment, the invention provides a process of producing mammalian proteins in an *P. fluorescens* organism in a batch culture which produces higher amounts of protein per liter than a corresponding batch of recombinant *E. coli* organisms.

The invention generally provides processes and transformed *P. fluorescens* organisms that afford expression levels of 1-75% total cell protein (tcp) of soluble or insoluble recombinant mammalian proteins. The recombinant mammalian proteins expressed in the cell can be expressed in an active form. In other embodiments, the *P. fluorescens* provides at least 1, 5, 10, 15, 20, 25, 30, 40, 50, 55, 60, 65, 70, or 75% tcp of recombinant mammalian proteins.

These proteins can be soluble, and when soluble, can be present in the cytoplasm or periplasm of the cell during production. Soluble proteins are readily released from the cell by methods including, but not limited to, rupturing of the cell membrane by pressure (i.e. the "French" press method), or by lysozyme degradation of the cell membrane. Cells can typically also be lysed using detergents, such as non-ionic detergents. Proteins that are soluble can be further stabilized by adjusting components of the buffer, such as buffer pH, salt concentrations, or additional protein components (for example, in multi-subunit complexes). The soluble proteins can be isolated or purified from other protein and cellular debris by, for example, centrifugation and/or chromatography such as size exclusion, anion or cation exchange, or affinity chromatography.

The proteins can also be insoluble. Insoluble proteins are typically found in inclusion bodies in the cytoplasm, but are also often in the periplasm. Not all insoluble proteins are in inclusion bodies, and can also be found in membrane aggregates, as small protein aggregates or in any other insoluble form in the cytoplasm or periplasm. Insoluble proteins can typically be renatured using, for example, reducing agents such as urea or guanidine hydrochloride. Insoluble proteins or protein aggregates can be isolated, for example, by centrifugation and/or chromatography such as size exclusion chromatography. Proteins in insoluble aggregates can typically be separated by solubilization of the aggregates using, for example, micelles or reverse micelles as described in Vinogradov, et al. (2003) *Anal Biochem.* 15; 320 (2):234-8.

In a particular embodiment, the *Pseudomonas* host cell can have a recombinant mammalian peptide, polypeptide, protein, or fragment thereof expression level of at least 1% tcp and a cell density of at least 40 g/L, when grown (i.e. within a temperature range of about 4° C. to about 55° C., inclusive) in a mineral salts medium. In a particular embodiment, the expression system will have a recombinant protein of peptide, including recombinant mammalian protein, expression level of at least 5% tcp and a cell density of at least 40 g/L, when grown (i.e. within a temperature range of about 4° C. to about 55° C., inclusive) in a mineral salts medium at a fermentation scale of at least 10 Liters.

Expression levels can be measured by standard techniques known in the art. In one embodiment, the amount of protein (in grams) is compared to the amount in grams of total cell protein in a given sample. In another embodiment, the measurement is a level of recombinant protein per liter. In another embodiment, the level or amount can be measured as compared to a known standard, such as a BSA control. The level or amount of recombinant protein can be measured, for example, by analyzing the light absorbtion of a purified protein, by measuring an affinity of a marker for the protein (such as an antibody affinity) and comparing that to a known standard, or by measuring the level of activity compared to a known standard (such as a known amount of purified, active protein).

It has been found that, in certain situations, no additional disulfide-bond-promoting conditions or agents are required in order to recover disulfide-bond-containing target polypeptides in active, soluble form, when a *Pseudomonas fluorescens* bacteria is used as the expression host cell. Therefore, in one embodiment, the transgenic peptide, polypeptide, protein, or fragment contains at least one intramolecular disulfide bond in its native state. In other embodiments, the protein can contain up to 2, 4, 6, 8, 10, 12, 14, 16, 18, or 20 or more disulfide bonds in its native state.

In some embodiments, the protein is expressed or found in the periplasm of the cell during production before purification or isolation. The protein can be secreted into the periplasm by being fused to an appropriate signal secretion sequence. In one embodiment, the signal sequence is a signal sequence that is native to the *P. fluorescens* genome. In specific embodiments, the signal sequence is a phosphate binding protein, a Lys-Arg-Orn binding protein (LAObp or KRObp) secretion signal peptide, an Outer Membrane Porin E (OpreE) secretion signal peptide, an azurin secretion signal peptide, an iron (III) binding protein (Fe(III)bp) secretion signal peptide, or a lipoprotein B (LprB) secretion signal peptide.

In one embodiment, the recombinant peptide, polypeptide, protein, or fragment thereof has a folded intramolecular conformation in its active state. *P. fluorescens* typically produce mammalian proteins more efficiently in the correctly folded conformation. In one embodiment, more than 50% of the expressed, transgenic peptide, polypeptide, protein, or fragment thereof produced can be produced as single peptides, polypeptides, proteins, or fragments thereof in soluble, active form or insoluble, but renaturable form in the cytoplasm or periplasm. In another embodiment about 60%, 70%, 75%, 80%, 85%, 90%, 95% of the expressed protein is obtained in or can be renatured into active form.

Definitions

Throughout this specification, the term "protein" is used to include any amino acid concatamers or polymers. The terms "polypeptide," "peptide" and "protein" are used interchangeably and include amino acid polymers in which one or more amino acid residue is an artificial chemical analogue of a corresponding naturally occurring amino acid, as well as to naturally occurring amino acid polymers.

The term "isolated" refers to nucleic acid, protein, or peptide that is substantially or essentially free from other material components which normally accompany it as found in its native state when in a cell, for example, other cellular components.

The term "purified" or "substantially purified" is used to mean that the protein is separated from other cell components and is separated from other proteins and peptides found in the cell that are not in a native complex with the protein. In particular embodiments, the purified proteins are of a purity approved for therapeutic or veterinary used as defined by standard cGMP guidelines or approved by the FDA.

The term "percent total cell protein" ("tcp") means the amount of protein in the host cell as a percentage of aggregate cellular protein. Alternatively, the term means a measure of the fraction of total cell protein that represents the relative amount of a given protein expressed by the cell.

The term "operably attached" refers to any configuration in which the transcriptional and any translational regulatory elements are covalently attached to the encoding sequence in such disposition(s), relative to the coding sequence, that in and by action of the host cell, the regulatory elements can direct the expression of the coding sequence.

As used herein, the term "mammal" is meant to include or designate any animal in the class Mammalia including human or non-human mammals, such as, but not limited, to porcine, ovine, bovine, rodents, ungulates, pigs, swine, sheep, lambs, goats, cattle, deer, mules, horses, monkeys, apes, dogs, cats, rats, and mice.

As used herein, the term "recombinant mammalian protein" or peptide is meant to include proteins derived from a native mammalian protein sequence or derived or generated from a native mammalian nucleic acid sequence. Such recombinant proteins can be produced from nucleic acid sequence substantially corresponding to native mammalian mRNA or substantially corresponding cDNA, or fragements thereof. The sequence can be adjusted accordingly based on specific host cell codon usage as known in the art.

The phrase "substantially corresponding" in the context of two nucleic acids or polypeptides refers to the residues in the two sequences that have at least 50%, 60%, 70%, 80%, 90% or higher identity when aligned for maximum correspondence over a domain of the protein, as measured using an algorithms known in the art. Optimal alignment of sequences for comparison can be conducted, e.g., by algorithms known in the art (e.g. Smith & Waterman (1981) *Adv. Appl. Math.* 2:482; Needleman & Wunsch (1970) *J. Mol. Biol.* 48:443; Pearson & Lipman (1988) *Proc. Nat'l. Acad. Sci. USA* 85:2444; Altschul et al. (1990) *J. Mol. Biol.* 215:403-410 (BLAST)), by computerized implementations of these algorithms (GAP, BESTFIT, FASTA, and TFASTA in the Wisconsin Genetics Software Package, Genetics Computer Group, 575 Science Dr., Madison, Wis.), or by inspection. Software for performing BLAST analyses is publicly available through the National Center for Biotechnology Information (http://www.ncbi.nlm.nih.gov/).

The term "fragment" means a portion or partial sequence of a nucleotide, protein, or peptide sequence.

As used herein, the term "soluble" means that the protein is not precipitated by centrifugation at between approximately 5,000× and 20,000× gravity when spun for 10-30 minutes in a buffer under physiological conditions. Soluble proteins are not part of an inclusion body or other precipitated mass.

As used herein, the term "insoluble" means that the protein that can be precipitated by centrifugation at between 5,000× and 20,000× gravity when spun for 10-30 minutes in a buffer under physiological conditions. Insoluble proteins can be part of an inclusion body or other precipitated mass.

The term "inclusion body" is meant to include any intracellular body contained within a cell wherein an aggregate of proteins have been sequestered.

As used herein, the term "homologous" means either i) a protein that has an amino acid sequence that at least 70, 75, 80, 85, 90, 95, or 98% similar to the sequence of a given original protein and that retains a desired function of the original protein or ii) a nucleic acid that has a sequence that is at least 70, 75, 80, 5, 90, 95, or 98% similar to the sequence of a given nucleic acid and that retains a desired function of the original nucleic acid sequence. In all of the embodiments of this invention and disclosure, any disclosed protein, peptide or nucleic acid can be substituted with a homologous or substantially homologous protein, peptide or nucleic acid that retains a desired function. In all of the embodiments of this invention and disclosure, when any nucleic acid is disclosed, it should be assumed that the invention also includes all nucleic acids that hybridize to the disclosed nucleic acid.

In one non-limiting embodiment, the non-identical amino acid sequence of the homologous polypeptide can be amino acids that are members of any one of the 15 conservative or semi-conservative groups shown in Table 1.

TABLE 1

Similar Amino Acid Substitution Groups

| Conservative Groups (8) | Semi-Conservative Groups (7) |
| --- | --- |
| Arg, Lys | Arg, Lys, His |
| Asp, Glu | Asn, Asp, Glu, Gln |
| Asn, Gln | |
| Ile, Leu, Val | Ile, Leu, Val, Met, Phe |
| Ala, Gly, | Ala, Gly, Pro, Ser, Thr |
| Ser, Thr | Ser, Thr, Tyr |
| Phe, Tyr | Phe, Trp, Tyr |
| Cys (non-cystine), Ser | Cys (non-cystine), Ser, Thr |

Types of Mammalian Proteins Produced

In general, the recombinant mammalian protein can be any mammalian protein of which an amino acid sequence is known or any putative mammalian or mammalian-derived protein for which an amino acid sequence is deduced. The proteins can be selected from the group consisting of a multi-subunit protein, a blood carrier protein, an enzyme, a full length antibody, an antibody fragment, or a transcriptional factor.

The amino acid sequence of the protein can be altered to adjust for desired qualities, such as to ensure certain types of interactions. The sequence can, for example, be adjusted to reduce immunoreactivity, or to increase absorbtion, reduce excretion, or otherwise enhance bioavailability in an organism such as a mammal. The amino acid sequence of the protein can thus be adjusted to ensure certain post-translational modifications or protein conformations.

In one embodiment, the mammalian protein is a chemokin or cytokine. In another embodiment, the mammalian proteins is one of the following proteins: IL-1, IL-1α, IL-1β, IL-2, IL-3, IL-4, IL-5, IL-6, IL-7, IL-8, IL-9, IL-10, IL-11, IL-12, IL-12elasti, IL-13, IL-15, IL-16, IL-18, IL-18BPa, IL-23, IL-24, VIP, erythropoietin, GM-CSF, G-CSF, M-CSF, platelet derived growth factor (PDGF), MSF, FLT-3 ligand, EGF, fibroblast growth factor (FGF; e.g., aFGF (FGF-1), bFGF (FGF-2), FGF-3, FGF-4, FGF-5, FGF-6, or FGF-7), insulin-like growth factors (e.g., IGF-1, IGF-2); tumor necrosis factors (e.g., TNF, Lymphotoxin), nerve growth factors (e.g., NGF), vascular endothelial growth factor (VEGF); interferons (e.g., IFN-α, IFN-β, IFN-γ); leukemia inhibitory factor (LIF); ciliary neurotrophic factor (CNTF); oncostatin M; stem cell factor (SCF); transforming growth factors (e.g., TGF-α, TGF-β1, TGF-β1, TGF-β1); TNF superfamily (e.g., LIGHT/TNFSF14, STALL-1/TNFSF13B (BLy5, BAFF, THANK), TNFalpha/TNFSF2 and TWEAK/TNFSF12); or chemokines (BCA-1/BLC-1, BRAK/Kec, CXCL16, CXCR3, ENA-78/LIX, Eotaxin-1, Eotaxin-2/MPIF-2, Exodus-2/SLC, Fractalkine/Neurotactin, GROalpha/MGSA, HCC-1, I-TAC, Lymphotactin/ATAC/SCM, MCP-1/MCAF, MCP-3, MCP-4, MDC/STCP-1/ABCD-1, MIP-1α, MIP-1β, MIP-2α/GROβ, MIP-3α/Exodus/LARC, MIP-3α/Exodus-3/ELC, MIP-4/PARC/DC-CK1, PF-4, RANTES, SDF1α, TARC, or TECK).

Alternatively, the protein is not a chemokine or cytokine. In another embodiment, the mammalian protein is not one of the following proteins: IL-1, IL-1α, IL-1β, IL-2, IL-3, IL-4, IL-5, IL-6, IL-7, IL-8, IL-9, IL-10, IL-11, IL-12, IL-12elasti, IL-13, IL-15, IL-16, IL-18, IL-18BPa, IL-23, IL-24, VIP, erythropoietin, GM-CSF, G-CSF, M-CSF, platelet derived growth factor (PDGF), MSF, FLT-3 ligand, EGF, fibroblast growth factor (FGF; e.g., aFGF (FGF-1), bFGF (FGF-2), FGF-3, FGF-4, FGF-5, FGF-6, or FGF-7), insulin-like growth factors (e.g., IGF-1, IGF-2); tumor necrosis factors (e.g., TNF, Lymphotoxin), nerve growth factors (e.g., NGF), vascular endothelial growth factor (VEGF); interferons (e.g., IFN-α, IFN-β, IFN-γ); leukemia inhibitory factor (LIF); ciliary neurotrophic factor (CNTF); oncostatin M; stem cell factor (SCF); transforming growth factors (e.g., TGF-α, TGF-β1, TGF-β1, TGF-β1); TNF superfamily (e.g., LIGHT/TNFSF14, STALL-1/TNFSF13B (BLy5, BAFF, THANK), TNFalpha/TNFSF2 and TWEAK/TNFSF12); or chemokines (BCA-1/BLC-1, BRAK/Kec, CXCL16, CXCR3, ENA-78/LIX, Eotaxin-1, Eotaxin-2/MPIF-2, Exodus-2/SLC, Fractalkine/Neurotactin, GROalpha/MGSA, HCC-1, I-TAC, Lymphotactin/ATAC/SCM, MCP-1/MCAF, MCP-3, MCP-4, MDC/STCP-1/ABCD-1, MIP-1α, MIP-1β, MIP-2α/GROβ, MIP-3α/Exodus/LARC, MIP-3α/Exodus-3/ELC, MIP-4/PARC/DC-CK1, PF-4, RANTES, SDF1α, TARC, or TECK). In one embodiment, the protein is not a porcine protein, particularly not a porcine growth factor.

As yet a further embodiment of the present disclosure, the recombinant mammalian proteins, their fragments or other derivatives, or analogs thereof, can be antibodies. These antibodies can be, for example, polyclonal or monoclonal antibodies. This aspect of the present invention also includes chimeric, single chain, and humanized antibodies, as well as Fab fragments, or the product of an Fab expression library.

Production of Multi-Subunit Proteins

In one embodiment of the present invention, the production of recombinant mammalian multi-subunit proteins by a host cell of the species *Pseudomonas* is provided. In another embodiment, a host cell of the *Pseudomonas* species is provided that has been transformed to express a recombinant mammalian multi-subunit protein. In one embodiment, multisubunit proteins, including recombinant mammalian or human proteins, are expressed in a *Pseudomonas* host cell. In one embodiment, expression of the multi-subunit protein by the host cell is followed by isolation of the multi-subunit protein. In another embodiment, the multi-subunit protein of peptide is purified. The protein can be assembled by the cell before purification or isolation, or further assembly can be undertaken during or after isolation or purification. Optionally, the protein or any portion thereof can be renatured or refolded to produce active proteins.

Any of a variety of vectors and expression systems can be used to express the multi-subunit protein in the host cell. The multi-subunits can be located on a single vector, optionally operably linked to different promoters, optionally in a polycistronic sequence. Each subunit can also be on different vectors. Multiple vectors can be used. Each subunit can be under the control of one or more selection markers. Regulatory elements can be included on the vector, including periplasmic secretion signal sequences, internal ribosome entry sites, activator sequences, promoters, and termination signals.

In one embodiment, multisubunit proteins are expressed in *Pseudomonas* using expression systems with auxotrophic selection markers as disclosed in U.S. application Ser. No. 10/994,138 to Dow Global Technologies filed Nov. 19, 2004, wherein the control of each nucleic acid encoding a subunit is under the control of an auxotrophic selection marker. Multisubunit proteins that can be expressed include homomeric and heteromeric proteins. The multisubunit proteins may include two or more subunits, that may be the same or different. For example, the protein may be a homomeric protein comprising 2, 3, 4, 5, 6, 7, 8, 9, 10, 11, 12 or more subunits. The protein also may be a heteromeric protein including 2, 3, 4, 5, 6, 7, 8, 9, 10, 11, 12, or more subunits.

Exemplary multisubunit mammalian proteins include: receptors including ion channel receptors; signaling proteins such as kinases, GTPases, ATPases; transmembrane proteins; extracellular matrix proteins including chondroitin; collagen; immunomodulators including MHC proteins, full chain antibodies, and antibody fragments; enzymes including RNA polymerases, and DNA polymerases; and membrane proteins.

Production of Blood Proteins

In one embodiment of the present invention, the production of recombinant mammalian blood proteins is provided. In one embodiment, expression of the blood protein by the host cell is followed by isolation of the blood protein. In another embodiment, the blood protein is purified. In another embodiment, following isolation of the blood protein, the blood protein is purified. Optionally, the protein can be renatured or refolded to produce active protein. In general, a recombinant blood protein of this invention is produced by transforming a suitable host cell, such as a *P. fluorescens* host cell, with a nucleic acid construct encoding the blood protein, culturing the transformed host cell under conditions appropriate for expression, and optionally isolating, or isolating and purifying the recombinant blood protein expressed by the cell.

In another embodiment, a host cell of the *Pseudomonas* species is provided that has been transformed to express a recombinant mammalian blood protein with an vector containing appropriate genes and regulatory elements for expression of the blood protein of interest is provided.

The blood proteins that can be expressed include, but are not limited to: carrier proteins, such as albumin, including human albumin (Seq ID No. 1, Table 2) and bovine albumin; transferrin, including human transferrin (Seq ID No. 2, Table 2), bovine transferrin, rat transferrin, recombinant transferrin, recombinant transferrin half-molecules, recombinant transferrin half-molecules having altered properties; haptoglobin; fibrinogen and other coagulation factors; complement components; immunoglobulins; enzyme inhibitors; precursors of substances such as angiotensin and bradykinin; insulin; endothelin; globulin including alpha, beta, and gamma-globulin; and other types of proteins, peptides, and fragments thereof found primarily in the blood of mammals. The amino acid sequences for numerous blood proteins have been reported (see, S. S. Baldwin (1993) *Comp. Biochem Physiol.* 106b: 203-218), including the amino acid sequence for human serum albumin (Lawn, L. M., et al. (1981) *Nucleic Acids Research* 9:22; pp 6103-6114) and human serum transferrin (Yang, F. et al. (1984) *Proc. Natl. Acad. Sci. USA* 81; pp. 2752-2756).

In a specific embodiment, the production of albumin in *P. fluorescens*, is provided, comprising transforming a *P. fluorescens* host cell with an expression vector containing a nucleic acid sequence or sequences and regulatory elements for expression of albumin, culturing the host cell under conditions suitable for expression of the albumin, and recovering the albumin expressed by *P. fluorescens*. According to this embodiment, the albumin expressed is selected from the group consisting of human albumin, bovine albumin, rabbit albumin, chicken albumin, rat albumin, and mouse albumin. In another embodiment, albumin can be fused to a therapeutically active polypeptide, which can be of mammalian or non-mammalian origin.

In a further specific embodiment, the production of a transferrin in *P. fluorescens* is provided, comprising transforming a *P. fluorescens* host cell with an expression vector containing nucleic acid and regulatory elements for expression of the transferrin, culturing the host cell under conditions suitable for expression of the transferring. In another embodiment, following expression of the transferrin, and, in one embodiment, isolating the protein. In a further embodiment, the transferrin can be purified following isolation. The transferrin expressed is selected from the group consisting of human serum transferrin, glycosylated human transferrin, non-glycosylated human transferrin, the N-terminal half-molecule of human transferrin, bovine transferrin, rat transferrin, mouse transferrin, primate transferrin, recombinant transferrin, recombinant transferrin half-molecules, recombinant transferrin half-molecules having altered properties, transferrin polynucleotides, transferrin polypeptides encoded by transferrin polypeptides, transferrin polypeptides, transferrin antibodies, transferrin fragments, and transferrin fused to a therapeutically active polypeptide.

In yet another specific embodiment, the production of a globulin in *P. fluorescens* is provided, comprising transforming a *P. fluorescens* host cell with an expression vector containing nucleic acid and regulatory elements for expression of the globulin, culturing the host cell under conditions suitable for expression of the globulin and optionally isolating the protein. In a further embodiment, following expression, the globulin is isolated and purified from the host cell. The globulin expressed is selected from the group consisting of human globulin, bovine globulin, rabbit globulin, rat globulin, mouse globulin, sheep globulin, monkey globulin, steroid-binding globulins, and globulin fused to a therapeutically active polypeptide.

In a further embodiment, the production of an insulin in *P. fluorescens* is provided, comprising transforming a *P. fluorescens* host cell with an expression vector containing nucleic acid and regulatory elements for expression of the insulin, culturing the host cell under conditions suitable for expression of the insulin and optionally isolatig the protein. In a further embodiment, the insulin can be isolated and purified following production of the insulin by the host cell. The insulin expressed is selected from the group consisting of human insulin, bovine insulin, mouse insulin, rat insulin, porcine insulin, monkey insulin, and insulin fused to a therapeutically active polypeptide. The accession number for human insulin genes is J00265, and for synthetic human insulin gene the accession number is J02547.

Full-length DNA for production of recombinant blood proteins or truncated DNA encoding either the amino-terminal or carboxy-terminal lobe of blood proteins or a portion thereof can be obtained from available sources or can be synthesized according to the known sequences by standard procedures.

The enzymes and co-factors expressed in this embodiment include but are not limited to aldolases, amine oxidases, amino acid oxidases, aspartases, $B_{12}$ dependent enzymes, carboxypeptidases, carboxyesterases, carboxylyases, chemotrypsin, CoA requiring enzymes, cyanohydrin synthetases, cystathione synthases, decarboxylases, dehydrogenases, alcohol dehydrogenases, dehydratases, diaphorases, dioxygenases, enoate reductases, epoxide hydrases, fumerases, galactose oxidases, glucose isomerases, glucose oxidases, glycosyltrasferases, methyltransferases, nitrile hydrases, nucleoside phosphorylases, oxidoreductases, oxynitilases, peptidases, glycosyltrasferases, peroxidases, and enzymes fused to a therapeutically active polypeptide.

In another embodiment, the enzyme can be a mesophilic enzyme polypeptide, for example one that is desirable for human and/or veterinary therapeutic and/or diagnostic use. Examples of such therapeutic mesophilic enzymes include,

TABLE 2

Sequences of blood proteins expressed by the system of the present disclosure.

| | | |
|---|---|---|
| Amino Acid Sequence of human serum albumin | Seq. ID. No: 1 | MKWVTFISLLFLFSSAYSRGVFRRDAHKSEVAHRFKDLGE ENFKALVLIAFAQYLQQCPFEDHVKLVNEVTEFAKTCVAD ESAENCDKSLHTLFGDKLCTVATLRETYGEMADCCAKQE PERNECFLQHKDDNPNLPRLVRPEVDVMCTAFHDNEETFL KKYLYEIRRHPYFYAPELLFFAKRYKAAFTECCQAADKA ACLLPKLDELRDEGKASSAKQRLKCASLQKFGERAFKAW AVARLSQRFPKAEFAEVSKLVTDLTKVHTECCHGDLLECA DDRADLAKYICENQDSISSKCCEKPLLEKSHCIAEVEN DEMPADLPSLAADFVESKDVCKNYAEAKDVFLGMFLYEY ARRHPDYSVVLLLRLAKTYETTLEKCCAAADPHECYAKV FDEFKPLVEEPQNLIKQNCELFKQLGEYKFQNALLVRYTK KVPQVSTPTLVEVSRNLGKVGSKCCKHPEAKRMPCAEDY LSVVLNQLCVLHEKTPVSDRVTKCCTESLVNRRPCFSALE VDETYVPKEFNAETFTFHADICTLSEKERQIKKQTALVELV KHKPKATKEQLKAVMDDFAAFVEKCCKADDKETCFAEE GKKLVAASQAALGL (Lawn, et al. (1981) Nuc. Ac. Rsch. 9(22):6103-6114) |
| Amino Acid Sequence of transferrin | Seq. ID. No: 2 | MRLAVGALLVCAVLGLCLAVPDKTVRWCAVSEHEATKC QSFRDHMKSVIPSDGPSVACVKKASYLDCIRAIAANEADA VTLDAGLVYDAYLAPNNLKPVVAEFYGSKEDPQTFYYAV AVVKKDSGFQMNQLRGKKSCHTGLGRSAGWNIPIGLLYC DLPEPRKPLEKAVANFFSGSCAPCADGTDFPQLCQLCPGC GCSTLNQYFGYSGAFKCLKNGAGDVAFVKHSTIFENLAN KADRDQYELLCLDNTRKPVDEYKDCHLAQVPSHTVVARS MGGKEDLIWELLNQAQEHFGKDKSKEFQLFSSPHGKDLLF KDSAHGFLKVPPRDAKMYLGYEYVTAIRNLREGTCQEA PTDECKPVKWCALSHHERLKCDEWSVNSVGKIECVSAET TEDCAKIMNGEADAMSLDGGFVYIAGKCGLVPVLAENY NKSDNCEDTPEAGYFAVAVVKKSASDLTWDNLKGKKSC HTAVGRTAGWNIPMGLLYNKINHCRFDEFFSEGCAPGSKK DSSLCKLCMGSGLNLCEPNNKEGYYGYTGAFRCLVEKGD VAFVKHQTVPQNTGGKNPDPWAKNLNEKDYELLCLDGT RKPVEEYANCHLARAPNHAVVTRKDKEACVHKILRQQQH LFGSNVTDCSGNFCLFRSETKDLLFRDDTVCLAKLHDRNT YEKYLGEEYVKAVGN LRKCSTSSLLEACTFRRP (Strausberg (2002) PNAS, 99:16899-16903) |
| cDNA Sequence of Human Insulin | Seq. ID. No: 3 | atggccctgtggatgcgcctcctgccctgctggcgctgctggccctctggggacctgacc cagccgcagcctttgtgaaccaacacctgtgcggctcacacctggtggaagctctctaccta gtgtgcggggaacgaggcttcttctacacacccaagacccgccgggaggcagaggacct gcaggtggggcaggtggagctgggcggggccctggtgcaggcagcctgcagcccttg gccctggaggggtccctgcagaagcgtggcattgtggaacaatgctgtaccagcatctgct ccctctaccagctggagaactactgcaactag |

Production of Enzymes

In one embodiment of the present invention, the production of recombinant mammalian enzymes or co-factors by a host cell of the species Pseudomonas fluorescens is provided. In another embodiment, a host cell of the Pseudomonas species is provided that has been transformed to express a recombinant mammalian enzyme or co-factor.

e.g., tissue plasminogen activator; urokinase, reptilase, streptokinase; catalase, superoxide dismutase; DNAse, amino acid hydrolases (e.g., asparaginase, amidohydrolases); carboxypeptidases; proteases, trypsin, pepsin, chymotrypsin, papain, bromelain, collagenase; neuraminidase; lactase, maltase, sucrase, and arabinofuranosidases.

Yet another embodiment provides for the production of recombinant enzyme replacements in P. fluorescens cells by transforming a *P. fluorescens* host cell with an expression vector containing nucleic acids and regulatory elements for xpression of recombinant enzyme replacements, and culturing the cell under conditions suitable for expression of the recombinant enzyme replacements. The recombinant enzyme replacements expressed in the host cell is selected from the group consisting of Algasidase beta, Laronidase, and recombinant enzyme replacements fused to a therapeutically active polypeptide.

Production of Mammalian Antibodies and Antibody Fragments

In one embodiment of the present invention, the production of recombinant mammalian single chain, Fab fragments and/or full chain antibodies or fragments or portions thereof by a host cell of the species *P. fluorescens* is provided. In one embodiment, following expression of the protein, the protein can be isolated and optionally purified. Optionally, the protein can be renatured to produce an active protein. The antibody or antibody fragments are optionally linked to a secretion signal sequence for targeting in the cell during production.

In another embodiment, a host cell of the *Pseudomonas* species is provided that has been transformed to express a recombinant mammalian single chain, Fab fragments and/or full chain antibodies or fragments or portions thereof.

In one embodiment, the *P. fluorescens* cell can produces a single chain antibody or fragments or portions thereof. A single-chain antibody can include the antigen-binding regions of antibodies on a single stably-folded polypeptide chain. Single-chain antibodies are of smaller size than classical immunoglobulins but can retain the antigen-specific binding properties of antibodies. Single chain antibodies can be used for therapeutics, such as "naked" single-chain antibodies, bi-specific antibody binders, radioconjugates or as fusions with effector domains, diagnostics, such as tumor imaging or in vivo or ex vivo cancer marker assays, research tools, such as protein purification and detection, including identification and characterization of novel therapeutic targets, antibody microarrays, display technologies and/or vehicles for gene or drug delivery.

In another embodiment, the *P. fluorescens* cell produces Fab fragments or portions thereof. Fab fragments can be a piece of a particular antibody. The Fab fragment can contain the antigen binding site. The Fab fragment can contains 2 chains: a light chain and a heavy chain fragment. These fragments can be linked via alinker or a disulfide bond.

In other embodiments of the present invention, full chain antibodies can be expressed in *P. fluorescens*, and other *Pseudomonas* species. An intact antibody containing the Fc region can be more resistant against degradation and clearance in vivo, thereby having longer biological half life in circulation. Such antibodies can be used as a therapeutic agent for diseases requiring sustained therapies.

In one embodiment, a process for producing a functional antibody or fragment thereof in *Pseudomonas* species is provided by providing an expression vector that contains separate cistronic or polycistronic sequences. The separate cistron expression vector can contain a first promoter-cistron pair for expression of an immunoglobulin light chain and a second promoter-cistron pair for expression of an immunoglobulin heavy chain, such that expression of the light chain and heavy chain are independently regulated by separate promoters. Each cistron within the expression cassette polynucleotide can include a translation initiation region (TIR) operably linked to the nucleic acid sequence coding for the light chain or heavy chain of the full length antibody. In one embodiment, the TIR sequences can be manipulated to provide different translational strength combinations for light and heavy chains. In an alternative embodiment, a heavy chain coding sequence can be located on the same plasmid as a light chain coding sequence. In an alternative embodiment, the heavy and light chain sequences are found in a polycistronic sequence within a single plasmid, or coded into the genome of the host.

In another embodiment, a process is provided for producing a functional antibody or fragment thereof in a host cell transformed with two separate translational units respectively encoding the light and heavy chains of the antibody. In one embodiment the process includes: a) culturing the host cell under suitable conditions so that the light chain and heavy chain are expressed in a sequential fashion, thereby temporally separating the production of the light and heavy chains; and b) allowing the assembly of the light and heavy chains to form the functional antibody or fragment thereof.

In further embodiment, the *Pseudomonas* expression system can express human therapeutic single chain, Fab fragments or full chain antibodies or portions thereof, including, but not limited to Fab, Fab', F(ab')$_2$, F(ab')$_2$-leucine zipper, Fv, dsFv, anti-CD18 antibody, chimeric antibodies, human antibodies, humanized antibodies, or those described in the Table 3 below.

TABLE 3

Antibodies and Antibody Fragments.

| Antibody | Target Antigen | Product Type | Isotype | Indication |
|---|---|---|---|---|
| 5G1.1 | Complement (C5) | Humanised | IgG | Rheumatoid Arthritis |
| 5G1.1 | Complement (C5) | Humanised | IgG | SLE |
| 5G1.1 | Complement (C5) | Humanised | IgG | Nephritis |
| 5G1.1-SC | Complement (C5) | Humanised | ScFv | Cardiopulmanory Bypass |
| 5G1.1-SC | Complement (C5) | Humanised | ScFv | Myocardial Infarction |
| 5G1.1-SC | Complement (C5) | Humanised | ScFv | Angioplasty |
| ABX-CBL | CBL | Human | | GvHD |
| ABX-CBL | CD147 | Murine | IgG | Allograft rejection |
| ABX-IL8 | IL-8 | Human | IgG2 | Psoriasis |
| AD-159 | gp120 | Humanised | | HIV |
| AD-439 | gp120 | Humanised | | HIV |
| Antegren | VLA-4 | Humanised | IgG | Multiple Sclerosis |
| Anti-CD11a | CD11a | Humanised | IgG1 | Psoriasis |
| Anti-CD18 | CD18 | Humanised | Fab'2 | Myocardial infarction |
| Anti-LFA1 | CD18 | Murine | Fab'2 | Allograft rejection |
| Anti-VEGF | VEGF | Humanised | IgG1 | Cancer (general |
| Antova | CD40L | Humanised | IgG | Allograft rejection |

TABLE 3-continued

Antibodies and Antibody Fragments.

| Antibody | Target Antigen | Product Type | Isotype | Indication |
|---|---|---|---|---|
| Antova | CD40L | Humanised | IgG | SLE |
| BEC2 | anti-Id | Murine | IgG | Lung |
| BIRR-1 | ICAM-1 | Murine | IgG2a | Stroke |
| BTI-322 | CD2 | Rat | IgG | GvHD |
| C225 | EGFR | Chimeric | IgG | Head + Neck |
| CAT-152 | TGF-beta 2 | Human | | Glaucoma Surgery |
| CDP571 | TNF-alpha | Humanised | IgG4 | Crohn's |
| CDP571 | TNF-alpha | Humanised | IgG4 | Rheumatoid Arthritis |
| CDP850 | E-selectin | Humanised | | Psoriasis |
| Corsevin M | Fact VII | Chimeric | | Anticoagulant |
| D2E7 | TNF-alpha | Human | | Rheumatoid Arthritis |
| Herceptin | Her2/neu | Humanised | IgG1 | Metastatic Breast |
| HNK20 | F gp | Murine | IgA | RSV |
| Hu23F2G | CD11/18 | Humanised | | Multiple Sclerosis |
| Hu23F2G | CD11/18 | Humanised | IgG | Stroke |
| IC14 | CD14 | — | | Toxic shock |
| ICM3 | ICAM-3 | Humanised | | Psoriasis |
| IDEC-114 | CD80 | Primatised | | Psoriasis |
| IDEC-131 | CD40L | Humanised | | SLE |
| IDEC-131 | CD40L | Humanised | | Multiple Sclerosis |
| IDEC-151 | CD4 | Primatised | IgG1 | Rheumatoid Arthritis |
| IDEC-152 | CD23 | Primatised | | Asthma/Allergy |
| Infliximab | TNF-alpha | Chimeric | IgG1 | Rheumatoid Arthritis |
| Infliximab | TNF-alpha | Chimeric | IgG1 | Crohn's |
| LDP-01 | beta2-integrin | Humanised | IgG | Stroke |
| LDP-01 | beta2-integrin | Humanised | IgG | Allograft rejection |
| LDP-02 | alpha4beta7 | Humanised | | Ulcerative Colitis |
| LDP-03/Campath1H | CD52 | Humanised | IgG1 | CLL |
| Lym-1 | HLA DR | Chimeric | | NHL |
| LympoCide | CD22 | Humanised | | NHL |
| MAK-195F | TNF alpha | Murine | Fab'2 | Toxic shock |
| MDX-33 | CD64 (FcR) | Human | | Autoimmune haematogical disorders |
| MDX-CD4 | CD4 | Human | IgG | Rheumatoid Arthritis |
| MEDI-500 | TCR alpha beta | Murine | IgM | GvHD |
| MEDI-507 | CD2 | Humanised | | Psoriasis |
| MEDI-507 | CD2 | Humanised | | GvHD |
| OKT4A | CD4 | Humanised | IgG | Allograft rejection |
| OrthoClone OKT4A | CD4 | Humanised | IgG | Autoimmune disease |
| Orthoclone/anti-CD3 OKT3 | CD3 | Murine | mIgG2a | Allograft rejection |
| Ostavir | Hep B | Human | | Hep B |
| OvaRex | CA 125 | Murine | | Ovarian |
| Panorex 17-1A | EpCAM | Murine | IgG2a | Colorectal |
| PRO542 | gp120 | Humanised | | HIV |
| Protovir | CMV | Humanised | IgG1 | CMV |
| RepPro/Abciximab | gpIIbIIIa | Chimeric | Fab | Complications of coronary angioplasty |
| rhuMab-E25 | IgE | Humanised | IgG1 | Asthma/Allergy |
| Rituxan | CD20 | Chimeric | IgG1 | NHL |
| SB-240563 | IL5 | Humanised | | Asthma/Allergy |
| SB-240683 | IL-4 | Humanised | | Asthma/Allergy |
| SCH55700 | IL-5 | Humanised | | Asthma/Allergy |
| Simulect | CD25 | Chimeric | IgG1 | Allograft rejection |
| SMART a-CD3 | CD3 | Humanised | | Autoimmune disease |
| SMART a-CD3 | CD3 | Humanised | | Allograft rejection |
| SMART a-CD3 | CD3 | Humanised | IgG | Psoriasis |
| SMART M195 | CD33 | Humanised | IgG | AML |
| SMART 1D10 | HLA | — | | NHL |
| Synagis | F gp | Humanised | IgG1 | RSV (Paediatric) |
| Vitaxin | VNRintegrin | Humanised | | Sarcoma |
| Zenapax | CD25 | Humanised | IgG1 | Allograft rejection |

Production of Transcriptional Factors

In one embodiment of the present invention, the production of recombinant mammalian transcription factors by a host cell of the species *Pseudomonas fluorescens* is provided. In one embodiment, following expression of the protein, the protein can be isolated. In another embodiment, the protein can be purified. Optionally, the protein can be renatured to produce an active protein. In another embodiment, a host cell of the *Pseudomonas* species is provided that has been transformed to express a recombinant mammalian transcription factor.

Transcription factors suitable for insertion into the expression systems of the present invention include those of the helix turn helix family and members of the Pac family, as well as other transcription factor families known in the art. Members of these families suitable for use with the present invention include mammalian and mammalian homologs and analogs of: transcriptional regulators; transcription factors of the of the ASNC family such as ASNC_trans_reg, putative transcriptional regulators; bacterial regulatory proteins of the luxR family; bacterial regulatory helix-turn-helix transcription factors; bacterial regulatory proteins of the arsR family; transcription factors of the helix-turn-helix domain, especially the rpiR family; bacterial regulatory protein transcription factors, bacterial regulatory helix-turn-helix transcription factors; DNA binding domain transcription factors; MarR family of transcription factors; the ROK family of transcription factors; the MerR family of regulatory proteins; arginine repressor transcription factors; firmicute transcriptional factors; ferric uptake regulatory transcription factors; sigma transcription factors; response regulatory receiver transcription factors; tryptophan RNA-binding attenuator protein transcription factors; putative sugar-binding domain transcription factors; PRD domain transcription factors; nitrogen regulatory protein transcription factors; negative regulators of genetic competence, such as MecA; negative transcriptional regulator transcription factors; bacterial transcriptional regulator transcription factors; glycerol-3-phosphate responsive transcription factors; iron dependent repressor transcription factors; and numerous species specific transcriptional regulator transcription factors.

Transcriptional factors expressed by *Pseudomonas* species can be utilized for diagnostic, therapeutic, and investigational applications.

Vector Preparation

Polynucleotides

The recombinant mammalian proteins and peptides can be expressed from polynucleotides in which the target polypeptide coding sequence is operably attached to transcription and translation regulatory elements forming a functional gene from which the host cell can express the protein. The coding sequence can be a native coding sequence for the target polypeptide, if available, but can also be a coding sequence that has been selected, improved, or optimized for use in the selected expression host cell: for example, by synthesizing the gene to reflect the codon use bias of a *Pseudomonas* species such as *P. fluorescens*. The gene(s) that result will have been constructed within or will be inserted into one or more vector, which will then be transformed into the expression host cell. Nucleic acid or a polynucleotide said to be provided in an "expressible form" means nucleic acid or a polynucleotide that contains at least one gene that can be expressed by the selected bacterial expression host cell.

Regulatory Elements

The regulatory elements used herein can be operably attached to the target recombinant mammalian protein encoding gene. The coding sequence of the protein-encoding gene used herein can contain, in addition to the mature polypeptide coding sequence and transcription-regulatory elements, further encoding elements, e.g., one or more of coding sequences for peptide tags, pre-peptides, pro-peptides, pre-pro-peptides, or other commonly utilized encoding elements known in the art, excluding secretion signal peptides functional in the selected expression host cell.

The term "operably attached," as used herein, refers to any configuration in which the transcriptional and any translational regulatory elements are covalently attached to the coding sequence in such disposition(s), relative to the coding sequence, that the regulatory elements can direct the expression of the coding sequence. In one embodiment, the regulatory elements will be part of a whole gene before undergoing transformation into a host cell; however, in other embodiments the regulatory elements are part of another gene, which can be part of the host genome or can be part of a genome of another organism, or can be derived therefrom.

Promoters and Accessory Elements

The promoters used in accordance with the present invention may be constitutive promoters or regulated promoters. Common examples of useful regulated promoters include those of the family derived from the lac promoter (i.e. the lacZ promoter), especially the tac and trc promoters described in U.S. Pat. No. 4,551,433 to DeBoer, as well as Ptac16, Ptac17, PtacII, PlacUV5, and the T7lac promoter.

Common examples of non-lac-type promoters useful in expression systems according to the present invention include, e.g., those listed in Table 4.

TABLE 4

| Examples of non-lac Promoters | |
|---|---|
| Promoter | Inducer |
| $\lambda P_R$ | High temperature |
| $\lambda P_L$ | High temperature |
| Pm | Alkyl- or halo-benzoates |
| Pu | Alkyl- or halo-toluenes |
| Psal | Salicylates |

See, e.g.: J. Sanchez-Romero & V. De Lorenzo (1999) *Manual of Industrial Microbiology and Biotechnology* (A. Demain & J. Davies, eds.) pp. 460-74 (ASM Press, Washington, D.C.); H. Schweizer (2001) *Current Opinion in Biotechnology* 12:439-445; and R. Slater & R. Williams (2000) *Molecular Biology and Biotechnology* (J. Walker & R. Rapley, eds.) pp. 125-54. A promoter having the nucleotide sequence of a promoter native to the selected bacterial host cell may also be used to control expression of the transgene encoding the target polypeptide, e.g, a *Pseudomonas* anthranilate or benzoate operon promoter (Pant, Pben). Tandem promoters may also be used in which more than one promoter is covalently attached to another, whether the same or different in sequence, e.g., a Pant-Pben tandem promoter (interpromoter hybrid) or a Plac-Plac tandem promoter.

Regulated promoters utilize promoter regulatory proteins in order to control transcription of the gene of which the promoter is a part. Where a regulated promoter is used herein, a corresponding promoter regulatory protein will also be part of an expression system according to the present invention. Examples of promoter regulatory proteins include: activator proteins, e.g., *E. coli* catabolite activator protein, MalT protein; AraC family transcriptional activators; repressor proteins, e.g., *E. coli* LacI proteins; and dual-fuction regulatory proteins, e.g., *E. coli* NagC protein. Many regulated-promoter/promoter-regulatory-protein pairs are known in the art.

Promoter regulatory proteins interact with an effector compound, i.e. a compound that reversibly or irreversibly associates with the regulatory protein so as to enable the protein to either release or bind to at least one DNA transcription regulatory region of the gene that is under the control of the promoter, thereby permitting or blocking the action of a transcriptase enzyme in initiating transcription of the gene. Effector compounds are classified as either inducers or co-repressors, and these compounds include native effector compounds and gratuitous inducer compounds. Many regulated-promoter/promoter-regulatory-protein/effector-compound trios are known in the art. Although an effector compound can be used throughout the cell culture or fermentation, in one embodiment in which a regulated promoter is used, after growth of a desired quantity or density of host cell biomass, an appropriate effector compound is added to the culture in order directly or indirectly result in expression of the desired target gene(s).

By way of example, where a lac family promoter is utilized, a lacI gene can also be present in the system. The lacI gene, which is (normally) a constitutively expressed gene, encodes the Lac repressor protein (LacI protein) which binds to the lac operator of these promoters. Thus, where a lac family promoter is utilized, the lacI gene can also be included and expressed in the expression system. In the case of the lac promoter family members, e.g., the tac promoter, the effector compound is an inducer, such as a gratuitous inducer like IPTG (isopropyl-β-D-1-thiogalactopyranoside, also called "isopropylthiogalactoside").

Other Elements

Other regulatory elements can be included in an expression construct. Such elements include, but are not limited to, for example, transcriptional enhancer sequences, translational enhancer sequences, other promoters, activators, translational start and stop signals, transcription terminators, cistronic regulators, polycistronic regulators, tag sequences, such as nucleotide sequence "tags" and "tag" peptide coding sequences, which facilitates identification, separation, purification, or isolation of an expressed polypeptide.

At a minimum, a protein-encoding gene according to the present invention can include, in addition to the mammalian protein coding sequence, the following regulatory elements operably linked thereto: a promoter, a ribosome binding site (RBS), a transcription terminator, translational start and stop signals. Useful RBSs can be obtained from any of the species useful as host cells in expression systems, such as from the selected host cell. Many specific and a variety of consensus RBSs are known, e.g., those described in and referenced by D. Frishman et al. (1999) *Gene* 234 (2):257-65; and B. E. Suzek et al. (2001) *Bioinformatics* 17 (12): 1123-30. In addition, either native or synthetic RBSs may be used, e.g., those described in: EP 0207459 (synthetic RBSs); O. Ikehata et al. (1989) *Eur. J. Biochem.* 181 (3):563-70 (native RBS sequence of AAGGAAG). Further examples of methods, vectors, and translation and transcription elements, and other elements useful in the present invention are described in, e.g.: U.S. Pat. Nos. 5,055,294 and 5,128,130 to Gilroy et al.; U.S. Pat. No. 5,281,532 to Rammler et al.; U.S. Pat. Nos. 4,695,455 and 4,861,595 to Barnes et al.; U.S. Pat. No. 4,755,465 to Gray et al.; and U.S. Pat. No. 5,169,760 to Wilcox.

Vectors

Transcription of the DNA encoding the enzymes of the present invention by *Pseudomonas* is increased by inserting an enhancer sequence into the vector or plasmid. Typical enhancers are cis-acting elements of DNA, usually about from 10 to 300 bp in size that act on the promoter to increase its transcription. Examples include various *Pseudomonas* enhancers, as described elsewhere herein.

Generally, the recombinant expression vectors will include origins of replication and selectable markers permitting transformation of the *Pseudomonas* host cell, e.g., the antibiotic-free resistance genes of *P. fluorescens*, and a promoter derived from a highly-expressed gene to direct transcription of a downstream structural sequence. Such promoters can be derived from operons encoding the enzymes such as 3-phosphoglycerate kinase (PGK), acid phosphatase, or heat shock proteins, among others. The heterologous structural sequence is assembled in appropriate phase with translation initiation and termination sequences, and, in one embodiment, a leader sequence capable of directing secretion of the translated enzyme. Optionally, the heterologous sequence can encode a fusion enzyme including an N-terminal identification peptide imparting desired characteristics, e.g., stabilization or simplified purification of expressed recombinant product.

Useful expression vectors for use with *P. fluorescens* in expressing enzymes are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host.

Vectors are known in the art as useful for expressing recombinant proteins in host cells, and any of these may be used for expressing the genes according to the present invention. Such vectors include, e.g., plasmids, cosmids, and phage expression vectors. Examples of useful plasmid vectors include, but are not limited to, the expression plasmids pBBR1MCS, pDSK519, pKT240, pML122, pPS10, RK2, RK6, pRO1600, and RSF1010. Other examples of such useful vectors include those described by, e.g.: N. Hayase (1994) *Appl. Envir. Microbiol.* 60 (9):3336-42; A. A. Lushnikov et al. (1985) *Basic Life Sci.* 30:657-62; S. Graupner & W. Wackemagel (2000) *Biomolec. Eng.* 17 (1):11-16.; H. P. Schweizer (2001) *Curr. Opin. Biotech.* 12 (5):439-45; M. Bagdasarian & K. N. Timmis (1982) *Curr. Topics Microbiol. Immunol.* 96:47-67; T. Ishii et al. (1994) *FEMS Microbiol. Lett.* 116 (3):307-13; I. N. Olekhnovich & Y. K. Fomichev (1994) *Gene* 140 (1):63-65; M. Tsuda & T. Nakazawa (1993) *Gene* 136 (1-2):257-62; C. Nieto et al. (1990) *Gene* 87 (1):145-49; J. D. Jones & N. Gutterson (1987) *Gene* 61 (3):299-306; M. Bagdasarian et al. (1981) *Gene* 16 (1-3): 237-47; H. P. Schweizer et al. (2001) *Genet. Eng.* (NY) 23:69-81; P. Mukhopadhyay et al. (1990) *J. Bact.* 172 (1):477-80; D. O. Wood et al. (1981) *J. Bact.* 145 (3):1448-51; and R. Holtwick et al. (2001) *Microbiology* 147 (Pt 2):337-44.

Further examples of expression vectors that can be useful in *Pseudomonas* host cells include those listed in Table 5 as derived from the indicated replicons.

TABLE 5

Some Examples of Useful Expression Vectors

| Replicon | Vector(s) |
|---|---|
| pPS10 | pCN39, pCN51 |
| RSF1010 | pKT261-3 |
|  | pMMB66EH |
|  | pEB8 |
|  | pPLGN1 |
|  | pMYC1050 |
| RK2/RP1 | pRK415 |
|  | pJB653 |
| pRO1600 | pUCP |
|  | pBSP |

The expression plasmid, RSF1010, is described, e.g., by F. Heffron et al. (1975) *Proc. Nat'l Acad. Sci. USA* 72 (9):3623-27, and by K. Nagahari & K. Sakaguchi (1978) *J. Bact.* 133 (3):1527-29. Plasmid RSF1010 and derivatives thereof are particularly useful vectors in the present invention. Exemplary, useful derivatives of RSF1010, which are known in the art, include, e.g., pKT212, pKT214, pKT231 and related plasmids, and pMYC1050 and related plasmids (see, e.g., U.S. Pat. Nos. 5,527,883 and 5,840,554 to Thompson et al.), such as, e.g., pMYC1803. Plasmid pMYC1803 is derived from the RSF1010-based plasmid pTJS260 (see U.S. Pat. No. 5,169,760 to Wilcox), which carries a regulated tetracycline resistance marker and the replication and mobilization loci from the RSF1010 plasmid. Other exemplary useful vectors include those described in U.S. Pat. No. 4,680,264 to Puhler et al.

In a one embodiment, an expression plasmid is used as the expression vector. In another embodiment, RSF1010 or a derivative thereof is used as the expression vector. In still another embodiment, pMYC1050 or a derivative thereof, or pMYC1803 or a derivative thereof, is used as the expression vector.

The plasmid can be maintained in the host cell by use of a selection marker gene, also present in the plasmid. This may be an antibiotic resistance gene(s), in which case the corresponding antibiotic(s) will be added to the fermentation medium, or any other type of selection marker gene known as useful in the art, e.g., a prototrophy-restoring gene in which case the plasmid will be used in a host cell that is auxotrophic for the corresponding trait, e.g., a biocatalytic trait such as an amino acid biosynthesis or a nucleotide biosynthesis trait or a carbon source utilization trait.

Extensive sequence information required for molecular genetics and genetic engineering techniques is widely publicly available. Access to complete nucleotide sequences of mammalian, as well as human genes, cDNA sequences, amino acid sequences and genomes can be obtained from the GenBank database Additional information can also be obtained from GeneCards, an electronic encyclopedia integrating information about genes and their products and biomedical applications from the Weizmann Institute of Science Genome and Bioinformatics, nucleotide sequence information can also be obtained from the EMBL Nucleotide Sequence Database or the DNA Databank or Japan (DDBJ,), additional sites for information on amino acid sequences include Georgetown's protein information resource website and the Swiss-Prot database.

Transformation

Transformation of the *Pseudomonas* host cells with the vector(s) may be performed using any transformation methodology known in the art, and the bacterial host cells may be transformed as intact cells or as protoplasts (i.e. including cytoplasts). Exemplary transformation methodologies include poration methodologies, e.g., electroporation, protoplast fusion, bacterial conjugation, and divalent cation treatment, e.g., calcium chloride treatment or $CaCl/Mg^{2+}$ treatment, or other well known methods in the art. See, e.g., Morrison (1977) *J. Bact.* 132:349-351; Clark-Curtiss & Curtiss (1983) *Methods in Enzymology* 101:347-362, Sambrook et al. (1989) Molecular Cloning, A Laboratory Manual (2nd ed.); Kriegler (1990) *Gene Transfer and Expression: A Laboratory Manual*; and Ausubel et al., eds. (1994) *Current Protocols in Molecular Biology*.

Pseudomonas Organisms

While the primary invention herein is the use of *Pseudomonas fluorescens*, other *Pseudomonas* and closely related bacterial organisms can be useful. *Pseudomonas* and closely related bacteria are generally part of the group defined as "Gram(−) Proteobacteria Subgroup 1" or "Gram-Negative Aerobic Rods and Cocci" (Buchanan and Gibbons (eds.) (1974) *Bergey's Manual of Determinative Bacteriology*, pp. 217-289).

TABLE 6

"Gram-Negative Aerobic Rods and *Cocci*" (Bergey (1974))

| | |
|---|---|
| Family I. Pseudomonadaceae | *Gluconobacter* |
|  | *Pseudomonas* |
|  | *Xanthomonas* |
|  | *Zoogloea* |
| Family II. Azotobacteraceae | *Azomonas* |
|  | *Azotobacter* |
|  | *Beijerinckia* |
|  | *Derxia* |
| Family III. Rhizobiaceae | *Agrobacterium* |
|  | *Rhizobium* |
| Family IV. Methylomonadaceae | *Methylococcus* |
|  | *Methylomonas* |
| Family V. Halobacteriaceae | *Halobacterium* |
|  | *Halococcus* |
| Other Genera | *Acetobacter* |
|  | *Alcaligenes* |
|  | *Bordetella* |
|  | *Brucella* |
|  | *Francisella* |
|  | *Thermus* |

"Gram-negative Proteobacteria Subgroup 1" also includes Proteobacteria that would be classified in this heading according to the criteria used in the classification. The heading also includes groups that were previously classified in this section but are no longer, such as the genera *Acidovorax, Brevundimonas, Burkholderia, Hydrogenophaga, Oceanimonas, Ralstonia*, and *Stenotrophomonas*, the genus *Sphingomonas* (and the genus *Blastomonas*, derived therefrom), which was created by regrouping organisms belonging to (and previously called species of) the genus *Xanthomonas*, the genus *Acidomonas*, which was created by regrouping organisms belonging to the genus *Acetobacter* as defined in Bergey (1974). In addition hosts can include cells from the genus *Pseudomonas, Pseudomonas enalia* (ATCC 14393), *Pseudomonas nigrifaciens* (ATCC 19375), and *Pseudomonas putrefaciens* (ATCC 8071), which have been reclassified respectively as *Alteromonas haloplanktis, Alteromonas nigrifaciens*, and *Alteromonas putrefaciens*. Similarly, e.g., *Pseudomonas acidovorans* (ATCC 15668) and *Pseudomonas testosteroni* (ATCC 11996) have since been reclassified as *Comamonas acidovorans* and *Comamonas testosteroni*, respectively; and *Pseudomonas nigrifaciens* (ATCC 19375) and *Pseudomonas piscicida* (ATCC 15057) have been reclassified respectively as *Pseudoalteromonas nigrifaciens* and *Pseudoalteromonas piscicida*.

"Gram-negative Proteobacteria Subgroup 1" also includes Proteobacteria classified as belonging to any of the families: Pseudomonadaceae, Azotobacteraceae (now often called by the synonym, the "*Azotobacter* group" of Pseudomonadaceae), Rhizobiaceae, and Methylomonadaceae (now often called by the synonym, "Methylococcaceae"). Consequently, in addition to those genera otherwise described herein, further Proteobacterial genera falling within "Gram-negative Proteobacteria Subgroup 1" include: 1) *Azotobacter* group bacteria of the genus *Azorhizophilus*; 2) Pseudomonadaceae family bacteria of the genera *Cellvibrio, Oligella*, and *Teredinibacter*; 3) Rhizobiaceae family bacteria of the genera *Chelatobacter, Ensifer, Liberibacter* (also called "*Candidatus Liberibacter*"), and *Sinorhizobium*; and 4) Methylococcaceae family bacteria of the genera *Methylobacter, Methylocaldum, Methylomicrobium, Methylosarcina*, and *Methylosphaera*.

In another embodiment, the host cell is selected from "Gram-negative Proteobacteria Subgroup 2." "Gram-negative Proteobacteria Subgroup 2" is defined as the group of Proteobacteria of the following genera (with the total numbers of catalog-listed, publicly-available, deposited strains thereof indicated in parenthesis, all deposited at ATCC, except as otherwise indicated): *Acidomonas* (2); *Acetobacter* (93); *Gluconobacter* (37); *Brevundimonas* (23); *Beijerinckia* (13); *Derxia* (2); *Brucella* (4); *Agrobacterium* (79); *Chelatobacter* (2); *Ensifer* (3); *Rhizobium* (144); *Sinorhizobium* (24); *Blastomonas* (1); *Sphingomonas* (27); *Alcaligenes* (88); *Bordetella* (43); *Burkholderia* (73); *Ralstonia* (33); *Acidovorax* (20); *Hydrogenophaga* (9); *Zoogloea* (9); *Methylobacter* (2); *Methylocaldum* (1 at NCIMB); *Methylococcus* (2); *Methylomicrobium* (2); *Methylomonas* (9); *Methylosarcina* (1); *Methylosphaera*; *Azomonas* (9); *Azorhizophilus* (5); *Azotobacter* (64); *Cellvibrio* (3); *Oligella* (5); *Pseudomonas* (1139); *Francisella* (4); *Xanthomonas* (229); *Stenotrophomonas* (50); and *Oceanimonas* (4).

Exemplary host cell species of "Gram-negative Proteobacteria Subgroup 2" include, but are not limited to the following bacteria (with the ATCC or other deposit numbers of exemplary strain(s) thereof shown in parenthesis): *Acidomonas methanolica* (ATCC 43581); *Acetobacter aceti* (ATCC 15973); *Gluconobacter oxydans* (ATCC 19357); *Brevundimonas diminuta* (ATCC 11568); *Beijerinckia indica* (ATCC 9039 and ATCC 19361); *Derxia gummosa* (ATCC 15994); *Brucella melitensis* (ATCC 23456), *Brucella abortus* (ATCC 23448); *Agrobacterium tumefaciens* (ATCC 23308), *Agrobacterium radiobacter* (ATCC 19358), *Agrobacterium rhizogenes* (ATCC 11325); *Chelatobacter heintzii* (ATCC 29600); *Ensifer adhaerens* (ATCC 33212); *Rhizobium leguminosarum* (ATCC 10004); *Sinorhizobium fredii* (ATCC 35423); *Blastomonas natatoria* (ATCC 35951); *Sphingomonas paucimobilis* (ATCC 29837); *Alcaligenes faecalis* (ATCC 8750); *Bordetella pertussis* (ATCC 9797); *Burkholderia cepacia* (ATCC 25416); *Ralstonia pickettii* (ATCC 27511); *Acidovorax facilis* (ATCC 11228); *Hydrogenophaga flava* (ATCC 33667); *Zoogloea ramigera* (ATCC 19544); *Methylobacter luteus* (ATCC 49878); *Methylocaldum gracile* (NCIMB 11912); *Methylococcus capsulatus* (ATCC 19069); *Methylomicrobium agile* (ATCC 35068); *Methylomonas methanica* (ATCC 35067); *Methylosarcina fibrata* (ATCC 700909); *Methylosphaera hansonii* (ACAM 549); *Azomonas agilis* (ATCC 7494); *Azorhizophilus paspali* (ATCC 23833); *Azotobacter chroococcum* (ATCC 9043); *Cellvibrio mixtus* (UQM 2601); *Oligella urethralis* (ATCC 17960); *Pseudomonas aeruginosa* (ATCC 10145), *Pseudomonas fluorescens* (ATCC 35858); *Francisella tularensis* (ATCC 6223); *Stenotrophomonas maltophilia* (ATCC 13637); *Xanthomonas campestris* (ATCC 33913); and *Oceanimonas doudoroffii* (ATCC 27123).

In another embodiment, the host cell is selected from "Gram-negative Proteobacteria Subgroup 3." "Gram-negative Proteobacteria Subgroup 3" is defined as the group of Proteobacteria of the following genera: *Brevundimonas; Agrobacterium; Rhizobium; Sinorhizobium; Blastomonas; Sphingomonas; Alcaligenes; Burkholderia; Ralstonia; Acidovorax; Hydrogenophaga; Methylobacter; Methylocaldum; Methylococcus; Methylomicrobium; Methylomonas; Methylosarcina; Methylosphaera; Azomonas; Azorhizophilus; Azotobacter; Cellvibrio; Oligella; Pseudomonas; Teredinibacter; Francisella; Stenotrophomonas; Xanthomonas*; and *Oceanimonas*.

In another embodiment, the host cell is selected from "Gram-negative Proteobacteria Subgroup 4." "Gram-negative Proteobacteria Subgroup 4" is defined as the group of Proteobacteria of the following genera: *Brevundimonas; Blastomonas; Sphingomonas; Burkholderia; Ralstonia; Acidovorax; Hydrogenophaga; Methylobacter; Methylocaldum; Methylococcus; Methylomicrobium; Methylomonas; Methylosarcina; Methylosphaera; Azomonas; Azorhizophilus; Azotobacter; Cellvibrio; Oligella; Pseudomonas; Teredinibacter; Francisella; Stenotrophomonas; Xanthomonas*; and *Oceanimonas*.

In an embodiment, the host cell is selected from "Gram-negative Proteobacteria Subgroup 5." "Gram-negative Proteobacteria Subgroup 5" is defined as the group of Proteobacteria of the following genera: *Methylobacter; Methylocaldum; Methylococcus; Methylomicrobium; Methylomonas; Methylosarcina; Methylosphaera; Azomonas; Azorhizophilus; Azotobacter; Cellvibrio; Oligella; Pseudomonas; Teredinibacter; Francisella; Stenotrophomonas; Xanthomonas*; and *Oceanimonas*.

The host cell can be selected from "Gram-negative Proteobacteria Subgroup 6." "Gram-negative Proteobacteria Subgroup 6" is defined as the group of Proteobacteria of the following genera: *Brevundimonas; Blastomonas; Sphingomonas; Burkholderia; Ralstonia; Acidovorax; Hydrogenophaga; Azomonas; Azorhizophilus; Azotobacter; Cellvibrio; Oligella; Pseudomonas; Teredinibacter; Stenotrophomonas; Xanthomonas*; and *Oceanimonas*.

The host cell can be selected from "Gram-negative Proteobacteria Subgroup 7." "Gram-negative Proteobacteria Subgroup 7" is defined as the group of Proteobacteria of the following genera: *Azomonas; Azorhizophilus; Azotobacter; Cellvibrio; Oligella; Pseudomonas; Teredinibacter; Stenotrophomonas; Xanthomonas*; and *Oceanimonas*.

The host cell can be selected from "Gram-negative Proteobacteria Subgroup 8." "Gram-negative Proteobacteria Subgroup 8" is defined as the group of Proteobacteria of the following genera: *Brevundimonas; Blastomonas; Sphingomonas; Burkholderia; Ralstonia; Acidovorax; Hydrogenophaga; Pseudomonas; Stenotrophomonas; Xanthomonas*; and *Oceanimonas*.

The host cell can be selected from "Gram-negative Proteobacteria Subgroup 9." "Gram-negative Proteobacteria Subgroup 9" is defined as the group of Proteobacteria of the following genera: *Brevundimonas; Burkholderia; Ralstonia; Acidovorax; Hydrogenophaga; Pseudomonas; Stenotrophomonas*; and *Oceanimonas*.

The host cell can be selected from "Gram-negative Proteobacteria Subgroup 10." "Gram-negative Proteobacteria Subgroup 10" is defined as the group of Proteobacteria of the following genera: *Burkholderia; Ralstonia; Pseudomonas; Stenotrophomonas*; and *Xanthomonas*.

The host cell can be selected from "Gram-negative Proteobacteria Subgroup 11." "Gram-negative Proteobacteria Subgroup 11" is defined as the group of Proteobacteria of the genera: *Pseudomonas; Stenotrophomonas*; and *Xanthomonas*. The host cell can be selected from "Gram-negative Proteobacteria Subgroup 12." "Gram-negative Proteobacteria Subgroup 12" is defined as the group of Proteobacteria of the following genera: *Burkholderia*; Ralstonia; *Pseudomonas*. The host cell can be selected from "Gram-negative Proteobacteria Subgroup 13." "Gram-negative Proteobacteria Subgroup 13" is defined as the group of Proteobacteria of the following genera: *Burkholderia; Ralstonia; Pseudomonas*; and *Xanthomonas*. The host cell can be selected from "Gram-negative Proteobacteria Subgroup 14." "Gram-negative Proteobacteria Subgroup 14" is defined as the group of Proteobacteria of the following genera: *Pseudomonas* and *Xanthomonas*. The host cell can be selected from "Gram-negative Proteobacteria Subgroup 15." "Gram-negative Proteobacteria Subgroup 15" is defined as the group of Proteobacteria of the genus *Pseudomonas*.

The host cell can be selected from "Gram-negative Proteobacteria Subgroup 16." "Gram-negative Proteobacteria Subgroup 16" is defined as the group of Proteobacteria of the following *Pseudomonas* species (with the ATCC or other deposit numbers of exemplary strain(s) shown in parenthesis): *P. abietaniphila* (ATCC 700689); *P. aeruginosa* (ATCC 10145); *P. alcaligenes* (ATCC 14909); *P. anguilliseptica* (ATCC 33660); *P. citronellolis* (ATCC 13674); *P. flavescens* (ATCC 51555); *P. mendocina* (ATCC 25411); *P. nitroreducens* (ATCC 33634); *P. oleovorans* (ATCC 8062); *P. pseudoalcaligenes* (ATCC 17440); *P. resinovorans* (ATCC 14235); *P. straminea* (ATCC 33636); *P. agarici* (ATCC 25941); *P. alcaliphila; P. alginovora; P. andersonii; P. asplenii* (ATCC 23835); *P. azelaica* (ATCC 27162); *P. beijerinckii* (ATCC 19372); *P. borealis; P. boreopolis* (ATCC 33662); *P. brassicacearum; P. butanovora* (ATCC 43655); *P. cellulosa* (ATCC 55703); *P. aurantiaca* (ATCC 33663); *P. chlororaphis* (ATCC 9446, ATCC 13985, ATCC 17418, ATCC 17461); *P. fragi* (ATCC 4973); *P. lundensis* (ATCC 49968); *P. taetrolens* (ATCC 4683); *P. cissicola* (ATCC 33616); *P. coronafaciens; P. diterpeniphila; P. elongata* (ATCC 10144); *P. flectens* (ATCC 12775); *P. azotoformans; P. brenneri; P. cedrella; P. corrugata* (ATCC 29736); *P. extremorientalis; P. fluorescens* (ATCC 35858); *P. gessardii; P. libanensis; P. mandelii* (ATCC 700871); *P. marginalis* (ATCC 10844); *P. migulae; P. mucidolens* (ATCC 4685); *P. orientalis; P. rhodesiae; P. synxantha* (ATCC 9890); *P. tolaasii* (ATCC 33618); *P. veronii* (ATCC 700474); *P. frederiksbergensis; P. geniculata* (ATCC 19374); *P. gingeri; P. graminis; P. grimontii; P. halodenitrificans; P. halophila; P. hibiscicola* (ATCC 19867); *P. huttiensis* (ATCC 14670); *P. hydrogenovora; P. jessenii* (ATCC 700870); *P. kilonensis; P. lanceolata* (ATCC 14669); *P. lini; P. marginata* (ATCC 25417); *P. mephitica* (ATCC 33665); *P. denitrificans* (ATCC 19244); *P. pertucinogena* (ATCC 190); *P. pictorum* (ATCC 23328); *P. psychrophila; P. fulva* (ATCC 31418); *P. monteilii* (ATCC 700476); *P. mosselii; P. oryzihabitans* (ATCC 43272); *P. plecoglossicida* (ATCC 700383); *P. putida* (ATCC 12633); *P. reactans; P. spinosa* (ATCC 14606); *P. balearica; P. luteola* (ATCC 43273); *P. stutzeri* (ATCC 17588); *P. amygdali* (ATCC 33614); *P. avellanae* (ATCC 700331); *P. caricapapayae* (ATCC 33615); *P. cichorii* (ATCC 10857); *P. ficuserectae* (ATCC 35104); *P. fuscovaginae; P. meliae* (ATCC 33050); *P. syringae* (ATCC 19310); *P. viridiflava* (ATCC 13223); *P. thermocarboxydovorans* (ATCC 35961); *P. thermotolerans; P. thivervalensis; P. vancouverensis* (ATCC 700688); *P. wisconsinensis*; and *P. xiamenensis*.

The host cell can be selected from "Gram-negative Proteobacteria Subgroup 17." "Gram-negative Proteobacteria Subgroup 17" is defined as the group of Proteobacteria known in the art as the "fluorescent Pseudomonads" including those belonging, e.g., to the following *Pseudomonas* species: *P. azotoformans; P. brenneri; P. cedrella; P. corrugata; P. extremorientalis; Pseudomonas fluorescens; P. gessardii; P. libanensis; Pseudomonas mandelii; P. marginalis; P. migulae; P. mucidolens; P. orientalis; P. rhodesiae; P. synxantha; P. tolaasii*; and *P. veronii*.

The host cell can be selected from "Gram(−) Proteobacteria Subgroup 18." "Gram(−) Proteobacteria Subgroup 18" is defined as the group of all subspecies, varieties, strains, and other sub-special units of the species *P. fluorescens*, including those belonging, e.g., to the following (with the ATCC or other deposit numbers of exemplary strain(s) shown in parenthesis): *P. fluorescens* biotype A, also called biovar 1 or biovar I (ATCC 13525); *P. fluorescens* biotype B, also called biovar 2 or biovar II (ATCC 17816); *P. fluorescens* biotype C, also called biovar 3 or biovar III (ATCC 17400); *P. fluorescens* biotype F, also called biovar 4 or biovar IV (ATCC 12983); *P. fluorescens* biotype G, also called biovar 5 or biovar V (ATCC 17518); *P. fluorescens* biovar VI; *P. fluorescens* PfO-1; *P. fluorescens* Pf-5 (ATCC BAA-477); *P. fluorescens* SBW25; and *P. fluorescens* subsp. *cellulosa* (NCIMB 10462).

The host cell can be selected from "Gram(−) Proteobacteria Subgroup 19." "Gram(−) Proteobacteria Subgroup 19" is defined as the group of all strains of *P. fluorescens* biotype A. A particularl strain of this biotype is *P. fluorescens* strain MB101 (see U.S. Pat. No. 5,169,760 to Wilcox), and derivatives thereof. An example of a derivative thereof is P. fluorescens strain MB214, constructed by inserting into the MB101 chromosomal asd (aspartate dehydrogenase gene) locus, a native *E. coli* PlacI-lacI-lacZYA construct (i.e. in which PlacZ was deleted).

In one embodiment, the host cell is any of the Proteobacteria of the order Pseudomonadales. In a particular embodiment, the host cell is any of the Proteobacteria of the family Pseudomonadaceae.

Additional *P. fluorescens* strains that can be used in the present invention include *P. fluorescens* Migula and *P. fluorescens* Loitokitok, having the following ATCC designations: (NCIB 8286); NRRL B-1244; NCIB 8865 strain CO1; NCIB 8866 strain $CO_2$; 1291 (ATCC 17458; IFO 15837; NCIB 8917; LA; NRRL B-1864; pyrrolidine; PW2 (ICMP 3966; NCPPB 967; NRRL B-899); 13475; NCTC 10038; NRRL B-1603 (6; IFO 15840); 52-1C; CCEB 488-A (BU 140); CCEB 553 (IEM 15/47); IAM 1008 (AHH-27); IAM 1055 (AHH-23); 1 (IFO 15842); 12 (ATCC 25323; NIH 11; den Dooren de Jong 216); 18 (IFO 15833; WRRL P-7); 93 (TR-10); 108 (52-22; IFO 15832; 143 (IFO 15836; PL); 149 (2-40-40; IFO 15838; 182 (IFO 3081; PJ 73); 184 (IFO 15830); 185 (W2 L-1); 186 (IFO 15829; PJ 79); 187 (NCPPB 263); 188 (NCPPB 316); 189 (PJ227; 1208); 191 (IFO 15834; PJ 236; 22/1); 194 (Klinge R-60; PJ 253); 196 (PJ 288); 197 (PJ 290); 198 (PJ 302); 201 (PJ 368); 202 (PJ 372); 203 (PJ 376); 204 (IFO 15835; PJ 682); 205 (PJ 686); 206 (PJ 692); 207 (PJ 693); 208 (PJ 722); 212 (PJ 832); 215 (PJ 849); 216 (PJ 885); 267 (B-9); 271 (B-1612); 401 (C71A; IFO 15831; PJ 187); NRRL B-3178 (4; IFO 15841); KY 8521; 3081; 30-21; (IFO 3081); N; PYR; PW; D946-

B83 (BU 2183; FERM-P 3328); P-2563 (FERM-P 2894; IFO 13658); IAM-1126 (43F); M-1; A506 (A5-06); A505 (A5-05-1); A526 (A5-26); B69; 72; NRRL B-4290; PMW6 (NCIB 11615); SC 12936; A1 (IFO 15839); F 1847 (CDC-EB); F 1848 (CDC 93); NCIB 10586; P17; F-12; AmMS 257; PRA25; 6133D02; 6519E01; Ni; SC15208; BNL-WVC; NCTC 2583 (NCIB 8194); H13; 1013 (ATCC 11251; CCEB 295); IFO 3903; 1062; or Pf-5.

Fermentation

The term "fermentation" includes both embodiments in which literal fermentation is employed and embodiments in which other, non-fermentative culture modes are employed. Fermentation may be performed at any scale. In one embodiment, the fermentation medium may be selected from among rich media, minimal media, and mineral salts media; a rich medium may be used, but is typically avoided. In another embodiment either a minimal medium or a mineral salts medium is selected. In still another embodiment, a minimal medium is selected.

Mineral salts media consists of mineral salts and a carbon source such as, e.g., glucose, sucrose, or glycerol. Examples of mineral salts media include, e.g., M9 medium, *Pseudomonas* medium (ATCC 179), Davis and Mingioli medium (see, B D Davis & E S Mingioli (1950) *J. Bact.* 60:17-28). The mineral salts used to make mineral salts media include those selected from among, e.g., potassium phosphates, ammonium sulfate or chloride, magnesium sulfate or chloride, and trace minerals such as calcium chloride, borate, and sulfates of iron, copper, manganese, and zinc. Typically, no organic nitrogen source, such as peptone, tryptone, amino acids, or a yeast extract, is included in a mineral salts medium. Instead, an inorganic nitrogen source is used and this may be selected from among, e.g., ammonium salts, aqueous ammonia, and gaseous ammonia. A mineral salts medium will typically contain glucose as the carbon source. In comparison to mineral salts media, minimal media can also contain mineral salts and a carbon source, but can be supplemented with, e.g., low levels of amino acids, vitamins, peptones, or other ingredients, though these are added at very minimal levels.

In one embodiment, media can be prepared using the components listed in Table 7 below. The components can be added in the following order: first $(NH_4)HPO_4$, $KH_2PO_4$ and citric acid can be dissolved in approximately 30 liters of distilled water; then a solution of trace elements can be added, followed by the addition of an antifoam agent, such as Ucolub N 115. Then, after heat sterilization (such as at approximately 121° C.), sterile solutions of glucose $MgSO_4$ and thiamine-HCL can be added. Control of pH at approximately 6.8 can be achieved using aqueous ammonia. Sterile distilled water can then be added to adjust the initial volume to 37l minus the glycerol stock (123 mL). The chemicals are commercially available from various suppliers, such as Merck. This media can allow for a high cell density cultivation (HCDC) for growth of *Pseudomonas* species and related bacteria. The HCDC can start as a batch process which is followed by a two-phase fed-batch cultivation. After unlimited growth in the batch part, growth can be controlled at a reduced specific growth rate over a period of 3 doubling times in which the biomass concentration can increased several fold. Further details of such cultivation procedures is described by Riesenberg, D et al. (1991) "High cell density cultivation of *Escherichia coli* at controlled specific growth rate" *J Biotechnol* 20 (1):17-27.

TABLE 7

Medium composition

| Component | Initial concentration |
|---|---|
| $KH_2PO_4$ | 13.3 g l$^{-1}$ |
| $(NH_4)_2HPO_4$ | 4.0 g l$^{-1}$ |
| Citric acid | 1.7 g l$^{-1}$ |
| $MgSO_4 \cdot 7H_2O$ | 1.2 g l$^{-1}$ |
| Trace metal solution | 10 ml l$^{-1}$ |
| Thiamin HCl | 4.5 mg l$^{-1}$ |
| Glucose-$H_2O$ | 27.3 g l$^{-1}$ |
| Antifoam Ucolub N115 | 0.1 ml l$^{-1}$ |
| Feeding solution | |
| $MgSO_4 \cdot 7H_2O$ | 19.7 g l$^{-1}$ |
| Glucose-$H_2O$ | 770 g l$^{-1}$ |
| $NH_3$ | 23 g |
| Trace metal solution | |
| Fe(lll) citrate | 6 g l$^{-1}$ |
| $MnCl_2 \cdot 4H_2O$ | 1.5 g l$^{-1}$ |
| $ZmCH_2COOl_2 \cdot 2H_2O$ | 0.8 g l$^{-1}$ |
| $H_3BO_3$ | 0.3 g l$^{-1}$ |
| $Na_2MoO_4 \cdot 2H_2O$ | 0.25 g l$^{-1}$ |
| $CoCl_2 \cdot 6H_2O$ | 0.25 g l$^{-1}$ |
| $CuCl_2 \cdot 2H_2O$ | 0.15 g l$^{-1}$ |
| ethylene dinitrilo-tetracetic acid $Na_2 \cdot 2H_2O$ (Tritriplex III, Merck) | 0.84 g l$^{-1}$ |

The expression system according to the present invention can be cultured in any fermentation format. For example, batch, fed-batch, semi-continuous, and continuous fermentation modes may be employed herein.

The expression systems according to the present invention are useful for transgene expression at any scale (i.e. volume) of fermentation. Thus, e.g., microliter-scale, centiliter scale, and deciliter scale fermentation volumes may be used; and 1 Liter scale and larger fermentation volumes can be used. In one embodiment, the fermentation volume will be at or above 1 Liter. In another embodiment, the fermentation volume will be at or above 5 Liters, 10 Liters, 15 Liters, 20 Liters, 25 Liters, 50 Liters, 75 Liters, 100 Liters, 200 Liters, 500 Liters, 1,000 Liters, 2,000 Liters, 5,000 Liters, 10,000 Liters or 50,000 Liters.

In the present invention, growth, culturing, and/or fermentation of the transformed host cells is performed within a temperature range permitting survival of the host cells, such as a temperature within the range of about 4° C. to about 55° C., inclusive. In addition, "growth" is used to indicate both biological states of active cell division and/or enlargement, as well as biological states in which a non-dividing and/or non-enlarging cell is being metabolically sustained, the latter use being synonymous with the term "maintenance."

Cell Density

An additional advantage in using *P. fluorescens* in expressing recombinant mammalian proteins includes the capacity of *P. fluorescens* to be grown in high cell densities compared to *E. coli* or other bacterial expression systems. To this end, *P. fluorescens* expressions systems according to the present invention can provide a cell density of about 20 g/L or more. The *P. fluorescens* expressions systems according to the present invention can likewise provide a cell density of at least about 70 g/L, as stated in terms of biomass per volume, the biomass being measured as dry cell weight.

In one embodiment, the cell density will be at least 20 g/L. In another embodiment, the cell density will be at least 25 g/L, 30 g/L, 35 g/L, 40 g/L, 45 g/L, 50 g/L, 60 g/L, 70 g/L, 80 g/L, 90 g/L., 100 g/L, 110 g/L, 120 g/L, 130 g/L, 140 g/L, or at least 150 g/L.

In another embodiments, the cell density at induction will be between 20 g/L and 150 g/L; 20 g/L and 120 g/L; 20 g/L and 80 g/L; 25 g/L and 80 g/L; 30 g/L and 80 g/L; 35 g/L and 80 g/L; 40 g/L and 80 g/L; 45 g/L and 80 g/L; 50 g/L and 80 g/L; 50 g/L and 75 g/L; 50 g/L and 70 g/L; 40 g/L and 80 g/L.

Isolation and Purification

The proteins of this invention may be isolated purified to substantial purity by standard techniques well known in the art, including including, but not limited to, ammonium sulfate or ethanol precipitation, acid extraction, anion or cation exchange chromatography, phosphocellulose chromatography, hydrophobic interaction chromatography, affinity chromatography, nickel chromatography, hydroxylapatite chromatography, reverse phase chromatography, lectin chromatography, preparative electrophoresis, detergent solubilization, selective precipitation with such substances as column chromatography, immunopurification methods, and others. For example, proteins having established molecular adhesion properties can be reversibly fused a ligand. With the appropriate ligand, the protein can be selectively adsorbed to a purification column and then freed from the column in a relatively pure form. The fused protein is then removed by enzymatic activity. In addition, protein can be purified using immunoaffinity columns or Ni-NTA columns. General techniques are further described in, for example, R. Scopes (1982) *Protein Purification: Principles and Practice*, Springer-Verlag: N.Y.; Deutscher (1990) *Guide to Protein Purification*, Academic Press; U.S. Pat. No. 4,511,503; S. Roe (2001) *Protein Purification Techniques: A Practical Approach*, Oxford Press; D. Bollag, et al. (1996) *Protein Methods*, Wiley-Lisa, Inc.; AK Patra et al. (2000) *Protein Expr Purif*, 18 (2):182-92; and R. Mukhija, et al. (1995) *Gene* 165 (2):303-6. See also, for example, Deutscher (1990) "Guide to Protein Purification," *Methods in Enzymology* vol. 182, and other volumes in this series; Coligan, et al. (1996 and periodic Supplements) *Current Protocols in Protein Science*, Wiley/Greene, NY; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See also, for example: Hochuli (1989) *Chemische Industrie* 12:69-70; Hochuli (1990) "Purification of Recombinant Proteins with Metal Chelate Absorbent" in Setlow (ed.) *Genetic Engineering, Principle and Methods* 12:87-98, Plenum Press, NY; and Crowe, et al. (1992) *QIAexpress: The High Level Expression & Protein Purification System* QUIAGEN, Inc., Chatsworth, Calif.

Detection of the expressed protein is achieved by methods known in the art and include, for example, radioimmunoassays, Western blotting techniques or immunoprecipitation.

The recombinantly produced and expressed enzyme can be recovered and purified from the recombinant cell cultures by numerous methods, for example, high performance liquid chromatography (HPLC) can be employed for final purification steps, as necessary.

Certain proteins expressed in this invention may form insoluble aggregates ("inclusion bodies"). Several protocols are suitable for purification of proteins from. inclusion bodies. For example, purification of inclusion bodies typically involves the extraction, separation and/or purification of inclusion bodies by disruption of the host cells, e.g., by incubation in a buffer of 50 mM TRIS/HCl pH 7.5, 50 mM NaCl, 5 mM $MgCl_2$, 1 mM DTT, 0.1 mM ATP, and 1 mM PMSF. The cell suspension is typically lysed using 2-3 passages through a French Press. The cell suspension can also be homogenized using a Polytron (Brinkrnan Instruments) or sonicated on ice. Alternate methods of lysing bacteria are apparent to those of skill in the art (see, e.g., Sambrook, J., E. F. Fritsch and T. Maniatis eds. (1989) "Molecular Cloning: A Laboratory Manual", 2d ed., Cold Spring Harbor Laboratory Press; Ausubel et al., eds. (1994) *Current Protocols in Molecular Biology*).

If necessary, the inclusion bodies can be solubilized, and the lysed cell suspension typically can be centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art.

Alternatively, it is possible to purify the recombinant proteins from the host periplasm. After lysis of the host cell, when the recombinant protein is exported into the periplasm of the host cell, the periplasmic fraction of the bacteria can be isolated by cold osmotic shock in addition to other methods known to those skilled in the art. To isolate recombinant proteins from the periplasm, for example, the bacterial cells can be centrifuged to form a pellet. The pellet can be resuspended in a buffer containing 20% sucrose. To lyse the cells, the bacteria can be centrifuged and the pellet can be resuspended in ice-cold 5 mM $MgSO_4$ and kept in an ice bath for approximately 10 minutes. The cell suspension can be centrifuged and the supernatant decanted and saved. The recombinant proteins present in the supernatant can be separated from the host proteins by standard separation techniques well known to those of skill in the art.

An initial salt fractionation can separate many of the unwanted host cell proteins (or proteins derived from the cell culture media) from the recombinant protein of interest. One such example can be ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

The molecular weight of a recombinant protein can be used to isolated it from proteins of greater and lesser size using ultrafiltration through membranes of different pore size (for example, Amicon or Millipore membranes). As a first step, the protein mixture can be ultrafiltered through a membrane with a pore size that has a lower molecular weight cut-off than the molecular weight of the protein of interest. The retentate of the ultrafiltration can then be ultrafiltered against a membrane with a molecular cut off greater than the molecular weight of the protein of interest. The recombinant protein will pass through the membrane into the filtrate. The filtrate can then be chromatographed as described below.

Recombinant protiens can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Renaturation and Refolding

Insoluble protein can be renatured or refolded to generate secondary and tieriary protein structure conformation. Protein refolding steps can be used, as necessary, in completing configuration of the recombinant product. Refolding and renaturation can be accomplished using an agent that is known in the art to promote dissociation/association of proteins. For example, the protein can be incubated with dithiothreitol followed by incubation with oxidized glutathione disodium salt followed by incubation with a buffer containing a refolding agent such as urea.

Recombinant protein can also be renatured, for example, by dialyzing it against phosphate-buffered saline (PBS) or 50 mM Na-acetate, pH 6 buffer plus 200 mM NaCl. Alternatively, the protein can be refolded while immobilized on a column, such as the Ni-NTA column by using a linear 6M-1M urea gradient in 500 mM NaCl, 20% glycerol, 20 mM Tris/HCl pH 7.4, containing protease inhibitors. The renaturation can be performed over a period of 1.5 hours or more. After renaturation the proteins can be eluted by the addition of 250 mM immidazole. Immidazole can be removed by a final dialyzing step against PBS or 50 mM sodium acetate pH 6 buffer plus 200 mM NaCl. The purified protein can be stored at 4° C. or frozen at −80° C.

Other methods include, for example, those that may be described in: M H Lee et al. (2002) *Protein Expr. Purif.* 25 (1):166-73; W. K. Cho et al. (2000) *J. Biotechnology* 77 (2-3):169-78; Deutscher (1990) "Guide to Protein Purification," *Methods in Enzymology* vol. 182, and other volumes in this series; Coligan, et al. (1996 and periodic Supplements) *Current Protocols in Protein Science*, Wiley/Greene, NY; S. Roe (2001) *Protein Purification Techniques: A Practical Approach*, Oxford Press; D. Bollag, et al. (1996) *Protein Methods*, Wiley-Lisa, Inc.

Active Protein or Peptide Analysis

Typically, an "active" protein includes proteins that have a biological function or biological effect comparable to the corresponding native protein. In the context of proteins this typically means that a polynucleotide or polypeptide comprises a biological function or effect that has at least about 20%, about 50%, about 60%, about 70%, about 75%, about 80%, about 85%, about 90%, about 95%, about 98% or 100% biological function compared to the corresponding native protein using standard parameters. The determination of protein activity can be performed utilizing corresponding standard, targeted comparative biological assays for particular proteins. One indication that a recombinant protein biological function or effect is that the recombinant polypeptide is immunologically cross reactive with the native polypeptide.

Active proteins typically have a specific activity of at least 20%, 30%, 40%, 50%, 60%, 70%, 80%, 90%, or 95% that of the native mammalian protein. Further, the substrate specificity ($k_{cat}/K_m$) is optionally substantially similar to the native mammalian protein. Typically, $k_{cat}/K_m$ will be at least 30%, 40%, 50%, 60%, 70%, 80%, or 90% that of the native protein. Methods of assaying and quantifying measures of protein and peptide activity and substrate specificity ($k_{cat}/K_m$), are well known to those of skill in the art.

The activity of a recombinant mammalian protein can be measured by any protein specific conventional or standard in vitro or in vivo assay known in the art. The activity of the *Pseudonmonas* produced recombinant mammalian protein can be compared with the activity of the corresponding native mammalian protein to determine whether the recombinant mammalian protein exhibits substantially similar or equivalent activity to the activity generally observed in the native protein under the same or similar physiological conditions.

The activity of the recombinant protein can be compared with a previously established native protein standard activity. Alternatively, the activity of the recombinant protein can be determined in a simultaneous, or sunstantially simultaneous, comparative assay with the native protein. For example, an in vitro assays can be used to determine any detectable interaction between a recombinant protein and a target, e.g. between an expressed enzyme and substrate, between expressed hormone and hormone receptor, between expressed antibody and antigen, etc. Such detection can include the measurement of colorimetric changes, proliferation changes, cell death, cell repelling, changes in radioactivity, changes in solubility, changes in molecular weight as measured by gel electrophoresis and/or gel exclusion methods, phosphorylation abilities, antibody specificity assays such as ELISA assays, etc. In addition, in vivo assays include, but are not limited to, assays to detect physiological effects of the *Pseudomonas* produced protein in comparison to physiological effects of the native protein, e.g. weight gain, change in electrolyte balance, change in blood clotting time, changes in clot dissolution and the induction of antigenic response. Generally, any in vitro or in vivo assay can be used to determine the active nature of the *Pseudomonas* produced recombinant mammalian protein that allows for a comparative analysis to the native protein so long as such activity is assayable. Alternatively, the proteins produced in the present invention can be assayed for the ability to stimulate or inhibit interaction between the protein and a molecule that normally interacts with the protein, e.g. a substrate or a component of the signal pathway that the native protein normally interacts. Such assays can typically include the steps of combining the protein with a substrate molecule under conditions that allow the protein to interact with the target molecule, and detect the biochemical consequence of the interaction with the protein and the target molecule.

Assays that can be utilized to determine protein activity are described, for example, in: Ralph, P. J., et al. (1984) *J. Immunol.* 132:1858; Saiki et al. (1981) *J. Immunol.* 127: 1044; Steward, W. E. 11 (1980) *The Interferon Systems*. Springer-Verlag, Vienna and New York; Broxmeyer, H. E., et al. (1982) *Blood* 60:595; Sambrook, J., E. F. Fritsch and T. Maniatis eds. (1989) "Molecular Cloning: A Laboratory Manual", 2d ed., Cold Spring Harbor Laboratory Press; Berger, S. L. and A. R. Kimmel eds. (1987) "Methods in Enzymology: Guide to Molecular Cloning Techniques", Academic Press; AK Patra et al. (2000) *Protein Expr Purif* 18 (2):182-92; Kodama et al. (1986) *J. Biochem.* 99:1465-1472; Stewart et al. (1993) *Proc. Nat'l Acad. Sci. USA* 90:5209-5213; Lombillo et al. (1995) *J. Cell Biol.* 128:107-115; Vale et al. (1985) *Cell* 42:39-50.

EXAMPLES

Bacterial Strains and Growth Conditions.

Unless otherwise specified, all strains used for all *Pseudomonas* expression testing were based on *P. fluorescens* strain MB101. *E. coli* strains JM109 (Promega), XL2 Blue (Stratagene) or Top 10 (Invitrogen) were used for general cloning. For *E. coli* expression studies, BL21 (DE3) Gold was used. *P. fluorescens* strains were grown in either LB or minimal salts medium supplemented with 15 ug/mL tetracycline and 30 ug/mL kanamycin as needed at 30° C. *E. coli* strains were grown in LB supplemented with 30 ug/mL kanamycin and/or 15 ug/mL chloramphenicol, or 15 ug/mL tetracycline as needed at 37° C. Cells were induced with 0.3 mM IPTG following growth phase.

Protein Activity Detection (ELISA Assay)

Plates were coated by adding 200 μL of the β-galactosidase solution at 10 μg/mL in PBS (pH 7.6) to each well of the microtiter plate. Plates were incubated at room temperature for 16 hrs, then washed 3 times with 200 μL PBS+0.1% Tween-20 (PBS-T). Primary antibody was diluted in PBS with 2% nonfat dry milk (w/v). 200 μL of the diluted antibody was added to each well and incubated at room temperature for 1 hr. The plates were then washed 4 times with 200 μL PBS-T. The secondary antibody was also diluted in PBS with 2% non fat dry milk (w/v) and to each well, 200 μL was added and incubated at room temperature for 1.5-2 hours. The plates were then washed 4 times with PBS-T. A tertiary antibody is used to detect the scFv antibodies: alkaline phosphatase conjugated sheep anti-mouse antibody (Sigma-Aldrich, St. Louis, Mo., USA cat #A5324). To each desired well was added 200 μL of diluted antibody solution (or PBS-T) and incubated at room temperature for 1.5 hours. The plates were then washed 4 times with PBS-T. To each well was added 200 μl of the freshly prepared Sigma Fast pNPP substrate (Sigma catalogue #R-2770). After 30 minutes, the reaction was stopped by adding 50 μL 3M NaOH to each well and absorbance was read at 405 nm.

Fermentation

The inoculum for the fermentor culture for *P. fluorescens* is generated by inoculating a shake flask containing 600 mL of a chemically defined medium supplemented with yeast extract and dextrose. Tetracycline is typically added to ensure maintenance of the recombinant plasmid in the starter culture during its overnight incubation as well as in the fermentor. The shake flask culture is then aseptically transferred to a 20 L fermentor containing a chemically defined medium designed to support a high biomass, without yeast extract supplementation. Oxygen is maintained at a positive level in the liquid culture by regulating the air flow into the fermentor and the agitator mixing rate; the pH is maintained at greater than 6.0 through the addition of aqueous ammonia. The fed-batch high density fermentation process is divided into an initial growth phase of approximately 24 h and gene expression (induction) phase in which an inducer is added to initiate recombinant gene expression. Glucose, in the form of corn syrup, is fed throughout the fermentation process at limiting concentrations. The target cell density for initiating the induction phase is typically 150 OD units at 575 nm. The induction phase of the fermentation is typically allowed to go for approximately 45 to 55 hours. During this phase, samples are withdrawn from the fermentor for various analyses to determine the level of target gene expression, cell density, etc.

For each fermentation experiment for *E. coli*, a frozen glycerol stock is removed from −80° C. storage, thawed and diluted before inoculating a shake flask containing 600 mL of LB broth supplemented with kanamycin. The shake flask culture is incubated at 37° C. with shaking at 300 rpm overnight and then aseptically transferred to a 20 L fermentor containing complex medium. Temperature in the fermentor is maintained at 37° C., pH at 7 through the addition of aqueous ammonia and phosphoric acid, and dissolved oxygen at greater than 20%. After a brief initial batch phase, glycerol is fed at rates increased stepwise to maintain excess carbon. When the cell density reaches 24-28 OD units at 600 nm, recombinant expression is effected by addition of an inducer, such as isopropyl-thiogalactoside (IPTG). The induction phase of the fermentation typically continues for approximately 3 to 5 hours as the fermentor reached volumetric capacity or as the growth rate began to decrease significantly. During this phase, samples are withdrawn from the fermentor for various analyses to determine the level of target gene expression, cell density, etc.

Cell Fractionation and SDS-PAGE Analysis.

Samples are normalized to A575=30, and 1 mL normalized culture is pelleted. Cells are resuspended in 1 mL lysis buffer (50 mM Tris base; 200 mM NaCl; 5% v/v glycerol; 20 mM EDTA disodium salt; 0.5% v/v Triton X-100; 1 mM DTT). A protease inhibitor cocktail specific for bacterial lysates (Sigma#P8465) is added to a 1× concentration. The resuspended cells are added to a 2 ml screw cap microfuge tube approximately ¾ full with 0.1 mm glass beads and the cells are mechanically lysed using 4, 1 minute incubations in a BioSpec bead mill at the highest setting. Cells are kept on ice between incubations. Approximately 100 uL of lysed cell solution is removed from beads, transferred into a new tube and pelleted. The supernatant (soluble fraction) is removed to a new tube. The pellet (insoluble fraction) is resuspended in an equal volume (100 uL) of lysis buffer plus protease inhibitor. Five uL of each sample is added to 5 uL of 2×LDS loading buffer (Invitrogen) and loaded onto a 4-12% or 10% Bis-Tris NuPAGE gel (Invitrogen) and run in either 1×MES or 1×MOPS buffer as indicated.

Example 1

Expression of scFV in the Cytoplasm

Single chain antibody fragments (scFV) are finding increased use as diagnostic and therapeutic agents. These relatively small proteins are made by fusing together genes coding the variable light and heavy chains of an immunoglobulin.

Cloning of Gal13 scFv

The Gal13 scFv gene (Genbank accession number AF238290), cloned into the phage display vector pCAN-TAB6, (see P Martineau et al. (1998) *J. Mol. Biol.* 280 (1):117-27) was used as template to amplify a 774 base pair product, which was subsequently cloned into the pCR2.1 TOPO vector (Invitrogen, Carlsbad, Calif., USA). The scFv gene was excised from the TOPO vector with SpeI and SalI restriction enzymes (New England Biolabs, Beverly, Mass., USA) and cloned into the SpeI and XhoI sites of the *P. fluorescens* vector pMYC1803, downstream of the Ptac promoter, to produce pDOW1117. The resulting plasmids were electroporated into *P. fluorescens*. The Gal13 gene was cloned into the pET24d+ expression vector (Novagen, Madison, Wis., USA), following amplification such that SalI and NcoI sites flanked the coding sequence. The PCR products were digested with SalI and NcoI and cloned into the same sites of pET24d+ vector downstream of the T7 promoter. The newly formed construct was then used to transform XL2 Blue competent cells. Once sequence was confirmed, the DNA construct was used to transform BL21 (DE3) Gold (Stratagene, San Diego, Calif., USA) for expression.

Expression of a Single Chain Antibody Fragment (scFv) in *E. coli* and *P. fluorescens* scFv molecules were expressed in both *E. coli* and *P. fluorescens*, among them an scFv with binding activity to the *E. coli* protein α-galactosidase single chain antibody gal13 (P. Martineau et al., "Expression of an antibody fragment at high levels in the bacterial cytoplasm," J. Mol. Biol. 280 (1):117-27 (1998)). *P. fluorescens* expressed about six-fold more protein than *E. coli* during 20 L fermentation, with 3.1 g/L yield in *P. fluorescens* and 0.5 g/L yield in *E. coli* as determined by SDS-PAGE and densitometry (see Table 8). *P. fluorescens* expressed about 96% soluble protein, whereas *E. coli* expresses only 48% soluble protein.

TABLE 8

Gal13 fermentation summary (*compared to BSA standards)

| | E. coli | P. fluorescens | Pf/Ec |
|---|---|---|---|
| Fermentation Time (hr) | 8-9 | 70 | 8 |
| Max Gal13 scF titre (*g/L) | 0.4 (85% cv) | 3.1 (24% cv) | 8 |
| Dry biomass (g/L) | ND (30) | 59 | (2) |
| Gal13 scFv/biomass (% w/w) | (1) | 5 | (5) |

Figure 2:
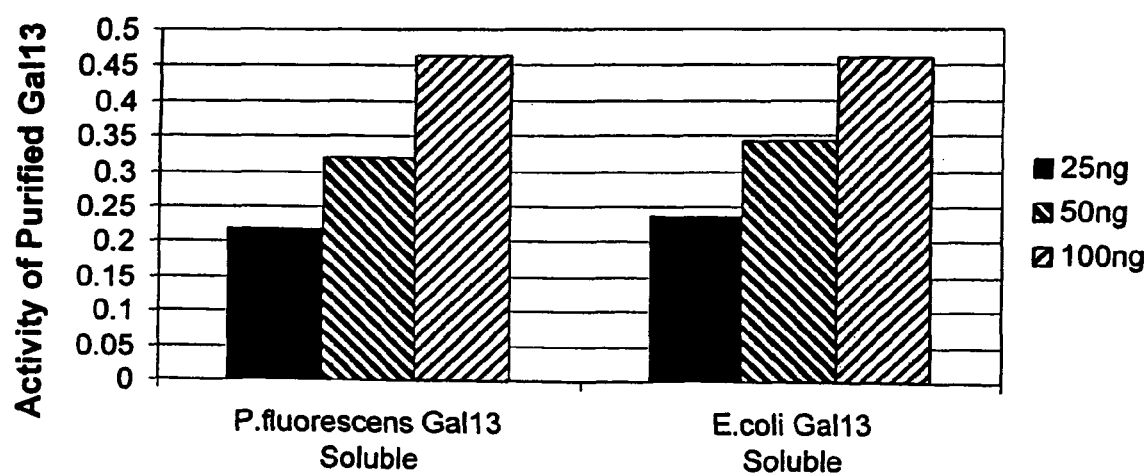
FIG. 2 is a picture of an ELISA showing the activity of purified Gal13 in *P. fluorescens* and *E. coli*.

Material purified from both expression systems was found to be active in an enzyme-linked immunosorbant assay (ELISA) as shown in FIG. 2. Material was also purified from the soluble fraction only of equal lysate volumes from lysates of both strains using affinity chromatography. Finally, the overall volumetric recovery for the *P. fluorescens* process is approximately 20 fold more efficient than for *E. coli*, 1.34 g/L vs. 0.07 g/L.

Example 2

Expression of Human γ-IFN in the Cytoplasm

Cloning of Human Gamma-Interferon

Human gamma interferon (hu-γIFN, Genbank accession X13274) was amplified from a human spleen cDNA library (Invitrogen, Carlsbad, Calif., USA; catalogue #10425-015) such that it lacked the native secretion signal, with the N-terminus of the recombinant γ-IFN beginning as Met-Cys-Tyr-Cys-Gln-Asp-Pro (SEQ ID NO: 28) as described in PW Gray et al. (1982) Nature 298:859-63. The resulting product was cloned into the pCR2.1 TOPO vector and the sequence was confirmed. The hu-γIFN gene was excised from the TOPO vector with SpeI and XhoI restriction enzymes and cloned into the same sites of pMYC1803. In a separate reaction, hu-γIFN was amplified such that AflIII and XhoI sites flanked that coding sequence. The resulting fragment was cloned into the TOPO-TA vector (Invitrogen) and transformed into chemically competent *E. coli* JM109 cells (Promega, Madison, Wis., USA). The gene was isolated by digesting with AflII and XhoI (New England Biolabs), cloned into the NcoI and XhoI sites of pET24d+ (Novagen, Madison, Wis., USA) downstream of the T7 promoter, and transformed into JM109. A positive clone was transformed into *E. coli* BL21 (DE3) cells (Novagen) to test for expression.

Human Gamma-Interferon Purification

Frozen cell paste from *P. fluorescens* cultures was thawed and re-suspended in lysis buffer (50 mM potassium phosphate, pH 7.2 containing 50 mM NaCl, 10 mM EDTA (ethylenediaminetetraacetic acid, catalog number BPII8-500, Fisher Scientific, Springfield, NJ, USA), 1 mM PMSF (phenylmethylsulfonyl fluoride, catalog number P-7626, Sigma, St. Louis, Mo.), 1 mM dithiothreitol (catalog number D-0632, Sigma), and 1 mM benzamidine (catalog number B-6506, Sigma)) at a ratio of about 1 gram cell paste per 2 mL lysis buffer. Cells were broken by three passages through a microfluidizer (model 110Y, Microfluidics Corporation, Newton, Mass., USA). Cell debris and unbroken cells were removed by centrifugation (for 60 min at 23,708×g and 4° C. using a Beckman Coulter centrifuge; model JA 25.50, Beckman Coulter, Inc., Fullerton, Calif., USA). The resulting supernatant (cell-free extracts) was clarified by adding 10% w/v diatomaceous earth (Celite product, World Minerals, Inc., Goleta, Calif., USA) and passing the result through a paper filter (Whatman 1, catalog number 1001-150, Whatman Paper Ltd., Maidstone, Kent, UK)) with vacuum filtration.

Clarified cell extracts were applied to a 3.2 cm×13.5 cm chromatography column of SP-Sepharose FAST FLOW (6% cross-linked agarose bead material; catalog number 17-0709-10, Amersham Biosciences, Piscataway, N.J., USA) equilibrated in buffer A, at a flow rate of 0.5 mL/min. The composition of Buffer A was: 50 mM HEPES, pH 7.8 (i.e. N-(2-hydroxyethyl)piperazine)N'-(2-ethanesulfonic acid), from Fisher Scientific, catalog number BP-310-100), 50 mM NaCl, 1 mM EDTA, and 0.02% sodium azide (catalog number 71289, Sigma Chemical Co.). After loading, the column was washed with 3 column volumes (column volume=108 mL) buffer A and 5 column volumes of buffer A containing 0.4M NaCl. The column was further developed by applying a gradient of 0.4 M to 1 M NaCl in the same buffer at a flow rate of 2 mL/min for a total of 7 column volumes. Fractions containing pure IFN-γ were then pooled and dialyzed against 1×PBS (phosphate-buffered saline, pH 7.2) at 4° C. Protein was concentrated by ultrafiltration (using a YM30 ultrafiltration membrane; catalog no. 13722, from Millipore, Bedford, Mass. USA), then frozen in liquid nitrogen and stored at 80° C.

Expression of Human γ-Interferon in *E. coli* and *P. fluorescens*

Figure 5:
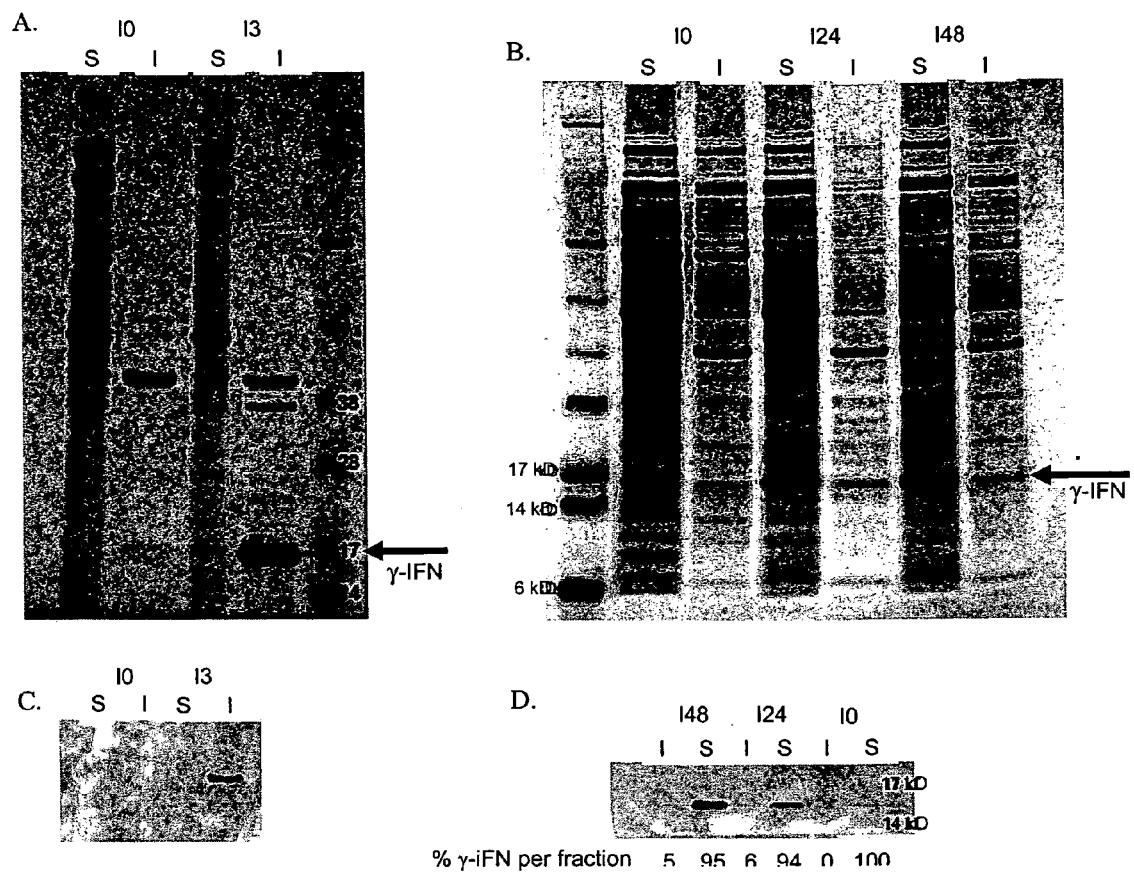
FIG. 5 shows an SDS-PAGE analysis of the expression of γ-IFN in *E. coli* versus *P. fluoresens* cells. Soluble (S) and insoluble (I) fractions of samples taken at 0, 3, 24 and 48 hours post-induction (10, etc.) were resolved. *E. coli* expressed γ-IFN is shown in panel A, *P. fluorescens* expressed γ-IFN is shown in panel B. 5 uL of A575-20 samples were loaded onto a 10% Bis-Tris NuPAGE gel and resolved in 1× MES. Arrows indicate the position of the recombinant protein. Western analyses are shown in panels C (*E. coli*) and D (*P. fluorescens*).
Figure 6:
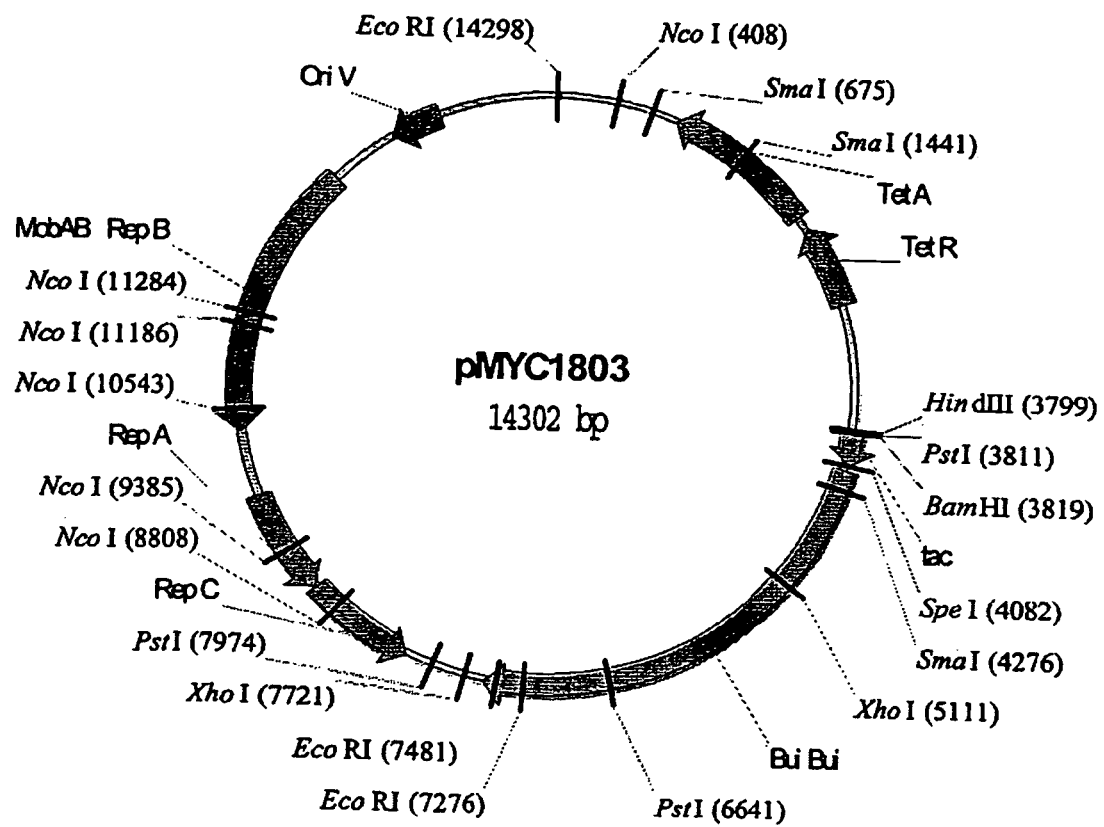
FIG. 6 shows the replacement of the BuiBui toxin gene with the BGI gene at the SpeI and XhoI sites of pMYC1803.

Human γ-interferon is produced commercially by fermentation of *E. coli* expressing the γ-IFN gene. The protein is expressed cytoplasmically in an insoluble and inactive form. In order to produce the recombinant polypeptide as an active pharmaceutical ingredient, the interferon must be recovered, solubilized, refolded, and then purified. All these unit operations add greatly to the cost of goods (COGs) for this protein. A human spleen cDNA library was used as a template to amplify the γIFN cDNA without the native signal sequence and clone into *E. coli* and *P. fluorescens* expression vectors. *P. fluorescens* construct produced ~4 g/L of γIFN protein during a typical 20 L fermentation reaction. SDS-PAGE and Western analyses of soluble and insoluble fractions show that the majority of the protein (95%) is present in the soluble fraction. FIG. 1 shows that hu-γ-IFN purified from the soluble fraction of *P. fluorescens* samples displays activity comparable to a commercially available standard. FIG. 5 and Table 9 show a comparison of expression of γ-IFN between *E. coli* and *P. fluorescens* expression systems.

TABLE 9

γ-IFN fermentation summary (*compared to BSA standards)

|  | E. coli | P. fluorescens | Pf/Ec |
|---|---|---|---|
| Fermentation Time (hr) | 7-9 | 55 | 6 |
| Max γ-IFN titre (*g/L) | 3.9 | 4.5 | 1.5 |
| Dry biomass (g/L) | ~22 | 100 | 4.5 |
| γ-IFN/biomass (% w/w) | ~17.7 | 4.5 | 0.25 |

Assay of Human Gamma Interferon Activity

Cell lines and media: Hela cells (catalogue no. CCL-2) and encephalomyocarditis virus (ECMV, catalogue no. VR-129B) were obtained from the American Type Culture Collection (Manassas, Va.). HeLa cells were maintained in Eagles Modified Essential Medium (Cellgro EMEM, Mediatech, Herdon, Va., USA) with 10% fetal bovine serum (Gibco, Invitrogen, Carlsbad, Calif., USA) at 37° C./5% $CO_2$.

The activity of purified hu-γIFN was assayed using a viral inhibition assay as previously described (J A Lewis (1987) in Lymphokines and Interferons: A Practical Approach M J Clemens et al. (eds.) (IRL Press Ltd, Oxford, England). Briefly, HeLa cells were seeded in a 96-well microtiter plate at $3 \times 10^4$ per well. After 24 hours, purified hu-γIFN isolated from *P. fluorescens*, or *E. coli* recombinant hu-γIFN (from R&D Systems, Minneapolis, Minn., USA), was added to triplicate wells at 0, 0.01 or 0.05 ng per well. After preincubating the cells with hu-γIFN for 24 hours, ECMV was added at varying dilutions to sets of triplicate wells. The cells were incubated for 5 days, after which cell viability was measured using a cell proliferation ELISA that monitors 5-bromo-2'-deoxyuridine incorporation (catalogue no. 1647229, Roche Molecular Biochemicals, Indianapolis, Ind., USA). Results are expressed as absorbance units, with greater absorbance resulting from the presences of a greater number of actively dividing (live) cells.

Example 3

Expression of hGH in the Cytoplasm

Figure 3:
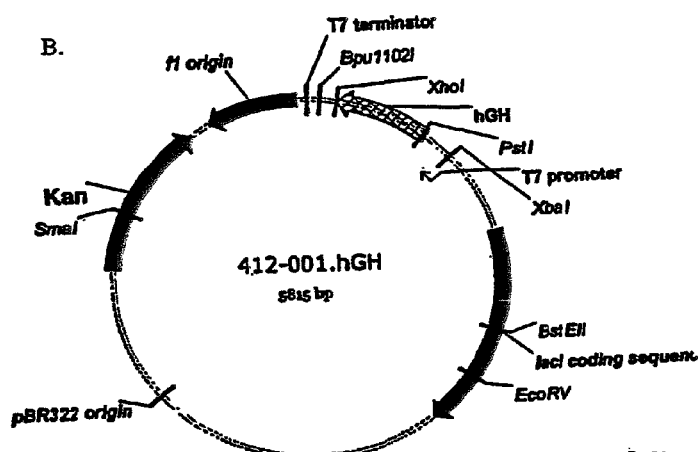
FIG. 3 represents human growth hormone expression constructs. The amino acid sequence of human growth hormone lacking its native secretion signal sequence is shown in A. Plasmid constructs for expression in *P. fluorescens* (pDOW2400) and *E. coli* (412-001.hGH) are shown in B.
Figure 3:
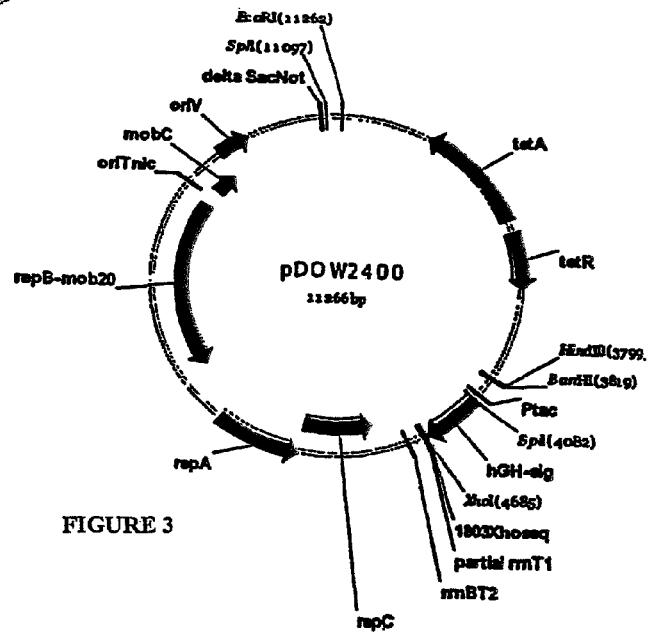

Primers were designed to amplify human growth hormone (hGH) from human cDNA libraries. For this study, hGH was amplified using AmpliTaq polymerase (Perkin Elmer) according to the manufacturer's protocol, using the above plasmid as template and primers ELVIrev and hgh-sig, with a PCR cycling profile of 95° C. 2 minutes (95° C. 60 seconds 42° C. 120 seconds 72° C. 3 minutes) 25×. The resulting product was purified using Wizard PCR DNA purification kit (Promega), digested with SpeI and XhoI restriction enzymes (New England Biolabs) and cloned into the same sites of pMYC1803 (see FIG. 3). A mutation found in the amplified hGH was corrected by using the hgh-sigcorr primer with ELVIrev and repeating the PCR and cloning procedures.

Primers used to clone hGH.

```
hGH-sig   AGAGAACTAGTAAAAAGGAGAAATCCATGTTCCCAACCATTC
          CCTTATC (SEQ ID NO: 4)

HGH-      AGAGAACTAGTAAAAAGGAGAAATCCATGTTCCCAACCATTC
sigcorr   CCTTATCCAGGCCTTTTGAC (SEQ ID NO: 5)

ELVIfor   AGAGAACTAGTAAAAAGGAGAAATCCATGGCTACAGGCTCCC
          GGACGTCC (SEQ ID NO: 6)

ELVIrev   AGAGACTCGAGTCATTAGAAGCCACAGCTGCCCTCCAC
          (SEQ ID NO: 7)
```

Purification of hGH

Following 20 L fermentation, hGH was purified from the insoluble fraction of *E. coli* and *P. fluorescens* cells, with the exception that during DEAE FF elution a gradient from 0 to 0.5M NaCl was used in place of a 0.25M NaCl step.

Expression of Human Growth Hormone in *E. coli* vs. *P. fluorescens*.

The cDNA encoding human growth hormone was amplified from a human pituitary cDNA library. The native secretion signal sequence was removed, and an N-terminal methionine was engineered into the constructs for microbial expression. For *E. coli* expression, the pET25 vector containing the hGH gene was transformed into BL21 (DE3), which contains an integrated T7 polymerase gene necessary for hGH transcription. *P. fluorescens* expression studies were carried out in the MB214 strain, which contains an integrated lacI gene to control expression from the Ptac promoter. Both expression systems were evaluated at the 20 L fermentation scale. As shown in Table 10, *P. fluorescens* (Pf) outperformed *E. coli* (EC) in the amount of protein produced per gram of dry biomass (1.6× as much).

TABLE 10 hGH fermentation summary (*compared to BSA standards)

|  | E. coli | P. fluorescens | Pf/Ec |
|---|---|---|---|
| Fermentation Time (hr) | 7-9 | 55 | 6 |
| Max hGH titre (*g/L) | 2.6 (23% cv) | 7.3 (5% cv) | 3 |
| Dry biomass (g/L) | 37 | 66 | 2 |
| hGH/biomass (% w/w) | 7 | 11 | 1.6 |

Figure 4:
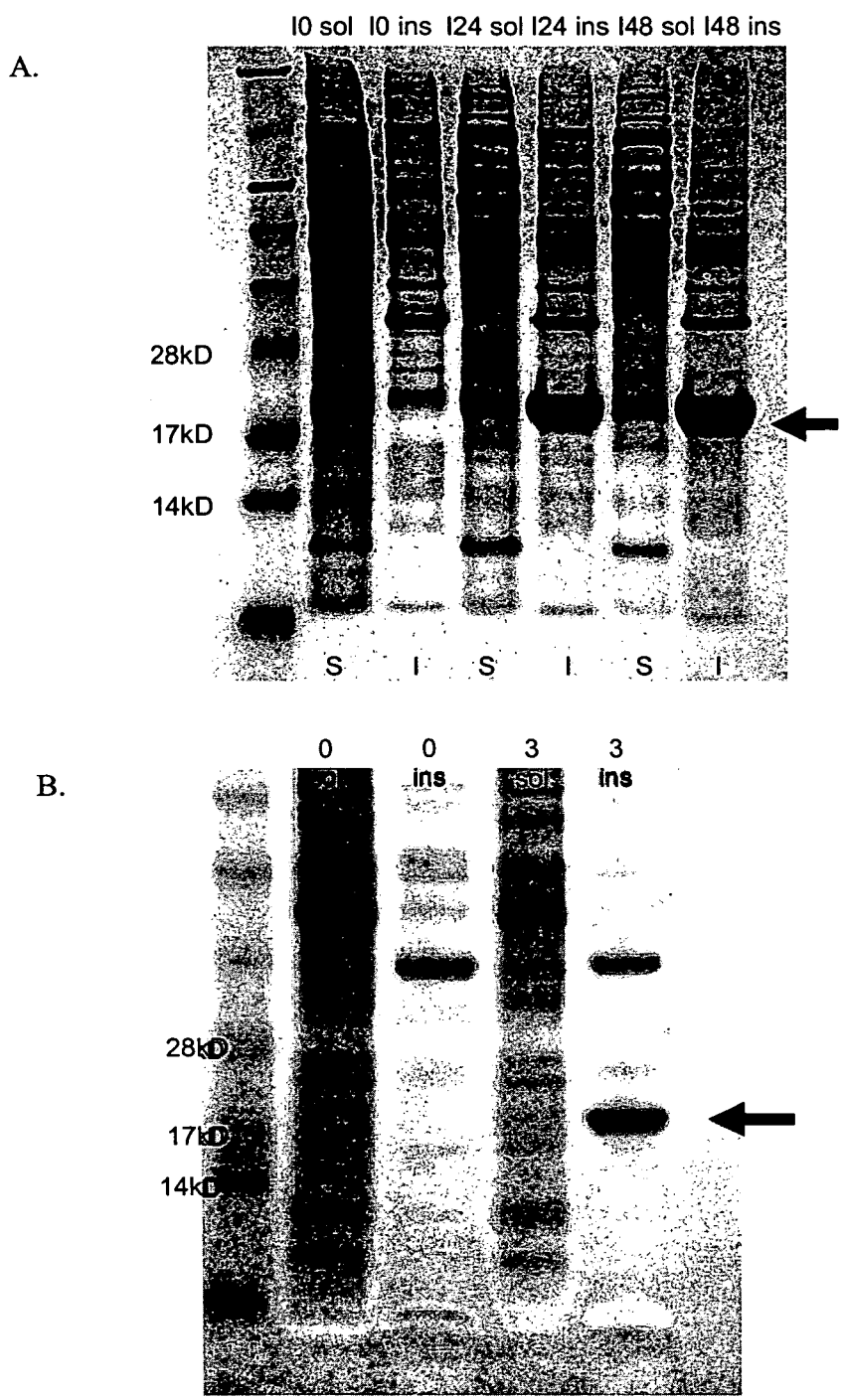
FIG. 4 is a picture of an SDS-PAGE analysis of soluble and insoluble fractions of hGH expressed in *P. fluorescens* and *E. coli*. The time post-induction is denoted by 10, 124, 148, 0 or 3. The large arrows indicate the position of the 21 kDa hGH protein.

Cell fractionation and SDS-PAGE analysis show that hGH is found in the insoluble fraction in both expression systems (FIG. 4). Surprisingly, approximately 7× more hGH monomer was purified from *P. fluorescens*, compared to *E. coli*, despite a difference of only 1.6× in protein production per gram of dry biomass.

TABLE 11

Comparison of hGH purification from *E. coli* and *P. fluorescens*

|  | Wet Biomass (wet g) | Purified Monomer (mg) | Purified Dimer (mg) |
|---|---|---|---|
| 1.62-1.75 L portion of *P. fluorescens* containing rh-GH | | | |
| Soluble | minimal | NA | NA |
| Lipid Extract | None detected | — | — |
| Lipid Insoluble | 62.2-63.1 | 1483 | 346 |
| 1.5-1.6 L portion of *E. coli* containing rh-GH | | | |
| Soluble | minimal | NA | NA |
| Lipid Extract | None detected | — | — |
| Lipid Insoluble | 35.0 | 200 | 333 |

Example 4

Expression of Proteins in the Periplasm
Characterization of Secretion Signal Peptides

*Pseudomonas fluorescens* secretion signal peptides were discovered by formation and expression of alkaline phosphatase (phoA) coding sequence-genomic DNA fusions and are described in more detail in U.S. application Ser. No. 10/996,007, filed Nov. 22, 2004. Six of the expressed fusions were further characterized as follows.

The cleavage site for the signal sequences for the secreted genes identified as phoA fusions was deduced by comparison to homlogous proteins from other Pseudomonads, by the SPScan program (Menne et al, 2000). The cleavage site of the putative lipoprotein was deduced by comparison to signal peptidase II motifs; signal peptidase II specifically cleaves the signal sequences of lipoproteins. All six of the signal peptides were analyzed using SignalP (a software program for analysis of putative signal peptides; available from the Center for Biological Sequence Analysis of the Technical University of Denmark, at http://www.cbs.dtu.d-klservices/SignalP/.) Also see, Nielson et al. (1997) Protein Engineering 10:1-6. In some cases, a supplementary source was used to further characterize the identity of the signal peptide. This information is present in Table 12.

TABLE 12

Identities of Secretion Signal Peptides

| Identity | Putative Amino Acid Sequence |
|---|---|
| Putative porin E1 precursor, OprE | Lys Lys Ser Thr Leu Ala Val Ala Val Thr Leu Gly Ala Ile Ala Gln Gln Ala Gly Ala (SEQ ID NO: 8) |
| Putative phosphate binding protein | Lys Leu Lys Arg Leu Met Ala Ala Met Thr Phe Val Ala Ala Gly (SEQ ID NO: 9) |
| Putative azurin | Phe Ala Lys Leu Val Ala Val Ser Leu Leu Thr Leu Ala Ser Gly Gln Leu Leu Ala (SEQ ID NO: 10) |
| Putative periplasmic lipoprotein B precursor | Ile Lys Arg Asn Leu Leu Val Met Gly Leu Ala Val Leu Leu Ser (SEQ ID NO: 11) |
| Putative Lys-Arg-Orn binding protein | Gln Asn Tyr Lys Lys Phe Leu Leu Ala Ala Ala Val Ser Met Ala Phe Ser Ala Thr Ala Met Ala (SEQ ID NO: 12) |
| Putative Fe(III) binding protein | Met Ile Arg Asp Asn Arg Leu Lys Thr Ser Leu Leu Arg Gly Leu Thr Leu Thr Leu Leu Ser Leu Thr Leu Leu Ser Pro Ala Ala His Ser (SEQ ID NO: 13) |

Western Analysis of the phoA Fusion Proteins to Detect Fusion Proteins

To analyze whether the fusion proteins were produced, Western analysis with antibody to alkaline phosphatase was carried out on cultures separated by centrifugation into a whole-cell fraction (cytoplasm and periplasm) and a cell-free broth fraction. Of five strains for which the site of insertion was determined, four (putative azurin, putative phosphate binding protein, putative periplasmic lipoprotein B, putative Fe(III) binding protein) produced a fusion protein of the expected size, and one (putative oprE protein) produced a protein about 40 kD smaller than predicted, and one (putative Lys-Arg-Orn binding protein) produced a protein about 20 kD smaller than predicted.

Proteins were separated by SDS-PAGE and were transferred to nitrocellulose membrane at 40 V for one hour using the Xcell SureLock™ Mini-Cell and XCell II™ Blot Module (Invitrogen). Western experiments were performed using the instruction provided from SuperSignal West H is Probe™ Kit (Pierce).

Construction, Expression, and Characterization of a pbp-hGH Fusion

The *P. fluorescens* phosphate binding protein secretion leader was fused to the N-terminus of the mature domain of the human growth hormone (hGH) gene and tested for expression and secretion.

The pbp signal-sequence coding region was PCR amplified from a clone of the *P. fluorescens* pbp signal sequence as template, using sig_pbp for (gctctagaggaggtaacttatgaaact-gaaacg, SEQ ID NO: 22) and pbp-hgh (gggaatggttgggaaggc-caccgcgttggc, SEQ ID NO: 23) primers, then gel-purified. This resulted in production of an oligonucleotide fragment containing the pbp signal peptide CDS and the coding sequence for the 5' end of the mature domain of hGH.

A cDNA encoding the human growth hormone was PCR-amplified from a human pituitary cDNA library (Clontech, Palo Alto Calif.) using primers ELVIfor (agagaactag-taaaaaggagaaatccatggctacaggctcccggacgtcc, SEQ ID NO: 6) and ELVIrev (agagactcgagtcattagaagccacagctgccctccac, SEQ ID NO: 7), which were designed to amplify only the mature domain of hGH, and cloned into pMYC1803/SpeI XhoI, forming pDOW2400. The mature hGH gene was amplified from pDOW2400, using primers pbp_hgh_rev-comp (gccaacgcggtggccttcccaaccattccc, SEQ ID NO: 14) and hgh-rev (agagactcgagtcattagaagccacagctgccctccaca-gagcggcac, SEQ ID NO: 15), then purified with Strataprep columns (Stratagene) to remove primers and other reaction components. To make the polynucleotide encoding the pbp-hGH fusion, the two PCR reactions were combined and amplified again with sigpbp for and hgh_rev in order to link the two pieces. The expected 681 bp fragment was purified with Strataprep as above, restriction digested with XbaI and XhoI and ligated to dephosphorylated pDOW1269/XhoISpeI to form pDOW 1323-10, placing pbp-hGH under control of the tac promoter in a vector analogous to pMYC1803, but with a pyrF selectable marker in place of a tetR tetracycline resistance marker gene. The ligation mix was transformed into MB101 pyrF proC lacI$^{Q1}$. Inserts were sequenced by The Dow Chemical Company using the method described above. The DNA and amino acid sequence of this fusion is presented in (FIG. 10) and (FIG. 11), respectively.

The resulting strains were tested first at the shake flask scale. Induced bands of the expected size for processed and unprocessed (22.2 kDa and 24.5 kDa, respectively) were detected by SDS-PAGE. About half of the protein was processed (indicating localization to the periplasm), and of the processed about half was in the soluble fraction and half in the insoluble fraction. Expression studies were scaled up to 20-L bioreactors. Densitometry of the Coomassie-stained SDS-PAGE gels showed that 18% of the total hGH produced was processed and soluble. The strain produced 3.2 g/L of all forms of hGH; processed and soluble was 0.6 g/L.

Construction, Expression, and Characterization of pbp-scFv Fusion

The putative 24 amino acid signal sequence of phosphate binding protein (i.e. including MetI) was fused to the open reading frame of the gal2 scFv gene (gal2) at the +2 amino acid (Ala) position. See FIG. 8 and FIG. 9. The signal sequence appears to be processed, indicating secretion to the periplasm. Moreover, there is secretion to the broth, in that protein was detected in the cell free culture supernatant. Surprisingly, fusion to the phosphate binding protein signal sequence appears to improve expression of gal2 scFv in *P. fluorescens*. Without the secretion signal fused at the amino terminus, expression of gal2 scFv was not detectable.

Cloning of Gal2

PCR was performed using primers sig_pbp for (above) and pbp_gal2SOE rev (ctgcacctgggcggccaccgcgtt, SEQ ID NO: 24), which contains a reverse complement of pbp_gal1SOE for (aaccgcggtggccgcccaggtgcag, SEQ ID NO: 25), and using a plasmid encoding the *P. fluorescens* pbp secretion signal peptide as template. This resulted in production of an oligonucleotide fragment containing the pbp signal peptide coding sequence (CDS) and a CDS for the 5' end of the gal2 single chain antibody (scAb or scFv).

PCR was performed using primers pbp_gal2SOE for and scFv2rev (acgcgtcgacttattaatggtg, SEQ ID NO: 26, atgatggtgatgtgcggccgcacgtttgatc SEQ ID NO: 27). This resulted in production of a polynucleotide fragment containing a CDS encoding the 3'end of the pbp signal and the open reading frame (ORE) encoding gal2.

Reaction products were purified. About 15 ng of each was used as a "template" DNA in a further PCR reaction using primers sig_pbp_for and scFv2rev. This resulted in production of a nucleic acid fragment with the pbp signal peptide CDS fused to the gal2 coding sequence.

The predicted −1 amino acid of the signal sequence (that is the last amino acid prior to the proposed cleavage site) was fused to the +2 amino acid of the gal2 scFv (Ala). The resulting fusion was cloned into the *P. fluorescens* vector pMYC1803 under control of the Ptac promoter to produce plasmid and pDOW1123 (pbp:gal2). The plasmid was transformed into *P. fluorescens* strain MB 101 carrying plasmid pCN51-lacI (described in U.S. application Ser. No. 10/994,138, filed Nov. 19, 2004.

Fusion of the Putative Phosphate Binding Protein Signal Sequence to gal2 scFv

The phosphate binding protein signal sequence was fused to a single chain antibody gene and tested for secretion to the periplasm and/or to the culture supernatant.

TABLE 13 secreted Gal2 fermentation summary (*compared to BSA standards)

|  | E. coli | P. fluorescens | Pf/Ec |
|---|---|---|---|
| Fermentation Time (hr) | 8-9 | 50-70 | 8 |
| Max Gal2 scFv titr (*g/L) | 1.6 (0.8 processed) | 9.3 (25% cv) | 6 (12) |
| Dry biomass (g/L) | 18 | (70) | 4 |
| Gal2 scFv/biomass (% w/w) | 8.9 (4.4 processed) | 13 | 1.5 (3) |

The resulting strains were tested first at the shake flask scale. Induced bands of the expected size for unprocessed and processed gal2 (29 kDa and 27 kDa) were detected via SDS-PAGE in the insoluble protein fraction (data not shown). Expression studies were scaled up to 20 L fermentation. Again, SDS-PAGE analysis showed that the majority of the induced protein is found in the insoluble protein fraction.

The Western analysis also indicated that some processed gal2 is present in the soluble protein fraction for pbp:gal2 (pDOW1123). Western analysis of periplasmic fractions prepared from strains carrying pDOW 1123 (using the Epicentre periplast kit) showed the presence of soluble gal2 protein.

Recombinant gal2 scFv was isolated from the cell extract of a shake flask experiment using the Qiagen Ni-NTA protocol, then refolded as described in P. Martineau et al., J. Mol. Biol. 280:117-127 (1998). This antibody was found to be active against β-galactosidase in an ELISA assay.

Example 5

Expression of Bovine γ-IFN in the Cytoplasm

*Pseudomonas fluorescens* Host Cells and Expression Systems

Production strain MB324 was used for transformation experiments and plasmid pHYC1803 was used for subcloning experiments. The *Bacillus thuringiensis* BuiBui insert of the vector was excised with restriction enzymes SpeI and XhoI prior to insertion of the bovine IFN-γ (BGI) gene. The published nucleotide sequence of BGI was obtained from GenBank using SeqWeb software. The sequence to be synthesized was modified to exclude the signal sequence and include ribosome binding, SpeI and XhoI restriction sites.

Subcloning of Interferon Genes

Conical tubes (50 mL) containing 5-mL L-broth (LB) were inoculated with ice chips from frozen glycerol stock cultures of *P. fluorescens* MB324. The cultures were incubated in a rotary shaker overnight at 300 rpm and 30° C. 0.75 mL from each culture was used to inoculate 50 mL of LB in 250-mL side-baffled flasks. The cultures were shaken for two hours at 300 rpm and 30° C. and grown to an A600 (absorbance at 600 nM) of 0.2 to 0.3. Cultures were then cooled on ice and pelleted by centrifugation at 3000 rpm. Pelleted materials was washed with cold, sterile, distilled water three times and the pellets were re-suspended in water.

The cell suspensions (about 100 µL each) were added to electroporation cuvettes, mixed with 10 µL of either interferon gene or control ligation mixtures; re-suspended cells were electroporated with a BioRad GenePulser in 0.2 cm cuvettes at 200 ohms, 25 µF and 2.25 kV and "pulsed" at time-constants between 4.6 and 4.8.

One-mL of LB was added to each sample, and the liquid was transferred to iced 2059 Falcon tubes. The tubes were loosely capped, shaken for two hours at 280 rpm and 30° C. 100 µL to 200 µL aliquots were plated on L-broth-tetracycline (LB-tetracycline) (30 µg/mL) agar and incubated at 30° C. overnight. One colony from each of two 100 µL platings and two colonies from a 200 µL plating were randomly selected and used to inoculate 50 mL conical tubes with LB-tetracycline broth, as described above. Samples of the resulting cultures were mixed with sterile glycerol (1.0 mL culture plus 0.25 mL 75% glycerol) and stored at −70° C. The remaining culture (1.8 mL) was centrifuged for 10 minutes in a 2 mL Eppendorf tube. The pellets were re-suspended in 0.5 mL of Qiagen P1 solution, followed by gentle inversion six-times with 0.5 mL P2 solution.

Within about five minutes, the sample was re-inverted six times with N3 solution and iced. The chilled sample was centrifuged for ten minutes, carefully separated from the pellet and surface scum, and the resulting supernatant liquid (about 1.5 mL) was transferred to a fresh Eppendorf tube. The sample was further purified with a Qiagen spin column and collection tube by spin-loading the entire 1.5 mL sample onto the column with two, 30 second, 14000 RPM (14 K) spins of about 0.7 mL to 0.8 mL aliquots. The spin-column was washed with 0.62 mL Qiagen PB and 0.85 mL PE, with a final spin of 90 seconds. The column was transferred to a new Eppendorf tube, eluted for 1 minute with 50 µL Tris-EDTA, and spun for one minute at 14 K. The eluent was transferred to a new Eppendorf tube and stored at −20° C. The resulting mini-preps were digested with XhoI and SpeI and analyzed by agarose-gel electrophoresis.

Expression and Quantitation of Interferon Protein

Based on these results, one clone of MR324 with an IFN-γ insert was selected for expression analysis. *P. fluorescens* strains MR843 and MR837 were used as interferon-negative controls. LB-tetracycline seed-flasks were grown to A600 0.15 to 0.5 and normalized to 0.15 for 2% dilution into 1-liter shake flasks containing 200-mL tetracycline production medium. *P. fluorescens* cells were grown to approximately A600 0.4 at 30° C. with rotary shaking for 24 hours. The cells were induced with 0.6 mL of 100 mM IPTG+5 mL 40% MSG for an additional 48 hours. The cells were examined microscopically for general appearance and inclusion body formation.

Fifty-mL samples were taken and stored at 4° C. in conical tubes for analysis of expression by sodium dodecyl-sulfate polyacrylamide-gel electrophoresis (SDS-PAGE.) A total of 100 µL was centrifuged for five minutes at 14 K to pellet the cells. Pellets were re-suspended in 100 µL 1× Laemmli buffer and boiled for 3 minutes, and supernatant samples were diluted 1:1 with Laemmli buffer prior to being boiled. Ten µL of boiled sample were mixed with 30 µL of fresh Laemmli buffer and boiled for an additional 3-minutes. The preparations were frozen overnight, thawed the following day, heated to 70° C. for five minutes, loaded (10 µL each) into the wells of a 12-lane, 15% BioRad gel, and electrophoresed with BioRad running buffer. The electrophoresis ran for 20 minutes at 50 volts followed by 1 hour 20-minutes at 75 volts. After the run, the gels were washed in distilled water three times for five minutes each and stained with BioRad's BioSafe stain for 1.5 hours. The stained gels were de-stained in distilled water with one change after one hour. Quantitation was accomplished with an MD densitometer by comparing the Coomassie Blue intensity of the samples to interferon-minus controls and a BSA protein standard.

The BuiBui toxin gene was replaced with the bovine gamma-interferon (BGI) gene at the SpeI and XhoI sites of pMYC1803. All the transformants selected had the desired interferon insert, as verified first by agarose-gel electrophoresis, and then by sequencing the inserted DNA. One clone of the DnaK, chaperonin containing strain of *P. fluorescens*, MB324, was selected for further study.

A major band of protein was observed at the molecular weight expected for BGI and expression of BGI in *Pseudomonas* was about 40% of total cellular protein. Identity of this major band with authentic BGI was confirmed by purification of the protein contained in the major band, coupled with bioassays of the purified product. With the optimization of expression and high-density fermentation achievable with *Pseudomonas*, interferon production of greater than 1000 Kg can be attained in a single fermentation production run.

Solubility Assay

A 0.975 mL volume of *P. fluorescens* culture was centrifuged in a microfuge for 5 minutes at 14,000 RPM. The supernatant liquid was decanted and the cells were resuspended in lysis buffer up to the starting volume. (Lysis buffer: Tris HCl, 50 mM, pH 7.5 final; NaCl, 200 mM; glycerol, 5% v/v; EDTA, 20 mM; Triton X-100, 5% v/v; and, added last, DTT, 1 mM) Screw-cap microfuge tubes (2 mL) were filled about ¾ full with 0.1 mm glass beads and topped off with cell suspension. The tubes were given a quick shake to mix the beads and remove air bubbles, and further filled to the top with cell suspension. The tubes were capped, sealed, and inserted into a BioSpec mini bead-beater for 60 seconds at 5000 rpm. The samples were kept on ice between beatings and beat 3 to 5 times until about 90% of the cells were lysed. Cell lysis was observed by microscopic observation. A volume of 0.025 mL of the lysed cell preparation was pipetted from each tube, minus beads, into new microfuge tubes and centrifuged for 5 minutes. The supernatant fraction was carefully transferred to another tube with 0.075 mL LSB, and 0.100 mL LSB was added to the pellet fraction. The supernatant and pellet fractions were re-suspended with a Vortex stirrer, the tubes were capped, placed in a boiling water bath for five minutes, and 0.005 mL to 0.010 mL aliquots of the fractions SDS PAGE were analyzed. Assessment of expressed BGI protein solubility in *Pseudomonas*, using either a French-Press or a BioSpec Mini Bead-Beater produced equivalent results.

The solubility of BGI in *Pseudomonas* cells was tested and indicated that most, if not all, of the BGI remained in soluble form. To do these solubility-tests, viable unamended *Pseudomonas* cells were broken in a French Press (or mini-bead beater), and centrifuged to separate cell debris and any inclusion bodies from soluble proteins. SDS gels of these two fractions indicated that BGI was retained in the soluble portion, whereas BAI (bovine α-interferon), a marker in this example that had been cloned and expressed for another experiment, occurred primarily in the insoluble fraction. Furthermore, unlike BGI, BAI formed large inclusions in *Pseudomonas*, which were highly visible under phase-contrast microscopy.

SDS-PAGE analysis of French-pressed *P. fluorescens* cultures containing both BAI and BGI were conducted. *Pseudomonas* cells were ruptured in a French Press and centrifuged at 16000 g for five minutes. Supernatant samples showed a single, major band (about 17 kDa) of soluble BGI with no BAI visible. Pelleted samples showed a major band (about 18 kDa) of insoluble BAI together with small amounts of contaminating soluble BGI. The contamination appears to be due to spillover from the supernatant fraction and unlysed cells.

Both the amount and activity of BGI in *Pseudomonas* cells were high. As illustrated in the examples, *P. fluorescens* is a good biofactory, capable of producing up to 40% or more of total cell protein as recombinant protein, such as interferon and the cells produce active protein.

The invention claimed is:

1. A process for producing a recombinant mammalian protein in a *Pseudomonas fluorescens* host cell comprising:
   a. transforming said *Pseudomonas fluorescens* host cell with a nucleic acid encoding the recombinant mammalian protein operably linked to a periplasmic secretion leader coding sequence;
   b. growing the transformed *Pseudomonas fluorescens* host cell under conditions that allow production of the recombinant mammalian protein, and secretion of the recombinant mammalian protein into the periplasm; and
   c. isolating the recombinant mammalian protein;
wherein the recombinant mammalian protein is produced as 5-40% total cell protein, wherein the recombinant mammalian protein is present in the host cell in a soluble form, and wherein the soluble recombinant mammalian protein is produced at a titre in the *P. fluorescens* host cell that is about 1.5-fold to about 8-fold higher than the titre of the soluble recombinant mammalian protein produced in an *E. coli* host cell.

2. The process of claim 1, further comprising substantially purifying the recombinant mammalian protein isolated in step (c).

3. The process of claim 1, wherein the recombinant mammalian protein has a mass of between about 1 kD and about 500 kD.

4. The process of claim 3, wherein the recombinant mammalian protein has a mass of greater than about 30 kD.

5. The process of claim 1 wherein the recombinant mammalian protein is produced as about 10% to 40% total cell protein.

6. The process of claim 1 wherein the recombinant mammalian protein is produced as about 20% to 40% total cell protein.

7. The process of claim 1 wherein the recombinant mammalian protein is produced as about 30% to 40% total cell protein.

8. The process of claim 1 wherein the recombinant mammalian protein is produced as about 15% to 40% total cell protein.

9. The process of claim 1, wherein the host cell comprises at least one heterologous regulatory element.

10. The process of claim 9, wherein the heterologous regulatory element comprises at least one Lac repressor protein.

11. The process of claim 10, wherein the at least one Lac repressor protein is LacI.

12. The process of claim 1, wherein the recombinant mammalian protein is present in the host cell in an active form.

13. The process of claim 1, wherein the recombinant mammalian protein is a mammalian interleukin, cytokine, chemokine, fibroblast growth factor, insulin-like growth factor, nerve growth factor, interferon, transforming growth factor, or TNF superfamily protein.

14. The process of claim 1, wherein the soluble recombinant mammalian protein is produced at a titre in the *P. fluorescens* host cell that is about 2-fold to 8-fold higher than the titre of soluble recombinant mammalian protein produced in an *E. coli* host cell.

15. The process of claim 1, wherein the soluble recombinant mammalian protein is produced at a titre in the *P. fluorescens* host cell that is about 3-fold to 8-fold higher than the titre of soluble recombinant mammalian protein produced in an *E. coli* host cell.

16. The process of claim 1, wherein the soluble recombinant mammalian protein is produced at a titre in the *P. fluorescens* host cell that is about 4-fold to 8-fold higher than the titre of soluble recombinant mammalian protein produced in an *E. coli* host cell.

17. The process of claim 13, wherein the recombinant mammalian protein is selected from the group consisting of: IL-1, IL-1α, IL-1β, IL-2, IL-3, IL-4, IL-5, IL-6, IL-7, IL-8, IL-9, IL-10, IL-11, IL-12, IL-12elasti, IL-13, IL-15, IL-16, IL-18, IL-18BPa, IL-23, IL-24, VIP, erythropoietin, GM-CSF, G-CSF, M-CSF, PDGF, MSF, FLT-3ligand, EGF, aFGF (FGF-1), bFGF (FGF-2), FGF-3, FGF-4, FGF-5, FGF-6, FGF-7, IGF-1,IGF-2, TNF, Lymphotoxin, NGF, VEGF, IFN-α, IFN-β, and IFN-γ, leukemia inhibitory factor (LIF), ciliary neurotrophic factor (CNTF), oncostatin M, stem cell factor (SCF), TGF-α, TGF-β1, LIGHT/TNFSF14, STALL-1/TNFSF13B (BLy5, BAFF, THANK), TNFα/TNFSF2, TWEAK/TNFSF12, BCA-1/BLC-1, BRAK/Kec, CXCL16, CXCR3, ENA-78/LIX, Eotaxin-1, Eotaxin-2/MPIF-2, Exodus-2/SLC, Fractalkine/Neurotactin, GROalpha/MGSA, HCC-1, I-TAC, Lymphotactin/ATAC/SCM, MCP-1/MCAF, MCP-3, MCP-4, MDC/STCP-1/ABCD-1, MIP-1α, MIP-1β, MIP-21α/GROβ, MIP-31α/Exodus/LARC, MIP-31α/Exodus-3/ELC, MIP-4/PARC/DC-CK1, PF-4, RANTES, SDF11α, TARC, and TECK.

18. The process of claim 17, wherein the recombinant mammalian protein is IFN-α.

19. The process of claim 17, wherein the recombinant mammalian protein is IFN-β.

20. The process of claim 17, wherein the recombinant mammalian protein is IFN-γ.

21. The process of claim 17, wherein the recombinant mammalian protein is G-CSF.

22. The process of claim 17, wherein the recombinant mammalian protein is TGF-α.

23. The process of claim 17, wherein the recombinant mammalian protein is TGF-β1.

24. The process of claim 17, wherein the recombinant mammalian protein is TNF-α.

* * * * *